(12) United States Patent
Adair et al.

(10) Patent No.: US 12,358,906 B2
(45) Date of Patent: Jul. 15, 2025

(54) UREA COMPOUNDS AND COMPOSITIONS AS SMARCA2/BRM ATPASE INHIBITORS

(71) Applicant: NOVARTIS AG, Basel (CH)

(72) Inventors: Christopher Adair, Woodstock (CA); Katsumasa Nakajima, Winchester, MA (US); Rukundo Ntaganda, Weymouth, MA (US); Julien Papillon, Somerville, MA (US); Troy Douglas Smith, Nashua, NH (US)

(73) Assignee: Novartis AG, Basel (CH)

( * ) Notice: Subject to any disclaimer, the term of this patent is extended or adjusted under 35 U.S.C. 154(b) by 0 days.

(21) Appl. No.: 18/602,126

(22) Filed: Mar. 12, 2024

(65) Prior Publication Data

US 2024/0270738 A1     Aug. 15, 2024

Related U.S. Application Data

(63) Continuation of application No. 17/268,512, filed as application No. PCT/IB2019/056847 on Aug. 12, 2019, now Pat. No. 11,958,846.

(60) Provisional application No. 62/765,138, filed on Aug. 17, 2018.

(51) Int. Cl.
    C07D 417/12     (2006.01)
    A61K 45/06     (2006.01)

(52) U.S. Cl.
    CPC ............ C07D 417/12 (2013.01); A61K 45/06 (2013.01)

(58) Field of Classification Search
    CPC .. C07D 417/12; A61K 45/06; A61K 31/4439; A61P 35/00; A61P 35/02
    See application file for complete search history.

(56) References Cited

U.S. PATENT DOCUMENTS

| | | | | |
|---|---|---|---|---|
| 2,871,243 | A * | 1/1959 | Adams ................. | C07D 275/02 548/214 |
| 6,863,647 | B2 * | 3/2005 | Pevarello ................. | A61P 9/10 548/196 |
| 11,958,846 | B2 * | 4/2024 | Adair ................... | C07D 417/12 |
| 2005/0250816 | A1 | 11/2005 | Piotrowski et al. | |
| 2008/0167340 | A1 | 7/2008 | Delong et al. | |
| 2021/0323956 | A1 | 10/2021 | Adair | |

FOREIGN PATENT DOCUMENTS

| | | | | |
|---|---|---|---|---|
| CN | 103880737 | A * | 6/2014 | ........... C07D 213/75 |
| CN | 105481723 | A | 4/2016 | |
| EP | 1256574 | A1 * | 11/2002 | .............. A61P 11/06 |
| WO | 9921835 | A1 | 5/1999 | |
| WO | 0214311 | A2 | 2/2002 | |
| WO | 02094813 | A1 | 11/2002 | |
| WO | 2004002481 | A1 | 1/2004 | |
| WO | 2004085433 | A2 | 10/2004 | |
| WO | 2009113736 | A1 | 9/2009 | |
| WO | 2016008433 | A1 | 1/2016 | |
| WO | 2016138114 | A1 | 9/2016 | |
| WO | 2018187414 | A1 | 10/2018 | |
| WO | 2020126968 | A2 | 6/2020 | |

OTHER PUBLICATIONS

Lowinger B. Timothy, Riedl Bernd, Dumas Jacques and Smith A. Roger, Design and Discovery of Small Molecules Targeting Raf-1 Kinase, Current Pharmaceutical Design 2002; 8 (25)—made of record on the IDS (Year: 2002).*
Lowinger, et al., Design and Discovery of Small Molecules Targeting RAF-1 Kinase, Current Pharmaceutical Design, Bentham, 8(25), 2269-2278, 2002.
Papillon et al, Discovery of Orally Active Inhibitors of Brahma Homolog (BRM)/ SMARCA2 ATPase Activity for the Treatment of Brahma Related Gene 1 (BRG1)/SMARCA4-Mutant Cancers, Journal of Medicinal Chemistry, 61 (22), 10155-10172, 2018.

* cited by examiner

*Primary Examiner* — Clinton A Brooks
*Assistant Examiner* — Izabela Schmidt
(74) *Attorney, Agent, or Firm* — Sophie Binet Cross

(57) ABSTRACT

A method of preparing compound of Formula (I), or a pharmaceutically acceptable salt thereof,

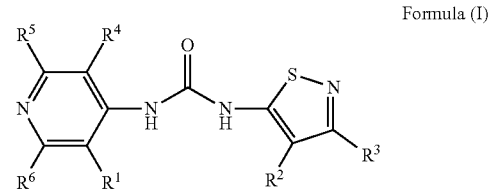

Formula (I)

wherein $R^1$ through $R^6$ are as defined herein.

13 Claims, No Drawings

Specification includes a Sequence Listing.

SEQUENCE LISTING

```
Sequence total quantity: 8
SEQ ID NO: 1           moltype = AA  length = 10
FEATURE                Location/Qualifiers
REGION                 1..10
                       note = Description of Artificial Sequence: Synthetic 10xHis
                         tag
source                 1..10
                       mol_type = protein
                       organism = synthetic construct
SEQUENCE: 1
HHHHHHHHHH                                                                 10

SEQ ID NO: 2           moltype = DNA  length = 30
FEATURE                Location/Qualifiers
misc_feature           1..30
                       note = Description of Artificial Sequence: Synthetic primer
source                 1..30
                       mol_type = other DNA
                       organism = synthetic construct
SEQUENCE: 2
gaccgaacta gtatggcttc tcaccaccat                                           30

SEQ ID NO: 3           moltype = DNA  length = 30
FEATURE                Location/Qualifiers
misc_feature           1..30
                       note = Description of Artificial Sequence: Synthetic primer
source                 1..30
                       mol_type = other DNA
                       organism = synthetic construct
SEQUENCE: 3
agcgttaagc ttttaatcct cgatggcgcg                                           30

SEQ ID NO: 4           moltype = AA  length = 852
FEATURE                Location/Qualifiers
REGION                 1..852
                       note = Description of Artificial Sequence: Synthetic
                         polypeptide
source                 1..852
                       mol_type = protein
                       organism = synthetic construct
SEQUENCE: 4
```

```
MASHHHHHHH HHHAQHDEAV DNKFNKEQQN AFYEILHLPN LNEEQRNAFI QSLKDDPSQS   60
ANLLAEAKKL NDAQAPKVDN KFNKEQQNAF YEILHLPNLN EEQRNAFIQS LKDDPSQSAN  120
LLAEAKKLND AQAPKVDANG GGGSGGGGSL EVLFQGPEES DSDYEEEDEE EESSRQETEE  180
KILLDPNSEE VSEKDAKQII ETAKQDVDDE YSMQYSARGS QSYYTVAHAI SERVEKQSAL  240
LINGTLKHYQ LQGLEWMVSL YNNNLNGILA DEMGLGKTIQ TIALITYLME HKRLNGPYLI  300
IVPLSTLSNW TYEFDKWAPS VVKISYKGTP AMRRSLVPQL RSGKFNVLLT TYEYIIKDKH  360
ILAKIRWKYM IVDEGHRMKN HHCKLTQVLN THYVAPRRIL LTGTPLQNKL PELWALLNFL  420
LPTIFKSCST FEQWFNAPFA MTGERVDLNE EETILIIRRL HKVLRPFLLR RLKKEVESQL  480
PEKVEYVIKC DMSALQKILY RHMQAKGILL TDGSEKDKKG KGGAKTLMNT IMQLRKICNH  540
PYMFQHIEES FAEHLGYSNG VINGAELYRA SGKFELLDRI LPKLRATNHR VLLFCQMTSL  600
MTIMEDYFAF RNFLYLRLDG TTKSEDRAAL LKKFNEPGSQ YFIFLLSTRA GGLGLNLQAA  660
DTVVIFDSDW NPHQDLQAQD RAHRIGQQNE VRVLRLCTVN SVEEKILAAA KYKLNVDQKV  720
IQAGMFDQKS SSHERRAFLQ AILEHEEENE EEDEVPDDET LNQMIARREE EFDLFMRMDM  780
DRRREDARNP KRKPRLMEED ELPWIIKDDA EVERLTCEEE EEKIFGRGSR QRRDVDYSDA  840
LTEKQWLRAI ED                                                     852

SEQ ID NO: 5             moltype = DNA   length = 77
FEATURE                  Location/Qualifiers
misc_feature             1..77
                         note = Description of Artificial Sequence: Synthetic primer
source                   1..77
                         mol_type = other DNA
                         organism = synthetic construct
SEQUENCE: 5
ggggacaagt ttgtacaaaa aagcaggctt cgaaggagat agaaccatgg aagaaagtgg   60
ctcagaagaa gaggaag                                                 77

SEQ ID NO: 6             moltype = DNA   length = 76
FEATURE                  Location/Qualifiers
misc_feature             1..76
                         note = Description of Artificial Sequence: Synthetic primer
source                   1..76
                         mol_type = other DNA
                         organism = synthetic construct
SEQUENCE: 6
ggggaccact ttgtacaaga aagctgggtc tcagtgatga tgatgatgat gctcctcgat   60
ggccttgagc cactgc                                                  76

SEQ ID NO: 7             moltype = AA   length = 711
FEATURE                  Location/Qualifiers
REGION                   1..711
                         note = Description of Artificial Sequence: Synthetic
                         polypeptide
source                   1..711
                         mol_type = protein
                         organism = synthetic construct
SEQUENCE: 7
MEESGSEEEE EEEEEQPQA AQPPTLPVEE KKKIPDPDSD DVSEVDARHI IENAKQDVDD   60
EYGVSQALAR GLQSYYAVAH AVTERVDKQS ALMVNGVLKQ YQIKGLEWLV SLYNNNLNGI  120
LADEMGLGKT IQTIALITYL MEHKRINGPF LIIVPLSTLS NWAYEFDKWA PSVVKVSYKG  180
SPAARRAFVP QLRSGKFNVL LTTYEYIIKD KHILAKIRWK YMIVDEGHRM KNHHCKLTQV  240
LNTHYVAPRR LLLTGTPLQN KLPELWALLN FLLPTIFKSC STFEQWFNAP FAMTGEKVDL  300
NEEETILIIR RLHKVLRPFL LRRLKKEVEA QLPEKVEYVI KCDMSALQRV LYRHMQAKGV  360
LLTDGSEKDK KGKGGTKTLM NTIMQLRKIC NHPYMFQHIE ESFSEHLGFT GGIVQGLDLY  420
RASGKFELLD RILPKLRATN HKVLLFCQMT SLMTIMEDYF AYRGFKYLRL DGTTKAEDRG  480
MLLKTFNEPG SEYFIFLLST RAGGLGLNLQ SADTVIIFDS DWNPHQDLQA QDRAHRIGQQ  540
NEVRVLRLCT VNSVEEKILA AAKYKLNVDQ KVIQAGMFDQ KSSSHERRAF LQAILEHEEQ  600
DEEEDEVPDD ETVNQMIARH EEEFDLFMRM DLDRRREEAR NPKRKPRLME EDELPSWIIK  660
DDAEVERLTC EEEEEKMFGR GSRHRKEVDY SDSLTEKQWL KAIEEHHHHH H           711

SEQ ID NO: 8             moltype = DNA   length = 12150
FEATURE                  Location/Qualifiers
misc_feature             1..12150
                         note = Description of Artificial Sequence: Synthetic
                         polynucleotide
source                   1..12150
                         mol_type = other DNA
                         organism = synthetic construct
SEQUENCE: 8
ttgattattg actagttatt aatagtaatc aattacgggg tcattagttc atagcccata   60
tatggagttc cgcgttacat aacttacggt aaatggcccg cctggctgac cgcccaacga  120
cccccgccca ttgacgtcaa taatgacgta tgttcccata gtaacgccaa tagggacttt  180
ccattgacgt caatgggtgg agtatttacg gtaaactgcc cacttggcag tacatcaagt  240
gtatcatatg ccaagtacgc ccctattga cgtcaatgac ggtaaatggc ccgcctggca  300
ttatgcccag tacatgacct tatgggactt tcctacttgg cagtacatct acgtattagt  360
catcgctatt accatggtga tgcggttttg gcagtacatc aatgggcgtg gatagcggtt  420
tgactcacgg ggatttccaa gtctccaccc cattgacgtc aatgggagtt tgttttggca  480
ccaaaatcaa cgggactttc caaaatgtcg taacaactcc gccccattga cgcaaatggg  540
cggtaggcgt gtacggtggg aggtctatat aagcagagct cgtttagtga accgtcagat  600
```

```
cgcctggaga cgccatccac gctgttttga cctccataga agacaccggg accgatccag    660
cctccgcggc cgggaacggt gcattggaac gcggattccc cgtgccaaga gtgacgtaag    720
taccgcctat agagtctata ggcccacccc cttggcttct tatgcgacgg atcgatcccg    780
taataagctt cgaggtccgc ggccggccgc gttgacgcgc acggcaagag gcgaggggcg    840
gcgactggtg agagatgggt gcgagagcgt cagtattaag gggaggagaa ttagatcgat    900
gggaaaaaat tcggttaagg ccaggggaa agaaaaaata taaattaaaa catatagtat     960
gggcaagcag ggagctagaa cgattcgcag ttaatcctgg cctgttagaa acatcagaag   1020
gctgtagaca aatactggga cagctacaac catcccttca gacaggatca gaagaactta   1080
gatcattata taatacagta gcaaccctct attgtgtgca tcaaggata gagataaaag    1140
acaccaagga agctttagac aagatagagg aagagcaaaa caaaagtaag aaaaaagcac   1200
agcaagcagc agctgacaca ggacacagca atcaggtcag ccaaaattac cctatagtgc   1260
agaacatcca ggggcaaatg gtacatcagg ccatatcacc tagaacttta aatgcatggg   1320
taaaagtagt agaagagaag gctttcagcc cagaagtgat acccatgttt tcagcattat   1380
cagaaggagc caccccacaa gatttaaaca ccatgctaac acagtgggg ggacatcaag    1440
cagccatgca aatgttaaaa gagaccatca atgaggaagc tgcagaatgg gatagagtgc   1500
atccagtgca tgcagggcct attgcaccag gccagatgag agaaccaagg ggaagtgaca   1560
tagcaggaac tactagtacc cttcaggaac aaataggatg gatgacacat aatccaccta   1620
tcccagtagg agaaatctat aaaagatgga taatcctggg attaaataaa atagtaagaa   1680
tgtatagccc taccagcatt ctggacataa gacaaggacc aaaggaaccc tttagagact   1740
atgtagaccg attctataaa actctaagag ccgagcaagc ttcacaagag gtaaaaaatt   1800
ggatgacaga aaccttgttg gtccaaaatg cgaacccaga ttgtaagact attttaaaag   1860
cattggggcc aggagcgaca ctagaagaaa tgatgacagc atgtcaggga gtggggggac   1920
ccggccataa agcaagagtt ttggctgaag caatgagcca agtaacaaat ccagctacca   1980
taatgataca gaaaggcaat tttaggaacc aaagaaagac tgttaagtgt ttcaattgtg   2040
gcaaagaagg gcacatagcc aaaaattgca gggcccctag gaaaaaggc tgttggaaat    2100
gtggaaagga aggacaccaa atgaaagatt gtactgagag aacaggctaat ttttagga    2160
agatctggcc ttcccacaag ggaaggcca ggaatttttct tcagagcaga ccagagccaa    2220
cagccccacc agaagagagc ttcaggtttg gggaagagac aacaactccc tctcagaagc   2280
aggagccgat agacaaggaa ctgtatcctt tagcttccct cagatcactc tttggcagcg   2340
acccctcgtc acaataaaga taggggggca attaaaggaa gctctattag atacaggagc   2400
agatgataca gtattagaag aaatgaattt gccaggaaga tggaaaccaa aaatgatagg   2460
gggaattgga ggttttatca aagtaagaca gtatgatcag atactcatag aaatctgcgg   2520
acataaagct ataggtacag tattagtagg acctacacct gtcaacataa ttggaagaaa   2580
tctgttgact cagattggct gcactttaaa ttttcccatt agtcctattg agactgtacc   2640
agtaaaatta aagccaggaa tggatggccc aaaagttaaa caatggccat tgacagaaga   2700
aaaaataaaa gcattagtag aaatttgtac agaaatggaa aaggaaggaa aatttcaaa    2760
aattgggcct gaaaatccat acaatactcc agtatttgcc ataaagaaaa aagacagtac   2820
taaatggaga aaattagtag atttcagaga acttaataag agaactcaag atttctggga   2880
agttcaatta ggaataccac atcctgcagg gttaaaacag aaaaaatcag taacagtact   2940
ggatgtgggc gatgcatatt tttcagttcc cttagataaa gacttcagga agtatactgc   3000
atttaccata cctagtataa acaatgagac accagggatt agatatcagt acaatgtgct   3060
tccacaggga tggaaaggat caccagcaat attccagtgt agcatgacaa aaatcttaga   3120
gccttttaga aaacaaaatc cagacatagt catctataca tatgtgatg atttgtatgt    3180
aggatctgac ttagaaaatag ggcagcatag aacaaaaata gaggaactga gacaacatct   3240
gttgaggtgg ggatttacca caccagacaa aaaacatcag aaagaacctc cattcctttg   3300
gatgggttat gaactccatc ctgataaatg gacagtacag cctatagtgc tgccagaaaa   3360
ggacagctgg actgtcaatg acatacagaa attagtggga aaattgaatt gggcaagtca   3420
gatttatgca gggattaaag taaggcaatt atgtaaactt cttaggggaa ccaaagcact   3480
aacagaagta gtaccactaa cagaagaagc agagctagaa ctggcagaaa cagggagat    3540
tctaaaagaa ccggtacatg gagtgtatta tgacccatca aaagacttaa tagcagaaat   3600
acagaagcag gggcaaggcc aatggacata tcaaatttat caagagccat ttaaaaatct   3660
gaaaacagga aagtatgcaa gaatgaaggg tgcccacact aatgatgtga aacaattaac   3720
agaggcagta caaaaaatag ccacagaaag catagtaata tggggaaaga ctcctaaatt   3780
taaattaccc atacaaaagg aaacatggga agcatggtgg acagagtatt ggcaagccac   3840
ctggattcct gagtggggagt ttgtcaatac ccctccctta gtgaagttat ggtaccagtt   3900
agagaaagaa cccataatag gagcagaaac tttctatgta gatggggcag ccaataggga   3960
aactaaatta ggaaaagcag gatatgtaac tgacagagga agacaaaaag ttgtcccct    4020
aacggacaca acaaatcaga agactgagtt acaagcaatt catctagctt tgcaggattc   4080
gggattagaa gtaaacatag tgacagactc acaatatgca ttgggaatca ttcaagcaca   4140
accagataag agtgaatcag agttagtcag tcaaataata gagcagttaa taaaaaagga   4200
aaaagtctac ctggcatggg taccagcaca caaaggaatt ggaggaaatg aacaagtaga   4260
taaattggtc agtgctggaa tcaggaaagt actattttta gatggaatag ataaggccca   4320
agaagaacat gagaaatatc acagtaattg gagagcaatg gctagtgatt ttaacctacc   4380
acctgtagta gcaaaagaaa tagtagccag ctgtgataaa tgtcagctaa aaggggaagc   4440
catgcatgga caagtagact gtagcccagg aatatggcag ctagattgta cacatttaga   4500
aggaaaagtt atcttggtag cagttcatgt agccagtgga tatatagaag cagaagtaat   4560
tccagcagag acagggcaag aaacagcata cttcctctta aaattagcag gaagatggcc   4620
agtaaaaaca gtacatacag acaatggcag caatttcacc agtactacag ttaaggccgc   4680
ctgttggtgg gcgggggatca agcaggaatt tggcattccc tacaatcccc aaagtcaagg   4740
agtaatagaa tctatgaata aagaattaag gaaaattata ggacaggtaa gagatcaggc   4800
tgaacatctt aagacagcag tacaaatggc agtattcatc cacaatttta aaagaaaagg   4860
ggggattggg ggtacagtg caggggaaag aatagtagac ataatagcaa cagacataca   4920
aactaaagaa ttacaaaaac aaattacaaa aattcaaaat tttcgggttt attacaggga   4980
cagcagagat ccagtttgga aaggaccagc aaagctcctc tggaaaggtg aaggggcagt   5040
agtaatacaa gataatagtg acataaaagt agtgccaaga agaaaagcaa agatcatcag   5100
ggattatgga aaacagatgg caggtgatga ttgtgtggca agtagacagg atgaggatta   5160
acacatggaa ttctgcaaca actgctgttt atccatttca gaattgggtg tcgacatagc   5220
agaataggcg ttactcgaca gaggagagca agaaatggag ccagtagatc ctagactaga   5280
gccctggaag catccaggaa gtcagcctaa aactgcttgt accaattgct attgtaaaaa   5340
```

```
gtgttgcttt cattgccaag tttgtttcat gacaaaagcc ttaggcatct ccctatggcag   5400
gaagaagcgg agacagcgac gaagagctca tcgaacagt cagactcatc aagcttctct    5460
atcaaagcag taagtagtac atgtaatgca acctataata gtagcaatag tagcattagt   5520
agtagcaata ataatagcaa tagttgtgtg gtccatagta atcatagaat ataggaaaat   5580
ggccgctgat cttcagacct ggaggaggag atatgaggag caattggaga agtgaattat   5640
ataaatataa agtagtaaaa attgaaccat taggagtagc acccaccaag gcaaagagaa   5700
gagtggtgca gagagaaaaa agagcagtgg gaataggagc tttgttcctt gggttcttgg   5760
gagcagcagg aagcactatg ggcgcagcgt caatgacgct gacggtacag gccagacaat   5820
tattgtctgg tatagtgcag cagcagaaca atttgctgag ggctattgag gcgcaacagc   5880
atctgttgca actcacagtc tggggcatca agcagctcca ggcaagaatc ctggctgtgg   5940
aaagatacct aaaggatcaa cagctcctgg ggatttgggg ttgctctgga aaactcattt   6000
gcaccactgc tgtgccttgg aatgctagtt ggagtaataa atctctgaa cagatttgga   6060
atcacacgac ctggatggag tgggacagag aaattaacaa ttacacaagc ttaatacact   6120
ccttaattga agaatcgcaa aaccagcaag aaaagaatga acaagaatta ttggaattag   6180
ataaatgggc aagtttgtgg aattggttta acataacaaa ttggctgtgg tatataaaat   6240
tattcataat gatagtagga ggcttggtag gtttaagaat agttttgct gtactttcta   6300
tagtgaatag agttaggcag ggatattcac cattatcgtt tcagacccac ctcccaaccc   6360
cgaggggacc cgacaggccc gaaggaatag aagaagaagg tggagagaga gacagagaca   6420
gatccattcg attagtgaac ggatccttgg cacttatctg ggacgatctg cggagcctgt   6480
gcctcttcag ctaccaccgc ttgagagact tactcttgat tgtaacgagg attgtggaac   6540
ttctgggacg caggggtgg gaagccctca aatattggtg gaatctccta caatattgga   6600
gtcaggagct aaagaatagt gctgttagct tgctcaatgc cacagccata gcagtagctg   6660
aggggacaga tagggttata gaagtagtac aaggagcttg tagagctatt cgccacatac   6720
ctagaagaat aagacagggc ttggaaagga ttttgctata agctcgaggc cgccccggtg   6780
accttcgac cttggcactg gaggtggccc ggcagaagcg cggcatcgtg atcagtgct   6840
gcaccagcat ctgctctctc taccaactgg agaactactg caactactcc caccactacc   6900
ctgtccaccc ctctgcaatg aataaaacct tgaaagagc actacaagtt gtgtgtacat   6960
gcgtgcatgt gcatatgtgg tgcggggga acatgagtgg ggctggctgg agtggcgatg   7020
ataagctgtc aaacatgaga attaattctt gaagacgaaa gggcctcgtg atacgcctat   7080
ttttataggt taatgtcatg ataataatgg tttcttagtc tagaattaat tccgtgtatt   7140
ctatagtgtc acctaaatcg tatgtgtatg atacataagg ttatgtatta attgtagccg   7200
cgttctaacg acaatatgta caagcctaat tgtgtagcat ctggcttact gaagcagacc   7260
ctatcatctc tctcgtaaac tgccgtcaga gtcggtttgg ttggacgaac cttctgagtt   7320
tctggtaacg ccgtcccgca cccggaaatg gtcagcgaac caatcagcag ggtcatcgct   7380
agccagatcc tctacgccgg acgcatcgtg gccgcatca ccgcgccac aggtgcggtt   7440
gctggcgcct atatcgccga catcaccgat ggggaagatc gggctcgcca cttcgggctc   7500
atgagcgctt gtttcggcgt gggtatgtg gcaggcccg tggccgggg actgttgggc   7560
gccatctcct tgcatgcacc attccttgcg gcggcggtgc tcaacggcct caacctacta   7620
ctgggctgct tcctaatgca ggagtcgcat aagggagagc gtcgaatggt gcactctcag   7680
tacaatctgc tctgatgccg catagttaag ccagccccga cacccgccaa cacccgctga   7740
cgcgccctga cgggcttgtc tgctcccggc atccgcttac agacaagctg tgaccgtctc   7800
cgggagctgc atgtgtcaga ggttttcacc gtcatcaccg aaacgcgcga cgcaaaggg   7860
cctcgtgata cgcctatttt tataggttaa tgtcatgata ataatggttt cttagacgtc   7920
aggtggcact tttcgggga atgtgcgcgg aaccccctatt tgtttatttt tctaaataca   7980
ttcaaatatg tatccgctca tgagacaata accctgataa atgcttcaat aatattgaaa   8040
aaggaagagt atgagtattc aacatttccg tgtcgccctt attcccttt ttgcggcatt   8100
ttgccttcct gttttgctc acccagaaac gctggtgaaa gtaaaagatg ctgaagatca   8160
gttgggtgca cgagtgggtt acatcgaact ggatctcaac agcggtaaga tccttgagag   8220
ttttcgcccc gaagaacgtt ttccaatgat gagcactttt aaagttctgc tatgtggcgc   8280
ggtattatcc cgtattgacg ccgggcaaga gcaactcggt cgccgcatac actattctca   8340
gaatgacttg gttgagtact caccagtcac agaaaagcat cttacggatg gcatgacagt   8400
aagagaatta tgcagtgctg ccataaccat gagtgataac actgcggcca acttacttct   8460
gacaacgatc ggaggaccga aggagctaac cgcttttttg cacaacatgg ggatcatgt   8520
aactcgcctt gatcgttggg aaccggagct gaatgaagcc ataccaaacg acgagcgtga   8580
caccacgatg cctgtagcaa tggcaacaac gttgcgcaaa ctattaactg gcgaactact   8640
tactctagct tcccggcaac aattaataga ctggatggag gcggataaag ttgcaggacc   8700
acttctgcgc tcggccttc cggctggctg gtttattgct gataaatctg gagccggtga   8760
gcgtgggtct cgcggtatca ttgcagcact ggggccagat ggtaagccct cccgtatcgt   8820
agttatctac acgacggga gtcaggcaac tatggatgaa cgaaatagaca gatcgctga   8880
gataggtgcc tcactgatta agcattggta actgtcagac caagtttact catatatact   8940
ttagattgat ttaaaacttc attttttaatt taaaaggatc taggtgaaga tcctttttga   9000
taatctcatg accaaaatcc cttaacgtga gttttcgttc cactgagcgt cagacccgt    9060
agaaaagatc aaaggatctt cttgagatcc ttttttttctg cgcgtaatct gctgcttgca   9120
aacaaaaaaa ccaccgctac cagcggtggt ttgtttgccg gatcaagagc taccaactct   9180
ttttccgaag gtaactggct tcagcagagc gcagatacca aatactgttc ttctagtgta   9240
gccgtagtta ggccaccact tcaagaactc tgtagcaccg cctacatacc tcgctctgct   9300
aatcctgtta ccagtggctg ctgccagtgg cgataagtcg tgtcttaccg ggttggactc   9360
aagacgatag ttaccggata aggcgcagcg gtcgggctga acggggggtt cgtgcacaca   9420
gcccagcttg gagcgaacga cctacaccga actgagatac ctacagcgtg agctatgaga   9480
aagcgccacg cttcccgaag ggagaaaggc ggacaggtat ccggtaagcg cagggtcgg    9540
aacaggagag cgcacgaggg agcttccagg gggaaacgcc tggtatcttt atagtcctgt   9600
cgggtttcgc cacctctgac ttgagcgtcg atttttgtga tgctcgtcag gggggcggag   9660
cctatggaaa aacgccagca acgcggcctt tttacggttc ctggcctttt gctggccttt   9720
tgctcacatg ttctttcctg cgttatcccc tgattctgtg gataaccgta ttaccgcctt   9780
tgagtgagct gataccgctc gccgcagccg aacgaccgag cgcagcgagt cagtgagcga   9840
ggaagcggaa gagcgcccaa tacgcaaacc gcctctcccc gcgcgttggc cgattcatta   9900
atgcagctgt ggaatgtgtg tcagttaggg tgtggaaagt ccccaggctc cccagcaggc   9960
agaagtatgc aaagcatgca tctcaattag tcagcaacca ggtgtggaaa gtccccaggc  10020
tccccagcag gcagaagtat gcaaagcatg catctcaatt agtcagcaac catagtcccg  10080
```

```
ccctaactc cgcccatccc gcccctaact ccgcccagtt ccgcccattc tccgcccat     10140
ggctgactaa ttttttttat ttatgcagag gccgaggccg cctcggcctc tgagctattc   10200
cagaagtagt gaggaggctt ttttggaggc ctaggctttt gcaaaaagct tggacacaag   10260
acaggcttgc gagatatgtt tgagaatacc actttatccc gcgtcaggga gaggcagtgc   10320
gtaaaaagac gcggactcat gtgaaatact ggttttagt gcgccagatc tctataatct   10380
cgcgcaacct attttcccct cgaacactt ttaagccgta gataaacagg ctgggacact   10440
tcacatgagc gaaaaataca tcgtcacctg ggacatgttg cagatccatg cacgtaaact   10500
cgcaagccga ctgatgcctt ctgaacaatg gaaaggcatt attgccgtaa gccgtggcgg   10560
tctgtaccgg gtgcgttact ggcgcgtgaa ctgggtattc gtcatgtcga taccgtttgt   10620
atttccagct acgatcacga caaccagcgc gagcttaaag tgctgaaacg cgcagaaggc   10680
gatggcgaag gcttcatcgt tattgatgac ctggtggata ccggtggtac tgcggttgcg   10740
attcgtgaaa tgtatccaaa agcgcacttt gtcaccatct tcgcaaaacc ggctggtcgt   10800
ccgctggttg atgactatgt tgttgatatc ccgcaagata cctggattga acagccgtgg   10860
gatatgggcg tcgtattcgt cccgccaatc tccggtcgct aatcttttca acgcctggca   10920
ctgccgggcg ttgttctttt taacttcagg cgggttacaa tagtttccag taagtattct   10980
ggaggctgca tccatgacac aggcaaacct gagcgaaacc ctgttcaaac cccgctttaa   11040
acatcctgaa acctcgacgc tagtccgccg ctttaatcac ggcgcacaac cgcctgtgca   11100
gtcggccctt gatggtaaaa ccatccctca ctggtatcgc atgattaacc gtctgatgtg   11160
gatctggcgc ggcattgacc cacgcgaaat cctcgacgtc caggcacgta ttgtgatgag   11220
cgatgccgaa cgtaccgacg atgatttata cgatacggtg attggctacc gtggcggcaa   11280
ctggatttat gagtgggccc cggatctttg tgaaggaacc ttacttctgt ggtgtgacat   11340
aattggacaa actacctaca gagatttaaa gctctaaggt aaatataaaa tttttaaccc   11400
ggatctttgt gaaggaacct tacttctgtg gtgtgacata attggacaaa ctacctacag   11460
agatttaaag ctctaaggta aatataaaat ttttaagtgt ataatgtgtt aaactactga   11520
ttctaattgt ttgtgtattt tagattccaa cctatggaac tgatgaatgg gagcagtggt   11580
ggaatgcctt taatgaggaa aacctgtttt gctcagaaga aatgccatct agtgatgatg   11640
aggctactgc tgactctcaa cattctactc ctccaaaaaa gaagagaaag gtagaagacc   11700
ccaaggactt tccttcagaa ttgctaagtt ttttgagtca tgctgtgttt agtaatagaa   11760
ctcttgcttg ctttgctatt tacaccacaa aggaaaaagc tgcactgcta tacaagaaaa   11820
ttatggaaaa atattctgta acctttataa gtaggcataa cagttataat cataacatac   11880
tgttttttct tactccacac aggcatagag tgtctgctat taataactat gctcaaaaat   11940
tgtgtacctt tagcttttta atttgtaaag gggttaataa ggaatatttg atgtatagtg   12000
ccttgactag agatcataat cagccatacc acatttgtag aggttttact tgctttaaaa   12060
aacctcccac acctcccct gaacctgaaa cataaaatga atgcaattgt tgttgttggg   12120
ctgcaggaat taattcgagc tcgcccgaca                                    12150
```

UREA COMPOUNDS AND COMPOSITIONS AS SMARCA2/BRM ATPASE INHIBITORS

SEQUENCE LISTING

The instant application contains a Sequence Listing which has been submitted electronically in XML format and is hereby incorporated by reference in its entirety. Said XML copy, created on Mar. 11, 2024, is named PAT057524-US-CNT SL.xml and is 29,998 bytes in size.

FIELD OF THE INVENTION

The present disclosure relates to compounds, compositions comprising such compounds, and their use for the treatment of BRM-mediated and/or BRG1-mediated disorders or diseases including BRG1/SMARCA4-mutant cancers.

BACKGROUND OF THE INVENTION

The mammalian SWI/SNF (mSWI/SNF) multi-protein complexes regulate chromatin structure through ATP-dependent nucleosome remodeling and thereby control many key cellular processes. Several subunits of the mSWI/SNF complexes have roles as tumor suppressors, and recent genomic studies revealed recurrent mutations in several of these subunits, with a collective mutation frequency of approximately 20% across all cancers. The catalytic SWI/SNF subunit BRG1, also known as SMARCA4, is frequently mutated in lung adenocarcinomas and other cancer types.

BRM (also known as SMARCA2) is the paralog of BRG1 (or BRM/SWI2-related gene 1, also known as SMARCA4), and these two proteins function as mutually exclusive ATP-dependent subunits within the mammalian SWI/SNF chromatin remodeling complex. Either BRM or BRG1 is required for cells to assemble a catalytically active SWI/SNF complex. Multiple variants of the SWI/SNF complex have been characterized with differing subunit composition, but only one catalytic subunit (BRM or BRG1) is present in each complex.

BRG1 has been shown to function as a tumor suppressor and is significantly mutated in human cancers. Evidence for the tumor suppressive function of BRG1 has been demonstrated by re-expression of wild type BRG1 in BRG1-mutant cell lines, resulting in differentiation and cell cycle arrest. Brg1+/− mice develop mammary carcinoma with a 10% incidence in one year. Loss-of-function mutations in BRG1 have been identified in ~30% of established non-small-cell lung cancer lines, and silencing of BRG1 is found in many other cancer cell lines and tumor samples, including lung, pancreatic, and ovarian cancers, melanomas, and pediatric rhabdoid sarcomas. Importantly, recent results from the Cancer Genome Atlas (TCGA) project identified BRG1 mutations as a prominently mutated gene in tumor samples from patients with lung adenocarcinoma, occurring in ~10% of all tumor samples (a rate similar to other well characterized oncogenes and tumor suppressors such as EGFR and LKB1). The TCGA project has likewise identified BRM mutations and deletions in various cancers including that from lung.

Insights into therapeutic targeting of SWI/SNF mutant cancers have come from studies showing that residual SWI/SNF complexes play a role in the survival of cancers with SWI/SNF mutations. In particular, a synthetic lethal relationship was discovered between BRM and BRG1, the two ATPases of the complex, whereby loss of one leads to a dependency on the other. For example, BRM depletion was demonstrated to induce growth inhibition in BRG1-mutant cancer cells. Additionally, other studies have shown that SNF5-deficient tumor cells (SNF5 is a subunit of the SWI/SNF complex) are dependent on BRG1. Finally, certain cancers lacking SWI/SNF mutations have also been reported to be sensitive to BRG1 inhibition such as in acute myeloid leukemia (AML). Hence, the inhibition of certain SWI/SNF subunits, including BRG1 and BRM, presents opportunities for the development of novel therapeutic agents for the treatment of human diseases, including cancers.

SUMMARY OF THE INVENTION

There remains a need for new treatments and therapies for BRM-mediated and/or BRG1-mediated disorders or diseases. The present disclosure provides compounds, pharmaceutically acceptable salts thereof, pharmaceutical compositions thereof and combinations thereof, which compounds are BRM and/or BRG1 inhibitors. The present disclosure further provides method of treating BRM-mediated and/or BRG1-mediated disorders or diseases, comprising administering to a subject in need thereof an effective amount of a BRM and/or BRG1 inhibitor (e.g., compounds of the present disclosure).

One aspect of the present disclosure provides a compound of Formula (I) or a pharmaceutically acceptable salt thereof, wherein $R^1$-$R^6$ are as defined herein.

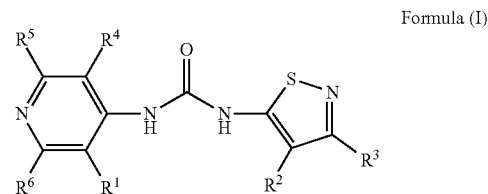

Formula (I)

Another aspect of the present disclosure provides a pharmaceutical composition comprising a therapeutically effective amount of a compound of Formula (I), or a pharmaceutically acceptable salt thereof, and one or more pharmaceutically acceptable carriers.

In yet another aspect of the present disclosure, a pharmaceutical combination is provided which comprises a therapeutically effective amount of a compound of Formula (I), or a pharmaceutically acceptable salt thereof, and one or more therapeutically active agents.

In yet another aspect of the present disclosure, a method is provided for treating BRM-mediated and/or BRG1-mediated disorders or diseases, which comprises administering to a subject in need thereof a therapeutically effective amount of a compound of Formula (I), or a pharmaceutically acceptable salt thereof.

In yet another aspect of the present disclosure, processes are provided for preparing compounds of Formula (I), or a pharmaceutically acceptable salt thereof.

DETAILED DESCRIPTION

Various (enumerated) embodiments of the disclosure are described herein. It will be recognized that features specified in each embodiment may be combined with other specified features to provide further embodiments of the present disclosure.

Embodiment 1: A compound of Formula (I)

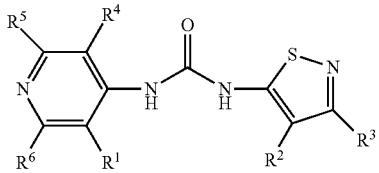

Formula (I)

or a pharmaceutically acceptable salt thereof, in which: $R^1$ is selected from hydrogen, amino and hydroxy-substituted $C_{1-2}$alkyl; $R^2$ is hydrogen; $R^3$ is selected from $C_{1-2}$alkyl and halo-substituted-$C_{1-2}$alkyl; $R^4$ is hydrogen; $R^5$ is selected from hydrogen and halo; and $R^6$ is selected from hydrogen and halo.

Embodiment 2: A compound or a pharmaceutically acceptable salt thereof according to Embodiment 1, in which: $R^1$ is selected from hydrogen, amino and hydroxy-methyl; $R^2$ is hydrogen; $R^3$ is selected from methyl, difluoromethyl and trifluoromethyl; $R^4$ is hydrogen; $R^5$ is selected from hydrogen, chloro and fluoro; and $R^6$ is selected from hydrogen and fluoro.

Embodiment 3: A compound or a pharmaceutically acceptable salt thereof according to Embodiment 1 selected from:

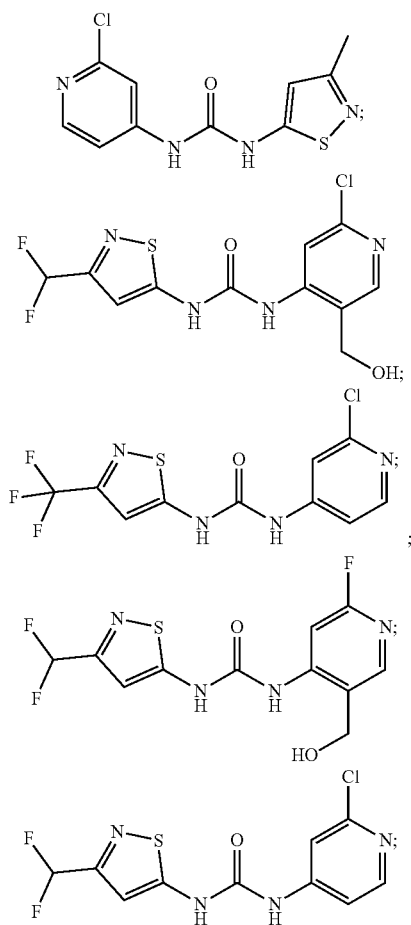

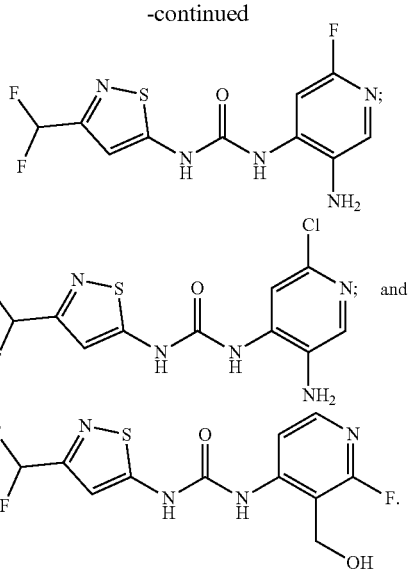

Embodiment 4: A pharmaceutical composition, comprising a therapeutically effective amount of a compound of according to any one of Embodiments 1 to 3 or a pharmaceutically acceptable salt thereof, and one or more pharmaceutically acceptable carriers.

Embodiment 5: A pharmaceutical combination, comprising a therapeutically effective amount of a compound according to any one of Embodiments 1 to 4 or a pharmaceutically acceptable salt thereof, and one or more therapeutically active agents.

Embodiment 6: A pharmaceutical combination according to Embodiment 5, where said one or more therapeutically active agents are independently selected from anti-cancer agents, anti-allergic agents, anti-emetics, pain relievers, immunomodulators and cytoprotective agents.

Embodiment 7: A method of treating a BRM-mediated and/or a BRG1-mediated disorder or disease, comprising administering to a subject in need thereof a therapeutically effective amount of a compound according to any one of Embodiments 1 to 27 or a pharmaceutically acceptable salt thereof.

Embodiment 8: A method according to Embodiment 7, wherein said disorder or disease is malignancy which is characterized by BRG1-deficiency and/or BRM-deficiency.

Embodiment 9: A method according to Embodiment 7 or 8, wherein said disorder or disease is malignancy which is characterized by BRG1 mutation and/or BRM mutation.

Embodiment 10: A method according to any one of Embodiments 7-9, wherein said disorder or disease is solid tumor, leukemia or lymphoma.

Embodiment 11: A method according to any one of Embodiments 7-10, wherein said disorder or disease is selected from the group consisting of non-small cell lung carcinoma, lung adenocarcinoma, lung carcinoma, large cell lung carcinomas, non-small cell lung carcinoma, lung squamous cell carcinoma, small cell lung cancer, skin cutaneous melanoma, desmoplastic melanoma, uveal melanoma, small cell carcinoma of the ovary (hypercalcemic type), ovarian rhabdoid tumor, cutaneous squamous cell carcinoma, glioma, uterine carcinosarcoma, uterine corpus endometrial carcinoma, ovarian serous cystadenocarcinoma, bladder urothelial carcinoma, primary central nervous system lymphoma, esophageal carcinoma, bladder cancer, bladder cancer plasmacytoid variant, stomach adenocarcinoma, adenoid cystic carcinoma, lymphoid neoplasm diffuse large B-cell lymphoma, pancreatic cancer, colorectal adenocarcinoma, cholangiocarcinoma, sarcoma, head and neck cancers, cervical and endocervical cancers, medulloblastoma, cutaneous T cell lymphoma, liver hepatocellular carcinoma, kidney renal papillary cell carcinoma, breast cancer, mantle cell lymphoma, gallbladder carcinoma, testicular germ cell cancers, kidney renal cell clear cell carcinoma, prostate cancer, pediatric ewing sarcoma, thymoma, kidney chromophobe, renal non-clear cell carcinoma, pheochromocytoma and paraganglioma, thyroid cancers, malignant peripheral nerve sheath tumor, neuroendocrine prostate cancer, head and neck squamous cell carcinoma, adrenocortical carcinoma, cervical and endocervical cancers, cutaneous squamous cell carcinoma, testicular germ cell cancer, glioblastoma, glioblastoma multiforme, Ewing's sarcoma, clear cell renal cell carcinoma, neuroblastoma, diffuse large B cell lymphoma, acute myeloid leukemia, chronic lymphocytic leukemia, multiple myeloma, malignant rhabdoid tumors, epithelioid sarcomas, familial schwannomatosis, renal medullary carcinomas, synovial sarcoma, and meningiomas.

Embodiment 12: A method according to any one of Embodiments 7-11, wherein said disorder or disease is selected from the group consisting of non-small cell lung carcinoma, lung adenocarcinoma, lung carcinoma, large cell lung carcinomas, non-small cell lung carcinoma, lung squamous cell carcinoma, small cell lung cancer, skin cutaneous melanoma, desmoplastic melanoma and uveal melanoma.

Embodiment 13: A method according to Embodiment 7 or 8, wherein said disorder or disease is malignancy which is characterized by BRG1-deficiency.

Embodiment 14: A method according to any one of Embodiments 7, 8 or 13, wherein said disorder or disease is malignancy which is characterized by BRG1 mutation.

Embodiment 15: A method according to any one of Embodiments 7, 8, 13 and 14, wherein said disorder or disease is selected from the group consisting of non-small cell lung carcinoma, lung adenocarcinoma, lung carcinoma, large cell lung carcinomas, non-small cell lung carcinoma, lung squamous cell carcinoma, small cell lung cancer, skin cutaneous melanoma, desmoplastic melanoma, uveal melanoma, small cell carcinoma of the ovary, cutaneous squamous cell carcinoma, glioma, uterine carcinosarcoma, uterine corpus endometrial carcinoma, ovarian serous cystadenocarcinoma, bladder urothelial carcinoma, primary central nervous system lymphoma, esophageal carcinoma, bladder cancer, bladder cancer plasmacytoid variant, stomach adenocarcinoma, adenoid cystic carcinoma, lymphoid neoplasm diffuse large B-cell lymphoma, pancreatic cancer, colorectal adenocarcinoma, cholangiocarcinoma, sarcoma, head and neck cancers, cervical and endocervical cancers, medulloblastoma, cutaneous T cell lymphoma, liver hepatocellular carcinoma, kidney renal papillary cell carcinoma, breast cancer, mantle cell lymphoma, gallbladder carcinoma, testicular germ cell cancers, kidney renal cell clear cell carcinoma, prostate cancer, pediatric ewing sarcoma, thymoma, kidney chromophobe, renal non-clear cell carcinoma, pheochromocytoma and paraganglioma and thyroid cancers.

Embodiment 16: A method according to any one of Embodiments 7, 8 and 13-15, wherein said disorder or disease is selected from the group consisting of non-small cell lung carcinoma, lung adenocarcinoma, lung carcinoma, large cell lung carcinomas, non-small cell lung carcinoma, lung squamous cell carcinoma, small cell lung cancer, skin cutaneous melanoma, desmoplastic melanoma and uveal melanoma.

Embodiment 17: A method according to Embodiment 7 or 8, wherein said disorder or disease is malignancy which is characterized by BRM-deficiency.

Embodiment 18: A method according to any one of Embodiments 7, 8 and 17, wherein said disorder or disease is malignancy which is characterized by BRM mutation.

Embodiment 19: A method according to any one of Embodiments 7, 8 and 17-18, wherein said disorder or disease is selected from the group consisting of malignant peripheral nerve sheath tumor, neuroendocrine prostate cancer, breast cancer, bladder urothelial carcinoma, adenoid cystic carcinoma, stomach adenocarcinoma, breast carcinomas, ovarian serous cystadenocarcinoma, uterine carcinosarcoma, esophageal carcinoma, head and neck squamous cell carcinoma, non-small cell lung carcinomas, lung adenocarcinoma, lung squamous cell carcinoma, small cell lung cancer, pancreatic cancer, adrenocortical carcinoma, skin cutaneous melanoma, sarcoma, colorectal adenocarcinoma, cervical and endocervical cancers, liver hepatocellular carcinoma, cutaneous squamous cell carcinoma, testicular germ cell cancer, glioblastoma, glioblastoma multiforme, cholangiocarcinoma, Ewing's sarcoma, clear cell renal cell carcinoma, neuroblastoma, acute myeloid leukemia and diffuse large B-cell lymphoma.

Embodiment 20: A method according to any one of Embodiments 7-8 and 17-19, wherein said disorder or disease is selected from the group consisting of non-small cell lung carcinoma, lung adenocarcinoma, lung carcinoma, large cell lung carcinomas, non-small cell lung carcinoma, lung squamous cell carcinoma, small cell lung cancer, skin cutaneous melanoma, desmoplastic melanoma and uveal melanoma.

Embodiment 21: A method according to Embodiment 7, wherein said disorder or disease is malignancy which is characterized by mutations in SWI/SNF subunits other than BRM or BRG1.

Embodiment 22: A method according to Embodiment 7 or 21, wherein said disorder or disease is solid tumor, leukemia or lymphoma.

Embodiment 23: A method according to any one of Embodiments 7, 21 and 22, wherein said disorder or disease is selected from the group consisting of malignant rhabdoid tumors (characterized by deficiency in SNF5/SMARCB1), epithelioid sarcomas, familial schwannomatosis, renal medullary carcinomas, Ewing sarcomas, synovial sarcoma, uterine corpus endometrial carcinoma, stomach adenocarcinoma, bladder urothelial carcinoma, bladder cancer, adenoid cystic carcinoma, cholangiocarcinoma, desmoplastic melanoma, cutaneous squamous cell carcinoma, pancreatic cancer, liver hepatocellular carcinoma, melanoma, diffuse large B-cell lymphoma, breast cancers, colorectal cancer, ovarian clear cell carcinoma, neuroblastoma, esophageal carcinoma, lung cancers, kidney renal clear cell carcinoma, mesothelioma, adenoid cystic carcinoma of the breast, adenoid cystic carcinoma, thyroid cancers, meningiomas, uveal melanomas and acute myeloid leukemias.

Embodiment 24: A method according to any one of Embodiments 7, 21, 22 and 23, wherein said disorder or disease is selected from the group consisting of malignant rhabdoid tumors, breast cancers, pancreatic cancers, ovarian cancers, ovarian clear cell carcinomas, bladder cancers, renal clear cell carcinomas, colorectal cancer, gastric cancers, liver cancer, melanoma, glioma, acute myeloid leukemia and lung cancers.

Embodiment 25: A compound according to any one of the Embodiments 1-3, or a pharmaceutically acceptable salt thereof, for use as a medicament.

Other features of the present disclosure should become apparent in the course of the above descriptions of exemplary embodiments that are given for illustration of the disclosure and are not intended to be limiting thereof.

Definitions

For purposes of interpreting this specification, the following definitions will apply, and whenever appropriate, terms used in the singular will also include the plural. Terms used in the specification have the following meanings unless the context clearly indicates otherwise.

All methods described herein can be performed in any suitable order unless otherwise indicated herein or otherwise clearly contradicted by context. The use of any and all examples, or exemplary language (e.g. "such as") provided herein is intended merely to better illuminate the present disclosure and does not pose a limitation on the scope of the present disclosure otherwise claimed.

The term "a," "an," "the" and similar terms used in the context of the present disclosure (especially in the context of the claims) are to be construed to cover both the singular and plural unless otherwise indicated herein or clearly contradicted by the context.

As used herein, the terms "alkyl" refers to a hydrocarbon radical of the general formula $C_nH_{2n+1}$. The alkane radical may be straight or branched. For example, the term "$C_1$-$C_6$ alkyl" or "$C_1$ to $C_6$ alkyl" refers to a monovalent, straight, or branched aliphatic group containing 1 to 6 carbon atoms (e.g., methyl, ethyl, n-propyl, i-propyl, n-butyl, i-butyl, s-butyl, t-butyl, n-pentyl, 1-methylbutyl, 2-methylbutyl, 3-methylbutyl, neopentyl, 3,3-dimethylpropyl, hexyl, 2-methylpentyl, and the like). When an alkyl is substituted with one more substituents, the substitutents can be substituted on any carbon atoms of the alkyl.

"Halogen" or "halo" may be fluorine, chlorine, bromine or iodine (preferred halogens as substituents are fluorine and chlorine).

"Haloalkyl" is intended to include both branched and straight-chain saturated aliphatic hydrocarbon groups having the specified number of carbon atoms, substituted with one or more halogens. Thus, "$C_1$-$C_6$ haloalkyl" or "$C_1$ to $C_6$ haloalkyl" is intended to include, but not limited to, fluoromethyl, difluoromethyl, trifluoromethyl, trichloromethyl, pentafluoroethyl, pentachloroethyl, 2,2,2-trifluoroethyl, heptafluoropropyl, and heptachloropropyl.

As referred to herein, the term "substituted" means that at least one hydrogen atom is replaced with a non-hydrogen group, provided that normal valencies are maintained and that the substitution results in a stable compound. When a substituent is keto (i.e., =O), then 2 hydrogens on the atom are replaced. Keto substituents are not present on aromatic moieties.

The phrase "pharmaceutically acceptable" indicates that the substance or composition must be compatible chemically and/or toxicologically, with the other ingredients comprising a formulation, and/or the mammal being treated therewith.

Unless specified otherwise, the term "compounds of the present disclosure" refers to compounds of Formula (I) as well as isomers, such as stereoisomers (including diastereoisomers, enantiomers and racemates), geometrical isomers, conformational isomers (including rotamers and astropisomers), tautomers, isotopically labeled compounds (including deuterium substitutions), and inherently formed moieties (e.g., polymorphs, solvates and/or hydrates). When a moiety is present that is capable of forming a salt, then salts are included as well, in particular pharmaceutically acceptable salts.

Depending on the process conditions the end products of the present disclosure are obtained either in free (neutral) or salt form. Both the free form and the salts of these end products are within the scope of the present disclosure. If so desired, one form of a compound may be converted into another form. A free base or acid may be converted into a salt; a salt may be converted into the free compound or another salt; a mixture of isomeric compounds of the present disclosure may be separated into the individual isomers.

Pharmaceutically acceptable salts are preferred. However, other salts may be useful, e.g., in isolation or purification steps which may be employed during preparation, and thus, are contemplated within the scope of the present disclosure.

As used herein, "pharmaceutically acceptable salts" refer to derivatives of the disclosed compounds wherein the parent compound is modified by making acid or base salts thereof. For example, pharmaceutically acceptable salts include, but are not limited to, acetate, ascorbate, adipate, aspartate, benzoate, besylate, bromide/hydrobromide, bicarbonate/carbonate, bisulfate/sulfate, camphorsulfonate, caprate, chloride/hydrochloride, chlortheophyllonate, citrate, ethandisulfonate, fumarate, gluceptate, gluconate, glucuronate, glutamate, glutarate, glycolate, hippurate, hydroiodide/iodide, isethionate, lactate, lactobionate, laurylsulfate, malate, maleate, malonate/hydroxymalonate, mandelate, mesylate, methylsulphate, mucate, naphthoate, napsylate, nicotinate, nitrate, octadecanoate, oleate, oxalate, palmitate, pamoate, phenylacetate, phosphate/hydrogen phosphate/dihydrogen phosphate, polygalacturonate, propionate, salicylates, stearate, succinate, sulfamate, sulfosalicylate, tartrate, tosylate, trifluoroacetate or xinafoate salt form.

Pharmaceutically acceptable acid addition salts can be formed with inorganic acids and organic acids. Inorganic acids from which salts can be derived include, for example, hydrochloric acid, hydrobromic acid, sulfuric acid, nitric acid, phosphoric acid, and the like. Organic acids from which salts can be derived include, for example, acetic acid, propionic acid, glycolic acid, oxalic acid, maleic acid, malonic acid, succinic acid, fumaric acid, tartaric acid, citric acid, benzoic acid, mandelic acid, methanesulfonic acid, ethanesulfonic acid, toluenesulfonic acid, sulfosalicylic acid, and the like.

Pharmaceutically acceptable base addition salts can be formed with inorganic and organic bases. Inorganic bases from which salts can be derived include, for example, ammonium salts and metals from columns I to XII of the periodic table. In certain embodiments, the salts are derived from sodium, potassium, ammonium, calcium, magnesium, iron, silver, zinc, and copper; particularly suitable salts include ammonium, potassium, sodium, calcium and magnesium salts. Organic bases from which salts can be derived include, for example, primary, secondary, and tertiary amines, substituted amines including naturally occurring substituted amines, cyclic amines, basic ion exchange resins, and the like. Certain organic amines include isopropylamine, benzathine, cholinate, diethanolamine, diethylamine, lysine, meglumine, piperazine and tromethamine.

The pharmaceutically acceptable salts of the present disclosure can be synthesized from the parent compound that contains a basic or acidic moiety by conventional chemical methods. Generally, such salts can be prepared by reacting the free acid or base forms of these compounds with a stoichiometric amount of the appropriate base or acid in water or in an organic solvent, or in a mixture of the two; generally, nonaqueous media like ether, ethyl acetate, ethanol, isopropanol, or acetonitrile are preferred. Lists of suitable salts are found in Allen, L. V., Jr., ed., *Remington: The Science and Practice of Pharmacy*, 22nd Edition, Pharmaceutical Press, London, UK (2012), the disclosure of which is hereby incorporated by reference.

Compounds of the present disclosure that contain groups capable of acting as donors and/or acceptors for hydrogen bonds may be capable of forming co-crystals with suitable co-crystal formers. These co-crystals may be prepared from compounds of the present disclosure by known co-crystal forming procedures. Such procedures include grinding, heating, co-subliming, co-melting, or contacting in solution compounds of the present disclosure with the co-crystal former under crystallization conditions and isolating co-crystals thereby formed. Suitable co-crystal formers include those described in WO 2004/078163. Hence the present disclosure further provides co-crystals comprising a compound of the present disclosure.

Any formula given herein is also intended to represent unlabeled forms as well as isotopically labeled forms of the compounds. Isotopically labeled compounds have structures depicted by the formulas given herein except that one or more atoms are replaced by an atom having a selected atomic mass or mass number. Examples of isotopes that can be incorporated into compounds of the present disclosure include isotopes of hydrogen, carbon, nitrogen, oxygen, phosphorous, fluorine, chlorine and iodine such as $^2H$, $^3H$, $^{11}C$, $^{13}C$, $^{14}C$, $^{15}N$, $^{18}F$, $^{31}P$, $^{32}P$, $^{35}S$, $^{36}Cl$, $^{123}I$, $^{124}I$, $^{125}I$ respectively. The present disclosure includes various isotopically labeled compounds as defined herein, for example those into which radioactive isotopes, such as $^3H$ and $^{14}C$, or those into which non-radioactive isotopes, such as $^2H$ and $^{13}C$ are present. Such isotopically labelled compounds are useful in metabolic studies (with $^{14}C$), reaction kinetic studies (with, for example $^2H$ or $^3H$), detection or imaging techniques, such as positron emission tomography (PET) or single-photon emission computed tomography (SPECT) including drug or substrate tissue distribution assays, or in radioactive treatment of patients. In particular, an $^{18}F$ or labeled compound may be particularly desirable for PET or SPECT studies.

Further, substitution with heavier isotopes, particularly deuterium (i.e., $^2H$ or D) may afford certain therapeutic advantages resulting from greater metabolic stability, for example increased in vivo half-life or reduced dosage requirements or an improvement in therapeutic index. It is understood that deuterium in this context is regarded as a substituent of a compound of the present disclosure. The concentration of such a heavier isotope, specifically deuterium, may be defined by the isotopic enrichment factor. The term "isotopic enrichment factor" as used herein means the ratio between the isotopic abundance and the natural abundance of a specified isotope. If a substituent in a compound of this present disclosure is denoted deuterium, such compound has an isotopic enrichment factor for each designated deuterium atom of at least 3500 (52.5% deuterium incorporation at each designated deuterium atom), at least 4000 (60% deuterium incorporation), at least 4500 (67.5% deuterium incorporation), at least 5000 (75% deuterium incorporation), at least 5500 (82.5% deuterium incorporation), at least 6000 (90% deuterium incorporation), at least 6333.3 (95% deuterium incorporation), at least 6466.7 (97% deuterium incorporation), at least 6600 (99% deuterium incorporation), or at least 6633.3 (99.5% deuterium incorporation).

For example, a deuterated compound of the invention can be:

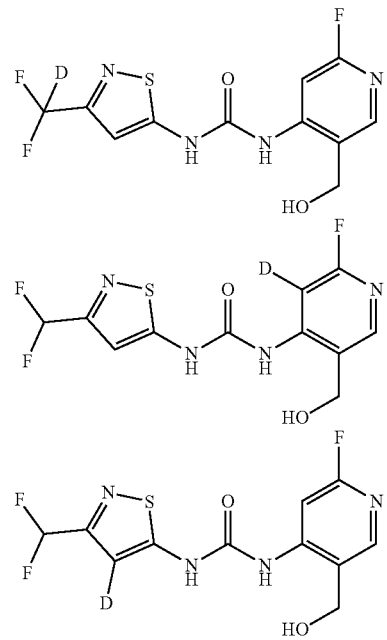

Isotopically labeled compounds of this present disclosure can generally be prepared by conventional techniques known to those skilled in the art or by processes disclosed in the schemes or in the examples and preparations described below (or analogous process to those described herein), by substituting an appropriate or readily available isotopically labeled reagent for a non-isotopically labeled reagent otherwise employed. Such compounds have a variety of potential uses, e.g., as standards and reagents in determining the ability of a potential pharmaceutical compound to bind to target proteins or receptors, or for imaging compounds of this disclosure bound to biological receptors in vivo or in vitro.

The term "solvate" means a physical association of a compound of this disclosure with one or more solvent molecules, whether organic or inorganic. This physical association includes hydrogen bonding. In certain instances the solvate will be capable of isolation, for example when one or more solvent molecules are incorporated in the crystal lattice of the crystalline solid. The solvent molecules in the solvate may be present in a regular arrangement and/or a non-ordered arrangement. The solvate may comprise either a stoichiometric or nonstoichiometric amount of the solvent molecules. "Solvate" encompasses both solution-phase and isolable solvates. Exemplary solvates include, but are not limited to, hydrates, ethanolates, methanolates, and isopropanolates. Methods of solvation are generally known in the art.

As used herein, "polymorph(s)" refer to crystalline form (s) having the same chemical structure/composition but different spatial arrangements of the molecules and/or ions forming the crystals. Compounds of the present disclosure can be provided as amorphous solids or crystalline solids. Lyophilization can be employed to provide the compounds of the present disclosure as a solid.

"BRM" and "BRG1" refer to two paralogs of the ATPase subunit in the SWI/SNF complex, also known as SMARCA2 and SMARCA4, respectively. Unless specifically stated otherwise, BRM, as used herein, refers to human BRM (Entrez Gene 6595), whose protein sequence has Swiss-Prot accession number P51531.2; and BRG1, as used herein, refers to human BRG1 (Entrez Gene 6597), whose protein sequence has Swiss-Prot: accession numbers P51532.2. BRM, BRG1, and the SWI/SNF complex is described in detail in such reviews as Wilson, B G, et al. Nat Rev Cancer. 2011 Jun. 9; 11(7):481-92. The BRG1 (SMARCA4) genomic sequence has NCBI Reference Sequence: NG_011556.1; its mRNAs result from a variety of splice forms (i.e., transcript variants), including NCBI Reference numbers NM_001128844.1, NM_001128849.1, NM_001128845.1, NM_001128846.1, NM_001128847.1, NM_001128848.1, and NM_003072.3. The BRM (SMARCA2) genomic sequence has NCBI Reference Sequence: NC_000009.11, it's mRNAs result from two splice forms (i.e., transcript variants), including NCBI Reference numbers NM_003070.3 and NM_139045.2.

The term "BRM mediated disorder or disease" refers to any disorder or disease which is directly or indirectly regulated by BRM. The term "BRG1 mediated disorder or disease" refers to any disorder or disease which is directly or indirectly regulated by BRG1. A BRM mediated or BRG1 mediated disorder or disease may be characterized by BRG1 deficiency and/or BRM deficiency. A BRM mediated or BRG1 mediated disorder or disease may be characterized by mutations in SWI/SNF subunits other than BRM/SMARCA2 or BRG1/SMARCA4, e.g., mutations in ARID1A, ARID1B, ARID2, PBRM1, SMARCB1/SNF5, SMARCE1, SMARCC1, SMARCC2, PHF10, DPF1, DPF3, DPF2, ACTL6A, ACTL6B, SMARCD2, SMARCD3, SMARCD1, BCL11A, BCL11B, BCL7A, BCL7B, BCL7C, BRD9, BRD7, SS18 and ACTB. A BRM mediated or BRG1 mediated disorder or disease may be characterized by dependency on BRM, BRG1 or other SWI/SNF subunits as described above where said dependency is not related to mutations of BRM, BRG1 or other SWI/SNF subunits.

The terms "BRG1 deficient" and "BRG1 deficiency" refer to cells (including, but not limited to, cancer cells, cell lines, tissues, tissue types, tumors, etc.) that have mutation or deletion of the BRG1 gene, or have a significant reduction in production, expression, level, stability and/or activity of BRG1 relative to that in a control, e.g., reference or normal or non-cancerous cells. The reduction can be at least about 20%, 30%, 40%, 50%, 60%, 70%, 80% or 90%. In some embodiments, the reduction is at least 20%. In some embodiments, the reduction is at least 50%. Mutations in the BRG1 gene that lead to loss of function in which mutations may be of the type that are nonsense, insertions/deletions resulting in frameshift, or missense mutations. The BRG1 deficient cells include those wherein the BRG1 gene has been mutated or deleted.

The terms "BRM-deficient" and "BRM-deficiency" refer to cells (including, but not limited to, cancer cells, cell lines, tissues, tissue types, tumors, etc.) that have a loss-of-function ("LOF") mutation or deletion of the BRM gene, or have a significant reduction in production, expression, level, stability and/or activity of BRM relative to that in a control, e.g., reference or normal or non-cancerous cells. The reduction can be at least about 20%, 30%, 40%, 50%, 60%, 70%, 80% or 90%. In some embodiments, the reduction is at least 20%. In some embodiments, the reduction is at least 50%. The BRM deficient cells include those wherein the BRM gene has been mutated or deleted.

The term "BRG1 deficiency related disorder or disease" or "disorder or disease characterized by BRG1 deficiency" refers to a disorder or disease wherein cells are BRG1 deficient. For example, in a BRG1 deficiency related disorder or disease, one or more disease cells can have a mutation or deletion of the BRG1 gene, or have a significant reduction in production, expression, level, stability and/or activity of BRG1. In a patient afflicted with a BRG1 deficiency related disorder or disease, it is possible that some disease cells (e.g., cancer cells) can be BRG1 deficient while others are not.

The term "BRM deficiency related disorder or disease" or "disorder or disease characterized by BRM deficiency" refers to a disorder or disease wherein cells are BRM deficient. For example, in a BRM deficiency related disorder or disease, one or more disease cells can have a mutation or deletion of the BRM gene, or have a significant reduction in production, expression, level, stability and/or activity of BRM. In a patient afflicted with a BRM deficiency related disorder or disease, it is possible that some disease cells (e.g., cancer cells) can be BRM deficient while others are not.

The term "malignancy", also called cancer, refers to diseases in which abnormal cells divide without control and can invade nearby tissues. Malignant cells can also spread to other parts of the body through the blood and lymph systems. There are several main types of malignancy. Carcinoma is a malignancy that begins in the skin or in tissues that line or cover internal organs. Sarcoma is a malignancy that begins in bone, cartilage, fat, muscle, blood vessels, or other connective or supportive tissue. Leukemia is a malignancy that starts in blood-forming tissue, such as the bone marrow, and causes large numbers of abnormal blood cells to be produced and enter the blood. Lymphoma and multiple myeloma are malignancies that begin in the cells of the immune system. Central nervous system cancers are malignancies that begin in the tissues of the brain and spinal cord.

The term "solid tumor" refers to malignancies/cancers formed of abnormal masses of tissue that usually do not contain cysts or liquid areas. Solid tumors are named/classified according to the tissue/cells of origin. Examples include, but are not limited to, sarcomas and carcinomas.

The term "leukemia" refers to hematologic or blood cell malignancies/cancers that begin in blood-forming tissue, such as the bone marrow. Examples include, but are not limited to, acute myeloid leukemia (AML), chronic myeloid leukemia (CML), acute lymphocytic leukemia (ALL) and chronic lymphocytic leukemia (CLL).

The term "lymphoma" refers to lymphatic cell malignancies/cancers that begin in the cells of the immune system. Examples include, but are not limited to, Non-Hodgkin Lymphoma and Multiple Myeloma.

As used herein, the term "patient" encompasses all mammalian species.

As used herein, the term "subject" refers to an animal. Typically the animal is a mammal. A subject also refers to for example, primates (e.g., humans), cows, sheep, goats, horses, dogs, cats, rabbits, rats, mice, fish, birds and the like. In certain embodiments, the subject is a primate. In yet other embodiments, the subject is a human. Exemplary subjects include human beings of any age with risk factors for cancer disease.

As used herein, a subject is "in need of" a treatment if such subject would benefit biologically, medically or in quality of life from such treatment (preferably, a human).

As used herein, the term "inhibit", "inhibition" or "inhibiting" refers to the reduction or suppression of a given condition, symptom, or disorder, or disease, or a significant decrease in the baseline activity of a biological activity or process.

As used herein, the term "treat", "treating" or "treatment" of any disease/disorder refers the treatment of the disease/disorder in a mammal, particularly in a human, and include: (a) ameliorating the disease/disorder, (i.e., slowing or arresting or reducing the development of the disease/disorder, or at least one of the clinical symptoms thereof); (b) relieving or modulating the disease/disorder, (i.e., causing regression of the disease/disorder), either physically, (e.g., stabilization of a discernible symptom), physiologically, (e.g., stabilization of a physical parameter), or both); (c) alleviating or ameliorating at least one physical parameter including those which may not be discernible by the subject; and/or (d) preventing or delaying the onset or development or progression of the disease or disorder from occurring in a mammal, in particular, when such mammal is predisposed to the disease or disorder but has not yet been diagnosed as having it.

The term "a therapeutically effective amount" of a compound of the present disclosure refers to an amount of the compound of the present disclosure that will elicit the biological or medical response of a subject, for example, reduction or inhibition of an enzyme or a protein activity, or ameliorate symptoms, alleviate conditions, slow or delay disease progression, or prevent a disease, etc. In one non-limiting embodiment, the term "a therapeutically effective amount" refers to the amount of the compound of the present disclosure that, when administered to a subject, is effective to (1) at least partially alleviate, inhibit, prevent and/or ameliorate a condition, or a disorder or a disease mediated by BRM and/or BRG1; or (2) reducing or inhibiting the activity of BRM and/or BRG1.

In another non-limiting embodiment, the term "a therapeutically effective amount" refers to the amount of the compound of the present disclosure that, when administered to a cell, or a tissue, or a non-cellular biological material, or a medium, is effective to at least partially reducing or inhibiting the activity of BRM and/or BRG1; or at least partially reducing or inhibiting the expression of BRM and/or BRG1.

The effective amount can vary depending on such factors as the size and weight of the subject, the type of illness, or the particular compound of the present disclosure. One of ordinary skill in the art would be able to study the factors contained herein and make the determination regarding the effective amount of the compounds of the present disclosure without undue experimentation.

The regimen of administration can affect what constitutes an effective amount. The compound of the present disclosure can be administered to the subject either prior to or after the onset of a BRM and/or BRG1 mediated condition. Further, several divided dosages, as well as staggered dosages, can be administered daily or sequentially, or the dose can be continuously infused, or can be a bolus injection. Further, the dosages of the compound(s) of the present disclosure can be proportionally increased or decreased as indicated by the exigencies of the therapeutic or prophylactic situation.

Preparation of Compounds

The compounds of the present disclosure can be prepared in a number of ways known to one skilled in the art of organic synthesis in view of the methods, reaction schemes and examples provided herein. The compounds of the present disclosure can be synthesized using the methods described below, together with synthetic methods known in the art of synthetic organic chemistry, or by variations thereon as appreciated by those skilled in the art. Preferred methods include, but are not limited to, those described below. The reactions are performed in a solvent or solvent mixture appropriate to the reagents and materials employed and suitable for the transformations being effected. It will be understood by those skilled in the art of organic synthesis that the functionality present on the molecule should be consistent with the transformations proposed. This will sometimes require a judgment to modify the order of the synthetic steps or to select one particular process scheme over another in order to obtain a desired compound of the disclosure.

The starting materials are generally available from commercial sources such as Sigma Aldrich or other commercial vendors, or are prepared as described in this disclosure, or are readily prepared using methods well known to those skilled in the art (e.g., prepared by methods generally described in Louis F. Fieser and Mary Fieser, Reagents for Organic Synthesis, v. 1-19, Wiley, New York (1967-1999 ed.), Larock, R. C., *Comprehensive Organic Transformations*, $2^{nd}$-ed., Wiley-VCH Weinheim, Germany (1999), or Beilsteins Handbuch der organischen Chemie, 4, Aufl. ed. Springer-Verlag, Berlin, including supplements (also available via the Beilstein online database)).

For illustrative purposes, the reaction schemes depicted below provide potential routes for synthesizing the compounds of the present disclosure as well as key intermediates. For a more detailed description of the individual reaction steps, see the Examples section below. Those skilled in the art will appreciate that other synthetic routes may be used to synthesize the inventive compounds. Although specific starting materials and reagents are depicted in the schemes and discussed below, other starting materials and reagents can be easily substituted to provide a variety of derivatives and/or reaction conditions. In addition, many of the compounds prepared by the methods described below can be further modified in light of this disclosure using conventional chemistry well known to those skilled in the art.

In the preparation of compounds of the present disclosure, protection of remote functionality of intermediates may be necessary. The need for such protection will vary depending on the nature of the remote functionality and the conditions of the preparation methods. The need for such protection is readily determined by one skilled in the art. For a general description of protecting groups and their use, see Greene, T. W. et al., *Protecting Groups in Organic Synthesis*, 4th Ed., Wiley (2007). Protecting groups incorporated in making of the compounds of the present disclosure, such as the trityl protecting group, may be shown as one regioisomer but may also exist as a mixture of regioisomers.

The following abbreviations used herein below have the corresponding meanings: (app) apparent; (br) broad; (BSA) bovine serum albumin; (d) doublet; (dd) doublet of doublets;

(DCM) dichloromethane; (DIPEA) diisopropylethylamine; (DMF) N,N-dimethylformamide; (DMSO) dimethylsulfoxide; (ESI) electrospray ionization; (Et) ethyl; (EtOAc) ethyl acetate; (h) hour(s); (HPLC) high pressure liquid chromatography; (LAH) lithium aluminum hydride; (LCMS) liquid chromatography and mass spectrometry; (LHMDS) lithium hexamethyldisilazide; (MTBE) Methyl tert-butyl ether; (MeCN) acetonitrile; (MeOH) methanol; (MHz) mega hertz; (MS) mass spectrometry; (m) multiplet; (mg) milligram; (min) minutes; (mL) milliliter; (mmol) millimol; (m/z) mass to charge ratio; (NMR) nuclear magnetic resonance; (Ph) phenyl; (ppm) parts per million; (q) quartet; (Rt) retention time; (RT) room temperature; (s) singlet; (t) triplet; (TBDMS) t-butyldimethylsilyl; (tert) tertiary; (TFA) trifluoroacetic acid; (THF) tetrahydrofuran; (TMAF) tetramethyl ammonium fluoride: (TMS) trimethylsilyl.

LC/MS Methods Employed in Characterization of Examples

LC/MS data were recorded using Agilent 1100 HPLC systems with Waters Micromass ZQ, or Waters ACQUITY UPLC with Waters SQ detector or with Waters ACQUITY Qda detector. The methods used to acquire all LCMS data are described below.

| LCMS method 1 | |
|---|---|
| Column | Sunfire C18 3.0×30 mm, 3.5 µm |
| Column Temperature | 40° C. |
| Eluents | A: $H_2O$ containing 0.05% TFA, B: MeCN |
| Flow Rate | 2.0 mL/min |
| Gradient | 5% to 95% B in 1.7 min, 0.3 min 95% B |

| LCMS method 2 | |
|---|---|
| Column | XBridge C18 3.0×30 mm, 3.5 µm |
| Column Temperature | 40° C. |
| Eluents | A: $H_2O$ + 5 mM ammonium hydroxide, B: MeCN |
| Flow Rate | 2.0 mL/min |
| Gradient | 5% to 95% B in 1.7 min, 0.3 min 95% B |

| LCMS method 3 | |
|---|---|
| Column | AcQuity UPLC BEH C18 2.1×30 mm, 1.7 µm |
| Column Temperature | 50° C. |
| Eluents | A: 0.1% formic acid in water, B: 0.1% formic acid in MeCN |
| Flow Rate | 1.0 mL/min |
| Gradient | 2% to 98% B in 1.5 min, 0.3 min 98% B |

| LCMS method 4 | |
|---|---|
| Column | AcQuity UPLC BEH C18 2.1×30 mm, 1.7 µm |
| Column Temperature | 50° C. |
| Eluents | A: 5 mM $NH_4OH$ in water, B: 5 mM $NH_4OH$ in MeCN |
| Flow Rate | 1.0 mL/min |
| Gradient | 1% to 30% B in 1.2 min, 30% to 98% B in 0.95 min |

NMR Employed in Characterization of Examples $^1H$ NMR spectra were obtained with Bruker Fourier transform spectrometers operating at frequencies as follows: $^1H$ NMR: 400 MHz (Bruker). Spectra data are reported in the format: chemical shift (multiplicity, number of hydrogens). Chemical shifts are specified in ppm downfield of a tetramethylsilane internal standard (δ units, tetramethylsilane=0 ppm) and/or referenced to solvent peaks, which in $^1H$ NMR spectra appear at 2.50 ppm for $CD_3SOCD_3$, 3.31 ppm for $CD_3OD$, 1.94 ppm for $CD_3CN$, 4.79 ppm for $D_2O$, 5.32 ppm for $CD_2Cl_2$, and 7.26 ppm for $CDCl_3$.

Methods Employed in the Purification of the Examples

Purification of intermediates and final products was carried out via either normal, reverse phase chromatography or supercritical fluid chromatography (SFC). Normal phase chromatography was carried out using prepacked $SiO_2$ cartridges (e.g., RediSep® Rf columns from Teledyne Isco, Inc.) eluting with gradients of appropriate solvent systems (e.g., heptane and ethyl acetate; DCM and MeOH; or unless otherwise indicated). Reverse phase preparative HPLC was carried out using the methods described below:

(1) Basic method: XBridge 5 µm column, 5 mM $NH_4OH$ in acetonitrile and water.

(2) Formic acid method: XBridge 5 µm column; 0.1% formic acid in acetonitrile and water.

The above HPLC methods run a focused gradient from 15% acetonitrile to 40% acetonitrile.

General Synthetic Schemes

Schemes 1 and 2 (shown below) describe potential routes for preparing the compounds of the present disclosure which include compounds of Formula (I) wherein $R^1$-$R^6$ are as defined in the Summary of the Invention. The starting materials for the below reaction scheme are commercially available or can be prepared according to methods known to one skilled in the art or by methods disclosed herein. Compounds of Formula (I) can be made substantially optically pure by either using substantially optically pure starting material or by separation chromatography, recrystallization or other separation techniques well-known in the art. For a more detailed description, see the Example section below.

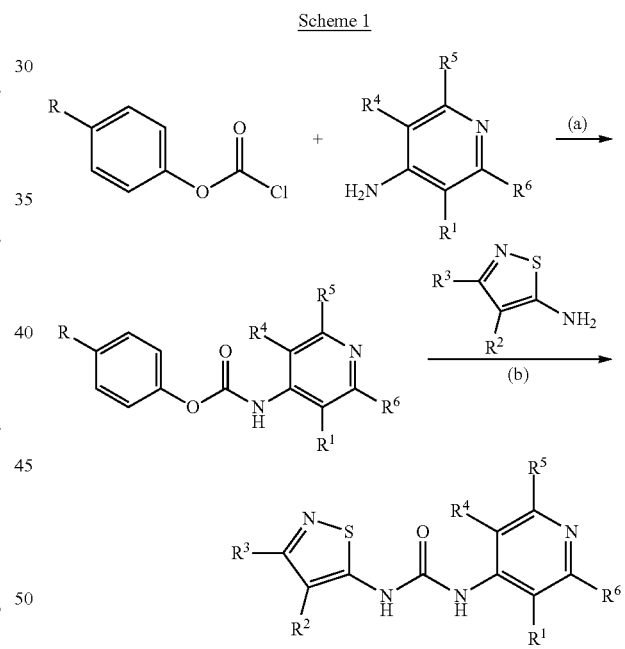

Scheme 1

Step (a) involves reaction of (un)substituted phenyl chloroformate (for example, R can be H or nitro group) and (un)substituted 4-aminopyridine in a suitable solvent such as DCM or dioxane with a suitable base such as pyridine at a suitable temperature such as RT.

Step (b) involves reaction of substituted 5-aminoisothiazole (or substituted 3-aminobenzothiazoles) and the carbamate intermediate obtained in Step (a) in a suitable solvent such as THF or dioxane with a suitable base such as diisopropylethylamine at a suitable temperature such as 60° C. Alternatively, the substituted 5-aminoisothiazole (or substituted 3-aminobenzothiazoles) may be deprotonated by a suitable base such as LHMDS first, followed by reaction with the carbamate intermediate obtained in Step (a). Following the formation of the urea, $R^1$-$R^6$ groups may undergo further transformations as needed to provide the desired products.

Scheme 2

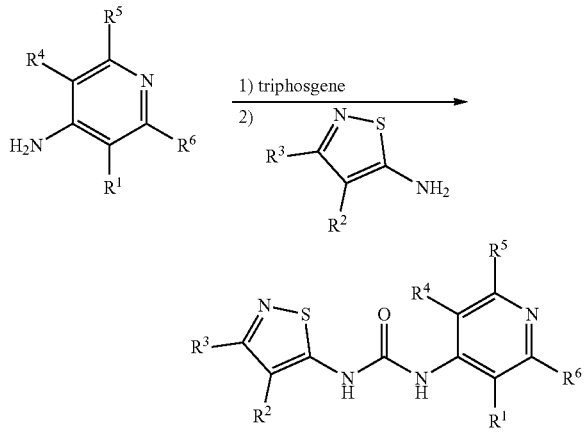

Formation of urea product involves reaction of (un)substituted 4-aminopyridine with triphosgene, followed by substituted 5-aminoisothiazole, in a suitable solvent such as THF with a suitable base such as triethylamine at a suitable temperature such as RT. Following the formation of the urea, $R^1$-$R^6$ groups may undergo further transformations as needed to provide the desired products.

EXAMPLES

The following Examples have been prepared, isolated and characterized using the methods disclosed herein. The following examples demonstrate a partial scope of the disclosure and are not meant to be limiting of the scope of the disclosure.

Unless specified otherwise, starting materials are generally available from a non-limiting commercial sources such as TCI Fine Chemicals (Japan), Aurora Fine Chemicals LLC (San Diego, CA), FCH Group (Ukraine), Aldrich Chemicals Co. (Milwaukee, Wis.), Acros Organics (Fairlawn, N.J.), Maybridge Chemical Company, Ltd. (Cornwall, England), Matrix Scientific (USA), Enamine Ltd (Ukraine), Combi-Blocks, Inc. (San Diego, USA), Oakwood Products, Inc. (USA), Apollo Scientific Ltd. (UK).

Example 1

1-(2-chloropyridin-4-yl)-3-(3-(difluoromethyl)isothiazol-5-yl)urea

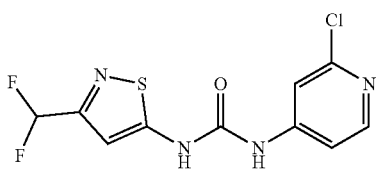 [SMILES: O=C(Nc1ccnc(Cl)c1)Nc1cc(C(F)F)ns1]

To a mixture of 2-chloro-4-aminopyridine (1.57 g, 12.25 mmol) and pyridine (1.38 mL, 17.05 mmol) in DCM (100 mL) at 0° C. was added 4-nitrophenyl chloroformate (2.6 g, 12.89 mmol). The mixture was maintained at 0° C. for 2 min, then warmed up at rt. After another 20 min, the mixture was concentrated in vacuo to give a residue, which was taken up in dioxane (80 mL). A solution of 3-(difluoromethyl)isothiazol-5-amine (Intermediate 1) (1.60 g, 10.66 mmol) in dioxane (10 mL) was rapidly added, followed by DIPEA (6.51 mL, 37.3 mmol). The mixture was heated to 60° C. After 3 h, the mixture was cooled to RT, then water and EtOAc were added. The organic layer was washed repeatedly with water, saturated aqueous sodium bicarbonate and brine. The organic phase was dried over sodium sulfate, filtered and concentrated in vacuo to obtain a residue which was purified by flash chromatography (EtOH/EtOAc/heptane). The partially purified residue was triturated with ether, and the obtained solid was taken up in water. Lyophilization removed residual ether to give the title compound. $^1$H NMR (400 MHz, DMSO-d6) δ 11.08 (s, 1H), 10.15 (s, 1H), 8.26 (d, J=4 Hz, 1H), 7.68 (d, J=2 Hz, 1H), 7.46 (dd, J=4, 2 Hz, 1H), 7.15 (s, 1H), 6.97 (t, J=52 Hz, 1H). MS (ESI) m/z 305.1 [M+H]$^+$. LCMS: Rt=1.25 min, m/z 305.1 (M+H) (LCMS method 1). $^1$H NMR (400 MHz, DMSO-d$_6$) δ 11.08 (s, 1H), 10.15 (s, 1H), 8.26 (d, J=4 Hz, 1H), 7.68 (d, J=2 Hz, 1H), 7.46 (dd, J=4, 2 Hz, 1H), 7.15 (s, 1H), 6.97 (t, J=52 Hz, 1H).

Example 2

1-(2-chloropyridin-4-yl)-3-(3-methylisothiazol-5-yl)urea

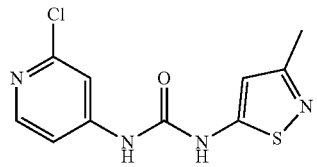 [SMILES: Cc1cc(NC(=O)Nc2ccnc(Cl)c2)sn1]

A solution of 2-chloro-4-aminopyridine (101 mg, 0.786 mmol) in THF (2 mL) was added slowly to a solution of triphosgene (101 mg, 0.340 mmol) in THF (2 mL) at RT. Triethylamine (0.11 mL, 0.790 mmol) was then added. After the mixture was stirred at RT for 20 min, a mixture of 3-methyl-5-aminoisothiazole hydrochloride (120 mg, 0.797 mmol) and triethylamine (0.12 mL, 0.863 mmol) in THF (2 mL) was added. The mixture was stirred at RT for 18 h and partitioned between EtOAc and aqueous KOH. The combined organic extract was dried over MgSO$_4$ and concentrated. The residue was purified by HPLC (basic method) to give the title compound. LCMS: Rt=0.85 min, m/z 269.0 (M+H) (LCMS method 2). $^1$H NMR (400 MHz, DMSO-d$_6$) δ 10.78 (s, 1H), 9.87 (s, 1H), 8.24 (d, J=4 Hz, 1H), 7.66 (s, 1H), 7.43 (d, J=4 Hz, 1H), 6.73 (s, 1H), 2.30 (s, 3H).

Example 3

1-(2-chloropyridin-4-yl)-3-(3-(trifluoromethyl)isothiazol-5-yl)urea

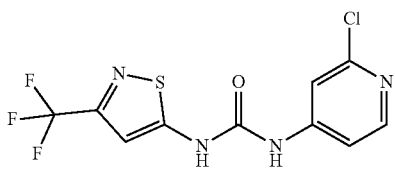 [SMILES: O=C(Nc1ccnc(Cl)c1)Nc1cc(C(F)(F)F)ns1]

To an ice-cold mixture of 3-(trifluoromethyl)isothiazol-5-amine (Intermediate 2) (70 mg, 0.41 mmol), and phenyl (2-chloropyridin-4-yl)carbamate (Intermediate 3) (104 mg, 0.41 mmol) in DMF (1.2 mL) was added a solution of LHMDS (1M in THF, 0.41 mL, 0.41 mmol). The mixture was allowed to warm to RT and stirred for 16 h. The mixture was concentrated in vacuo, then purified by HPLC (basic method) to obtain the title compound. LCMS: Rt=1.38 min, m/z 323 (M+H) (LCMS method 1). $^1$H NMR (400 MHz, DMSO-d6) δ 11.21 (br s, 1H), 10.18 (br s, 1H), 8.23 (d, J=5.6 Hz, 1H), 7.69 (d, J=1.8 Hz, 1H), 7.46 (dd, J=5.7, 1.9 Hz, 1H), 7.22 (s, 1H).

Example 4

1-(5-amino-2-chloropyridin-4-yl)-3-(3-(difluoromethyl)isothiazol-5-yl)urea

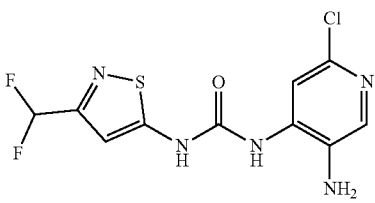

A mixture of 1-(5-nitro-2-chloropyridin-4-yl)-3-(3-(difluoromethyl)isothiazol-5-yl)urea (Intermediate 5) (7.63 g, 21.82 mmol), iron (4.87 g, 87 mmol) and ammonium chloride (9.34 g, 175 mmol) in ethanol (84 mL) and water (25 mL) was heated for 1 h at 50° C. The mixture was filtered over Celite, the filter cake was rinsed with MeOH, and the filtrate was concentrated in vacuo. The residue was taken up in EtOAc and washed with brine. The organic fraction was dried over magnesium sulfate and concentrated in vacuo to give a residue which was purified by silica gel chromatography (EtOAc/heptane) followed by purification using ISCO reverse phase purification on a C18 column eluting with water+0.1% formic acid and acetonitrile+0.1% formic acid. LCMS: Rt=0.76 min, m/z=320.2 (M+H) (LCMS method 2). $^1$H NMR (400 MHz, Methanol-d$_4$) δ 7.88 (s, 1H), 7.84 (s, 1H), 6.99 (s, 1H), 6.66 (t, J=54.9 Hz, 1H).

Example 5

1-(2-chloro-5-(hydroxymethyl)pyridin-4-yl)-3-(3-(difluoromethyl)isothiazol-5-yl)urea

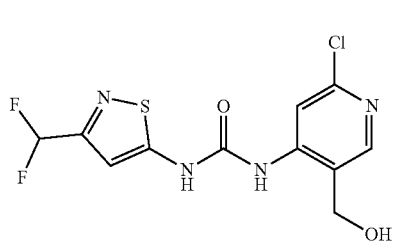 [SMILES: O=C(Nc1cc(C(F)F)ns1)Nc1cc(Cl)ncc1CO]

Step 1: Synthesis of 1-(5-(((tert-butyldimethylsilyl)oxy)methyl)-2-chloropyridin-4-yl)-3-(3-(difluoromethyl)isothiazol-5-yl)urea LHMDS (1M in THF, 9.2 mL, 9.2 mmol) was added dropwise to a solution of phenyl (5-(((tert-butyldimethylsilyl)oxy)methyl)-2-chloropyridin-4-yl)carbamate (Intermediate 6) (3.46 g, 8.81 mmol) and 3-(difluoromethyl)isothiazol-5-amine (Intermediate 1) (1.15 g, 7.66 mmol) in DMF (30 mL), and the reaction was stirred at RT for 30 min. The reaction was quenched with MeOH (10 mL) and volatiles were removed in vacuo. The residue was taken up in 1:1 EtOAc/saturated aqueous NH$_4$Cl and the layers were separated. The aqueous layer was extracted with EtOAc. The organics were combined, dried with Na$_2$SO$_4$, filtered, and volatiles were removed in vacuo. The crude residue was purified by silica gel chromatography (EtOAc/heptane). LCMS: Rt=1.79 min, m/z=449.2 (M+H) (LCMS method 1). $^1$H NMR (400 MHz, DMSO-d6) δ 11.39 (s, 1H), 8.93 (s, 1H), 8.29 (s, 1H), 8.14 (s, 1H), 7.19 (s, 1H), 6.96 (t, J=54.5 Hz, 1H), 4.79 (s, 2H), 0.86 (s, 9H), 0.07 (s, 6H).

Step 2: Synthesis of 1-(2-chloro-5-(hydroxymethyl)pyridin-4-yl)-3-(3-(difluoromethyl)isothiazol-5-yl)urea TBAF (1M in THF, 2.45 mL, 2.45 mmol) was added to a solution of 1-(5-(((tert-butyldimethylsilyl)oxy)methyl)-2-chloropyridin-4-yl)-3-(3-(difluoromethyl)isothiazol-5-yl)urea (obtained in step 1 above) (1.1 g, 2.45 mmol) and in THF (8 mL), and the mixture was stirred at RT for 2 h. The reaction mixture was poured into water, and product was extracted with EtOAc. The organic extract was combined, dried with Na$_2$SO$_4$, filtered, and volatiles were removed in vacuo. The crude product was purified by silica gel chromatography (MeOH/DCM) to give the title compound. LCMS: Rt=0.78 min, m/z=335.2 (M+H) (LCMS method 2). $^1$H NMR (400 MHz, DMSO-d$_6$) δ 11.75 (s, 1H), 9.22 (s, 1H), 8.23 (s, 1H), 8.15 (s, 1H), 7.20 (s, 1H), 6.97 (t, J=56 Hz, 1H), 5.79 (t, J=5 Hz, 1H), 4.59 (d, J=5 Hz, 2H).

Example 6

1-(5-amino-2-fluoropyridin-4-yl)-3-(3-(difluoromethyl)isothiazol-5-yl)urea

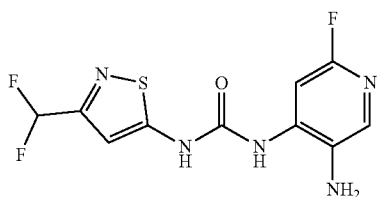

A mixture of 1-(5-nitro-2-chloropyridin-4-yl)-3-(3-(difluoromethyl)isothiazol-5-yl)urea (Intermediate 5) (3.77 g, 8.62 mmol), TMAF (3.61 g, 38.8 mmol) and DMF (83 mL) was heated at 75° C. for 1 h. The reaction was quenched with water and extracted with EtOAc. The combined organic fractions were washed with water, brine, then dried with sodium sulfate, filtered and concentrated in vacuo. The residue was then purified by flash chromatography (EtOAc/heptane) to give partially purified product (2.73 g) which was taken up in ethanol (100 mL) and water (20 mL). Ammonium chloride (2.13 g, 39.8 mmol) and iron (1.91 g, 34.2 mmol) were added and the mixture was heated to 45° C. for 30 min. The reaction mixture was then filtered on a short pad of celite, which was washed with MeOH. The filtrate was concentrated down, and then diluted with EtOAc and water. The aqueous layer was extracted with EtOAc. The combined organic fractions were washed with brine, then dried with sodium sulfate, filtered and concentrated in vacuo. The residue was sequentially purified by silica gel chromatography (EtOAc/heptane), followed by ISCO reverse phase purification on a C18 column eluting with water+0.1% formic acid and acetonitrile+0.1% formic acid. A small number of impure fractions were finally purified by HPLC (formic acid method) and the combined fractions afforded the title compound. LCMS: Rt=1.12 min, m/z 304.2 (M+H) (LCMS method 1). $^1$H NMR (400 MHz, DMSO-$d_6$) δ 11.15 (s, 1H), 8.92 (s, 1H), 7.63 (d, J=0.9 Hz, 1H), 7.46 (d, J=0.8 Hz, 1H), 7.14 (s, 1H), 6.95 (t, J=54.5 Hz, 1H), 4.82 (s, 2H).

Example 7

1-(3-(difluoromethyl)isothiazol-5-yl)-3-(2-fluoro-5-(hydroxymethyl)pyridin-4-yl)urea

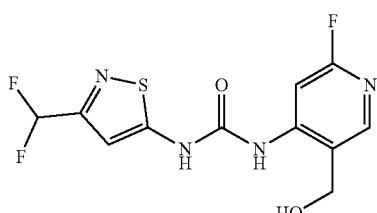

Step 1: Synthesis of 1-(5-(((tert-butyldimethylsilyl)oxy)methyl)-2-fluoropyridin-4-yl)-3-(3-(difluoromethyl)isothiazol-5-yl)urea To a solution of 3-(difluoromethyl)isothiazol-5-amine (Intermediate 1) (48 mg, 0.323 mmol), and phenyl (5-(((tert-butyldimethylsilyl)oxy)methyl)-2-fluoropyridin-4-yl)carbamate (Intermediate 7) (135 mg, 0.323 mmol) in DMF (2 mL) was added LHMDS (1M in THF, 0.484 mL, 0.484 mmol) and the resulting mixture was stirred at RT for 30 min. The mixture was concentrated in vacuo and the product purified by silica gel chromatography (EtOAc/heptane) to give the title compound. LCMS: Rt=1.76 min, m/z 433.2 (M+H) (LCMS method 1

Step 2: Synthesis of 1-(3-(difluoromethyl)isothiazol-5-yl)-3-(2-fluoro-5-(hydroxymethyl)pyridin-4-yl)urea To a solution of 1-(5-(((tert-butyldimethylsilyl)oxy)methyl)-2-fluoropyridin-4-yl)-3-(3-(difluoromethyl)isothiazol-5-yl)urea (119 mg, 0.275 mmol) in THF (5 mL) was added TBAF (1M in THF, 0.275 mL, 0.275 mmol) and the resulting mixture was allowed to stir at RT for 2 h. The mixture was concentrated in vacuo and purified by silica gel chromatography (MeOH/DCM with ammonium hydroxide as the modifier) to give the title compound. LCMS: Rt=1.16 min, m/z 337 (M+H) (LCMS method 1). $^1$H NMR (400 MHz, DMSO-$d_6$) δ 11.76 (s, 1H), 9.26 (s, 1H), 8.06 (s, 1H), 7.77 (s, 1H), 7.22-6.70 (m, 2H), 5.73 (t, J=5.4 Hz, 1H), 4.59 (d, J=5.1 Hz, 2H).

Example 8

1-(3-(difluoromethyl)isothiazol-5-yl)-3-(2-fluoro-3-(hydroxymethyl)pyridin-4-yl)urea

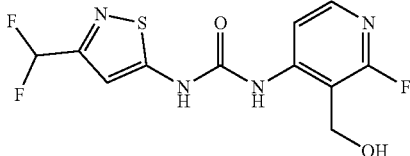 [SMILES: O=C(Nc1cc(C(F)F)ns1)Nc1ccnc(F)c1CO]

Step 1: Synthesis of 1-(3-(((tert-butyldimethylsilyl)oxy)methyl)-2-fluoropyridin-4-yl)-3-(3-(difluoromethyl)isothiazol-5-yl)urea To a solution of 3-(difluoromethyl)isothiazol-5-amine (Intermediate 1) (1.04 g, 6.93 mmol), and phenyl (3-(((tert-butyldimethylsilyl)oxy)methyl)-2-fluoropyridin-4-yl)carbamate (Intermediate 8) (3.39 g, 9.00 mmol) in DMF (35 mL) was added LHMDS (1M in THF, 13.8 mL, 13.8 mmol) at 0° C. The cooling bath was removed and the resulting mixture was stirred at RT for 45 min. The mixture was concentrated in vacuo and the product purified by silica gel chromatography (EtOAc/heptane) to give the title compound. LCMS: Rt=1.74 min, m/z 433.3 (M+H) (LCMS method 1).

Step 2: Synthesis of 1-(3-(difluoromethyl)isothiazol-5-yl)-3-(2-fluoro-3-(hydroxymethyl)pyridin-4-yl)urea To a solution of 1-(3-(((tert-butyldimethylsilyl)oxy)methyl)-2-fluoropyridin-4-yl)-3-(3-(difluoromethyl)isothiazol-5-yl)urea (2.19 g, 5.06 mmol) in THF (40 mL) was added TBAF (1M in THF, 6.6 mL, 6.6 mmol) and the resulting mixture was allowed to stir at RT for 30 min. The reaction was quenched with water, then diluted with EtOAc. The aqueous layer was extracted with EtOAc. The combined organic fractions were combined, washed with brine, then dried with sodium sulfate, filtered and concentrated in vacuo. The crude mixture was purified by flash chromatography (MeOH/DCM) to give the title compound. LCMS: Rt=1.12 min, m/z 319.2 (M+H) (LCMS method 1). 1H NMR (400 MHz, DMSO-d6) δ 11.89 (s, 1H), 9.44 (s, 1H), 8.10-8.02 (m, 2H), 7.05 (s, 1H), 6.95 (t, J=54.5 Hz, 1H), 5.83 (s, 1H), 4.62 (s, 2H).

INTERMEDIATES

Intermediate 1

3-(Difluoromethyl)isothiazol-5-amine

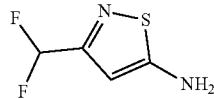

Step 1: 3-methyl-5-nitroisothiazole

Cu powder (96 g, 1.5 mol) was placed in a 5 L reactor. Water (1 L) was added followed by NaNO$_2$ (104 g, 1.5 mol). Aqueous HCl (12 M, 1.5 mL, 18 mmol) was added, and the reaction mixture was stirred for 20 min. A solution of 3-methyl-5-aminoisothiazole hydrochloride (58 g, 507 mmol) in 500 mL of water and aqueous HCl (12 M, 65 mL, 0.78 mol) was added dropwise via addition funnel maintaining the temperature below 30° C. An additional 100 mL of water was added. The reaction mixture was allowed to stir for 3 h after addition. The reaction mixture was filtered through Celite with water and MTBE. The filtrate was transferred to the reactor and the layers were separated. The aqueous layer was washed twice with MTBE. The combined organic layers were dried over MgSO$_4$, filtered and concentrated to give the title compound. $^1$H NMR (400 MHz, DMSO-d6) δ 8.12 (s, 1H), 2.50 (s, 3H).

Step 2: 5-nitroisothiazole-3-carboxylic acid

To a 1 L 3-neck round bottom flask in a water bath equipped with a mechanical stirrer and a temperature monitor was added 3-methyl-5-nitroisothiazole (26.5 g, 184 mmol), then H$_2$SO$_4$ (350 mL) at a rate to keep the temperature below 30° C. CrO$_3$ (55.1 g, 552 mmol) was added in 6 portions every 20 min, ensuring the temperature remained below 24° C. The reaction was left stirring in the presence of the water bath for 3 days. The reaction mixture was poured into ice water (total of 1.4 L) and was extracted 3 times with Et$_2$O (1 L). The combined organic layers were washed with brine, then dried over MgSO$_4$, filtered and concentrated to provide a yellow solid. The solid was taken up in heptane (80 mL) and Et$_2$O (20 mL) and triturated. After 2 min of vigorous stirring, the mixture was filtered, and then rinsed with a 5:1 heptane/ether mixture (minimal amount) to provide the title compound. $^1$H NMR (400 MHz, DMSO-d6) δ 9.89 (s, 1H), 8.57 (s, 1H).

Step 3: (5-Nitroisothiazol-3-yl)methanol

A flask was charged with 5-nitroisothiazole-3-carboxylic acid (3.0 g, 17.2 mmol) in THF (50 mL), cooled on an ice bath, then borane tetrahydrofuran complex (1M in THF) (22.4 mL, 22.4 mmol) was added dropwise over 30 min and the reaction was allowed to warm overnight. The reaction mixture was re-cooled to 0° C., then methanol (20 mL) was added dropwise. The reaction was vigorously stirred at 0° C. for 5 min, then allowed to warm to RT and stirred for another 15 min.

The reaction mixture was concentrated in vacuo to half volume, then was diluted with EtOAc (100 mL), saturated aqueous NH$_4$Cl (50 mL) and water (50 mL). The layers were separated and the aqueous portion was extracted with EtOAc (2×100 mL). The organic fractions were combined and washed with brine, then dried over sodium sulfate, filtered and concentrated in vacuo. Purification via silica gel chromatography (EtOAc/DCM) gave the title compound. $^1$H NMR (400 MHz, DMSO-d6) δ 8.09 (s, 1H), 5.77 (t, J=6.1 Hz, 1H), 4.58 (d, J=6.1 Hz, 2H). MS (ESI) m/z 161.0 [M+H]$^+$.

Step 4: Synthesis of 5-nitroisothiazole-3-carbaldehyde

Dess-Martin periodinane (2.23 g, 5.27 mmol) was added in small portions over 5 min to (5-nitroisothiazol-3-yl)methanol (767 mg, 4.79 mmol) in DCM (25 mL) at 0° C. The mixture was stirred at 0° C. for 10 min, warmed to RT and stirred at RT for 20 min. The mixture was diluted with DCM. Saturated aqueous NaHCO$_3$ and saturated aqueous sodium thiosulfate were added. The mixture was vigorously stirred for 10 min, and then two layers were separated. The aqueous layer was extracted with DCM. The combined organic extract was washed with brine, dried over sodium sulfate and concentrated in vacuo to give the title compound. The product was used directly in the next step without purification. $^1$H NMR (400 MHz, DMSO-d$_6$) δ 9.85 (s, 1H), 8.58 (s, 1H).

Step 5: Synthesis of 3-(difluoromethyl)-5-nitroisothiazole

DAST (0.201 mL, 1.518 mmol) was added at 0° C. in a dropwise fashion to a solution of 5-nitroisothiazole-3-carbaldehyde (obtained in step 1 above) (80 mg, 0.506 mmol) in DCM (3.5 mL). The mixture was stirred at 0° C. for 25 min, warmed to RT and stirred at RT for 2 h. The mixture was quenched at 0° C. with saturated aqueous NaHCO$_3$, and diluted with DCM. The mixture was vigorously stirred for 1 min, and the two layers were separated. The aqueous layer was extracted with DCM. The combined organic extract was washed with brine, dried over sodium sulfate and concentrated in vacuo to give the title compound. The product was used immediately in the next step without purification. $^1$H NMR (400 MHz, DMSO-d$_6$) δ 8.54 (s, 1H), 7.16 (t, J=52 Hz, 1H).

Step 6: Synthesis of 3-(difluoromethyl)isothiazol-5-amine

A mixture of 3-(difluoromethyl)-5-nitroisothiazole (49 mg, 0.27 mmol), iron powder (46 mg, 0.81 mmol) and acetic acid (1.5 mL) was heated to 50° C. for 2 h. The mixture was diluted with ethyl acetate and basified with 30% ammonium hydroxide. The organic layer was separated and concentrated in vacuo, then purified by silica gel chromatography (EtOAc/heptane) to obtain the title compound. LCMS: Rt=0.42 min; m/z 151.2 (M+H) (LCMS method 2); $^1$H NMR (400 MHz, methanol-d4) δ 6.46 (t, J=55.0 Hz, 1H), 6.39 (s, 1H). $^{19}$F NMR (376 MHz, MeOD) 5-116.06.

Intermediate 2

3-(trifluoromethyl)isothiazol-5-amine

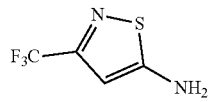

Step 1: Synthesis of 4,4,4-trifluoro-3-oxobutanenitrile

A dry 100 mL flask was charged with KOt-Bu (1M in THF, 85 mL, 85 mmol) and cooled down on ice. After 30 min, a mixture of ethyl trifluoroacetate (7.27 mL, 60.9 mmol) and acetonitrile (3.18 mL, 60.9 mmol) was added over 3 min. The reaction mixture became a suspension. The mixture was allowed to slowly warm up to RT and stirred for 24 h. The mixture was quenched with 1M HCl, and the crude product was extracted with ether and washed with water. The organic layer was separated, dried over magnesium sulfate, filtered and concentrated in vacuo to furnish the title compound, which was used in the next step without purification. LCMS: Rt=0.22 min, m/z 136.1 (M−1) (LCMS method 4). $^1$H NMR (400 MHz, DMSO-d$_6$) δ 2.99 (s, 2H).

Step 2: Synthesis of (Z)-3-amino-4,4,4-trifluorobut-2-enenitrile

A mixture of 4,4,4-trifluoro-3-oxobutanenitrile (prepared in step 1) (1.1 g, 8.03 mmol), ammonium formate (1.518 g, 24.08 mmol) and acetic acid (0.046 mL, 0.803 mmol) in toluene (100 mL) was heated to 120° C. under zeotropic conditions for 18 h. The mixture was concentrated in vacuo and used in the next step without further purification.

Step 3: Synthesis of (Z)-3-amino-4,4,4-trifluorobut-2-enethioamide

A mixture of (Z)-3-amino-4,4,4-trifluorobut-2-enenitrile (prepared in step 2) (1.00 g, 7.35 mmol), MgCl$_2$ (0.70 g, 7.35 mmol) and NaSH (0.824 g, 14.70 mmol) in DMF (20 mL) was allowed to stir at RT for 24 h. The mixture was partitioned between ethyl acetate and water. The combined organic extract was dried over magnesium sulfate, filtered and concentrated in vacuo to furnish the title compound. LCMS: Rt=0.81 min, m/z 171 (M+H) (LCMS method 1).

Step 4: Synthesis of 3-(trifluoromethyl)isothiazol-5-amine

To a mixture of (Z)-3-amino-4,4,4-trifluorobut-2-enethioamide (prepared in step 3) (1.2 g, 7.05 mmol) in pyridine (24 mL) was added H$_2$O$_2$ (3 mL, 29.4 mmol) at 0-5° C., and the mixture was allowed to warm up to RT and stirred for 2 h. The mixture was concentrated in vacuo, and the residue was chromatographed on silica gel (ethyl acetate/heptane) to give the title compound. LCMS: Rt=0.97 min, m/z 169 (M+H) (LCMS method 1). $^1$H NMR (400 MHz, DMSO-d$_6$) δ 7.21 (s, 2H), 6.44 (s, 1H).

Intermediate 3

Phenyl (2-chloropyridin-4-yl)carbamate

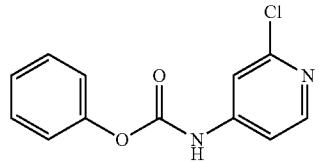 [SMILES: O=C(Nc1ccnc(Cl)c1)Oc1ccccc1]

To a solution of 2-chloropyridin-4-amine (12.9 g, 101 mmol) and pyridine (8.13 mL, 101 mmol) in DCM (315 mL) at 0° C. was added phenyl chloroformate (13.3 mL, 106 mmol). The mixture was allowed to warm to RT over 2 h and concentrated in vacuo. Water was added, and the mixture was stirred at RT. The solid was filtered over a fritted plastic funnel, rinsed with water and dried under high vacuum at 40° C. for 24 h to give the title compound. LCMS: Rt=1.20 min, m/z=249.2 (M+H) (LCMS method 2).

Intermediate 4

Phenyl (2-chloro-5-nitropyridin-4-yl)carbamate

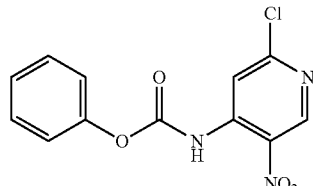

To a solution of 4-amino-2-chloro-5-nitropyridine (150 mg, 0.864 mmol) and pyridine (0.070 mL, 0.86 mmol) in dioxane (4 mL) at 0° C. was phenyl chloroformate (0.114 mL, 0.907 mmol). The mixture was heated at 80° C. for 18 h, cooled to RT and poured into water. The product was extracted with EtOAc. The combined organic extract was dried over Na$_2$SO$_4$, and concentrated in vacuo. The crude residue was purified by silica gel chromatography (EtOAc/heptane) to give the title compound. LCMS: Rt=1.51 min, m/z=294.1 (M+H) (LCMS method 1).

Intermediate 5

1-(5-nitro-2-chloropyridin-4-yl)-3-(3-(difluoromethyl)isothiazol-5-yl)urea

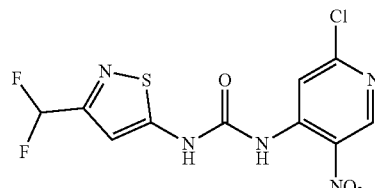

A solution of phenyl (2-chloro-5-nitropyridin-4-yl)carbamate (Intermediate 4) (4.50 g, 15.32 mmol), 3-(difluoromethyl)isothiazol-5-amine (Intermediate 1) (2.0 g, 13.32 mmol) and DIPEA (5.8 mL, 33.3 mmol) in dioxane (59 mL) was heated at 85° C. for 16 h. The mixture was concentrated in vacuo and the residue was purified by silica gel chromatography (EtOAc/heptane) to give the title compound. LCMS: Rt=1.43 min, m/z=350.1 (M+H) (LCMS method 1).

Intermediate 6

Phenyl (5-(((tert-butyldimethylsilyl)oxy)methyl)-2-chloropyridin-4-yl)carbamate

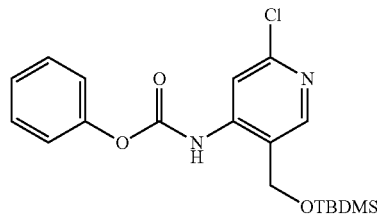 [SMILES: CC(C)(C)[Si](C)(C)OCc1cnc(Cl)cc1NC(=O)Oc1ccccc1]

Step 1: Synthesis of methyl 6-chloro-4-((4-methoxybenzyl)amino)nicotinate

A mixture of p-methoxybenzylamine (19.0 mL, 146 mmol), methyl 4,6-dichloronicotinate (25 g, 121 mmol), triethylamine (20.3 mL, 146 mmol) in MeCN (60 mL) was stirred at RT for 24 h. More 4-methoxybenzylamine (2.5 mL) was added, and the mixture was stirred at RT for 72 h. The mixture was concentrated, and the residue was partitioned between EtOAc and aqueous saturated $NH_4Cl$. The organic extract was combined, dried with $Na_2SO_4$, filtered and concentrated in vacuo. The crude residue was purified by silica gel chromatography (EtOAc/heptane) to give the title compound. LCMS: Rt=1.42 min, m/z=307.1 (M+H) (LCMS method 1).

Step 2: Synthesis of (6-chloro-4-((4-methoxybenzyl)amino)pyridin-3-yl)methanol

To a solution of LAH (2M in THF, 21.52 mL, 43.0 mmol) in THF (150 mL) stirring at 0° C. was added a solution of methyl 6-chloro-4-((4-methoxybenzyl)amino)nicotinate (prepared in step 1) (12 g, 39.1 mmol) in THF (100 mL) dropwise. The reaction was allowed to warm to RT and was stirred for 30 min. The reaction was quenched with slow addition of EtOAc in an ice bath, followed by Steinhardt conditions for quenching LAH (2 mL $H_2O$, followed by 2 mL of 15% NaOH and 6 mL of $H_2O$). The resulting solution was stirred for 15 min and was allowed to warm to RT. The mixture was filtered over Celite and the filtrate was transferred to a separatory funnel. The product was further diluted with water and then extracted with EtOAc. The organics were combined, dried with $Na_2SO_4$, filtered, and volatiles were removed in vacuo to give the title compound. LCMS: Rt=0.84 min, m/z=279.3 (M+H) (LCMS 1 method 1).

Step 3: Synthesis of (4-amino-6-chloropyridin-3-yl)methanol

A solution of (6-chloro-4-((4-methoxybenzyl)amino)pyridin-3-yl)methanol (prepared in step 2) (9.82 g, 35.2 mmol) in TFA (2.71 mL, 35.2 mmol) was heated at 60° C. for 18 h. The reaction was neutralized with 10% aqueous $K_2CO_3$ to pH~7. The mixture was then transferred to a separatory funnel and was extracted with DCM. The organics were combined, dried with $Na_2SO_4$, filtered, and volatiles were removed in vacuo to give a portion of the title compound. The aqueous layer was concentrated in vacuo, and the resulting solid was diluted in isopropanol. Insoluble salts were filtered off, and the solution was cooled on ice. Additional salts that precipitated out were filtered off. Volatiles were removed in vacuo to give more amount of the title compound. LCMS: Rt=0.26 min, m/z=159.1 (M+H) (LCMS method 2).

Step 4: Synthesis of 5-(((tert-butyldimethylsilyl)oxy)methyl)-2-chloropyridin-4-amine A mixture of (4-amino-6-chloropyridin-3-yl)methanol (prepared in step 3) (5 g, 32 mmol), TBDMSCl (5.23 g, 34.7 mmol) and imidazole (5.37 g, 79 mmol) in DMF (10 mL) was stirred at RT for 1 h. The reaction mixture was poured into water and was extracted with EtOAc. The organics were combined, dried with $Na_2SO_4$, filtered, and volatiles were removed in vacuo. The crude residue was purified by silica gel chromatography (EtOAc/heptane) to give the title compound. LCMS: Rt=1.52 min, m/z=273.2 (M+H) (LCMS method 2).

Step 5: Synthesis of Phenyl (5-(((tert-butyldimethylsilyl)oxy)methyl)-2-chloropyridin-4-yl)carbamate To a solution of 5-(((tert-butyldimethylsilyl)oxy)methyl)-2-chloropyridin-4-amine (prepared in step 4) (5.55 g, 20.3 mmol) and pyridine (1.8 mL, 22.4 mmol) in DCM (75 mL) stirring at RT was added phenyl chloroformate (2.68 mL, 21.4 mmol). The reaction was allowed to warm to RT over 2 h. Volatiles were removed in vacuo, and the residue was diluted with EtOAc and saturated aqueous $NaHCO_3$. The mixture was then extracted with EtOAc. The organics were combined, dried with $Na_2SO_4$, filtered, and volatiles were removed in vacuo. The crude residue was purified by silica gel chromatography (EtOAc/heptane) to give the title compound. LCMS: Rt=1.94 min, m/z=393.3 (M+H) (LCMS method 1).

Intermediate 7

Phenyl (5-(((tert-butyldimethylsilyl)oxy)methyl)-2-fluoropyridin-4-yl)carbamate

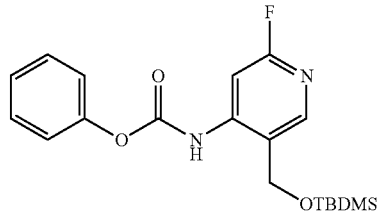 [SMILES: CC(C)(C)[Si](C)(C)OCc1cnc(F)cc1NC(=O)Oc1ccccc1]

Step 1: Synthesis of methyl 4-amino-6-fluoronicotinate

To a 500 mL flask containing methyl-4,6-dichloronicotinate (6.75 g, 32.8 mmol) and TMAF (8.0 g, 86 mmol) was added DMF (100 mL) and the mixture was stirred at RT for 1.5 h until complete formation of intermediate methyl-4,6-difluoronicotinate was identified by LCMS. To this reaction mixture was then added a solution of 2M ammonia in isopropanol (35 mL, 70 mmol) and stirred at RT for 20 h. Complete formation of the title compound was identified by LCMS. The reaction mixture was quenched with water, and the crude product was extracted with EtOAc. The organic layer was washed with brine, then dried over sodium sulfate, filtered and concentrated in vacuo. The residue was purified by silica gel chromatography (EtOAc/heptane) to obtain the title compound. LCMS: Rt=0.97 min, m/z 174 (M+H) (LCMS method 1). $^1$H NMR (400 MHz, DMSO-d$_6$) δ 8.43 (s, 1H), 7.52 (s, 2H), 6.30 (s, 1H), 3.82 (s, 3H).

Step 2: Synthesis of (4-amino-6-fluoropyridin-3-yl)methanol

To an ice-cold (0° C.) solution of LAH (2M in THF, 24.8 mL, 49.6 mmol) diluted further with THF (200 mL) was added, via addition funnel over 45 min, a solution of methyl 4-amino-6-fluoronicotinate (4.22 g, 24.8 mmol) in THF (100 mL) resulting in a suspension. The mixture was allowed to warm to RT for 2 h after which the reaction was judged complete by LCMS. The reaction mixture was diluted with THF (200 mL) and cooled on ice. Sodium sulfate decahydrate was added in portions to the mixture until the bubbling ceased. The mixture was stirred for 18 h, then filtered and concentrated in vacuo. The resulting residue was purified by silica gel chromatography (EtOAc/heptane) to obtain the title compound. LCMS: Rt=0.27 min, m/z 143 (M+H) (LCMS method 3). $^1$H NMR (400 MHz, DMSO-d$_6$) δ 7.63 (s, 1H), 6.20 (s, 2H), 6.09 (s, 1H), 5.04 (t, J=5.5 Hz, 1H), 4.35 (d, J=5.5 Hz, 2H).

Step 3: Synthesis of 5-(((tert-butyldimethylsilyl)oxy)methyl)-2-fluoropyridin-4-amine A mixture of (4-amino-6-fluoropyridin-3-yl)methanol (1.52 g, 10.7 mmol), TBDMSCl (1.77 g, 11.8 mmol), and imidazole (1.82 g, 26.7 mmol) in DMF (50 mL) was stirred at RT for 1 h, after which the reaction was judged complete by TLC, 100% EtOAc. The reaction mixture was concentrated in vacuo, then purified by silica gel chromatography (EtOAc/heptane) to obtain the title compound. LCMS: Rt=1.46 min, m/z 257 (M+H) (LCMS method 1). $^1$H NMR (400 MHz, DMSO-d6) δ 7.60 (s, 1H), 6.11 (s, 2H), 6.04 (s, 1H), 4.50 (s, 2H), 0.81 (s, 9H), 0.00 (s, 6H).

Step 4: Synthesis of phenyl (5-(((tert-butyldimethylsilyl)oxy)methyl)-2-fluoropyridin-4-yl) carbamate To a mixture of (4-amino-6-fluoropyridin-3-yl)methanol (1.45 g, 5.66 mmol) and pyridine (0.46 mL, 5.66 mmol) in dioxane (30 mL) was added phenyl chloroformate (0.710 mL, 5.66 mmol) and the resulting mixture was stirred for 1 h. The mixture was then diluted with EtOAc, then washed with sodium bicarbonate followed by water. The organic portion was dried over sodium sulfate and concentrated in vacuo. The residue was purified by silica gel chromatography (EtOAc/heptane) to obtain the title compound. LCMS: Rt=1.89 min, m/z 377 (M+H) (LCMS method 1). $^1$H NMR (400 MHz, DMSO-d$_6$) δ 9.66 (s, 1H), 8.03 (s, 1H), 7.41 (s, 1H), 7.39-7.31 (m, 2H), 7.16-7.09 (m, 2H), 6.74-6.52 (m, 1H), 4.78 (s, 2H), 0.80 (s, 9H), 0.00 (s, 6H).

Intermediate 8

Phenyl (3-(((tert-butyldimethylsilyl)oxy)methyl)-2-fluoropyridin-4-yl)carbamate

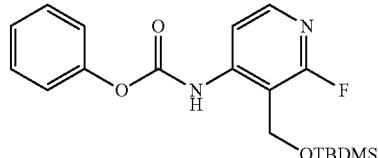 [SMILES: CC(C)(C)[Si](C)(C)OCc1c(NC(=O)Oc2ccccc2)ccnc1F]

Step 1: Synthesis of methyl 2,4-difluoronicotinate

A solution of 2,4-difluoropyridine (5 g, 43.4 mmol) in THF (120 mL) was added dropwise to a stirring solution of lithium diisopropylamide (2M in THF/heptane/ethylbenzene, 26.1 mL, 52.1 mmol) at −78° C. After stirring for 1 h, the reaction was transferred to a stirring solution of methyl chloroformate (5.05 mL, 65.2 mmol) in THF (120 mL) at −78° C. via cannula. The reaction mixture was allowed to warm to RT over 30 min. The reaction was quenched slowly with water (100 mL) and was extracted with EtOAc (3×100 mL). The organics were combined, dried with Na$_2$SO$_4$, filtered, and volatiles were removed in vacuo. The product was purified by silica gel chromatography (EtOAc/heptane) to give the title compound. LCMS: Rt=0.94 min, m/z 174.1 (M+H) (LCMS method 1).

Step 2: Synthesis of methyl 4-amino-2-fluoronicotinate

To a solution of methyl 2,4-difluoronicotinate (prepared in step 1) (2 g, 11.55 mmol) in dioxane (40 mL) was added ammonia in dioxane (0.5M, 46.2 mL, 23.11 mmol). The reaction was stirred at 60° C. for 18 h. The reaction was poured into saturated NaHCO$_{3(aq)}$ and was extracted with EtOAc (3×100 mL). The organics were combined, dried with Na$_2$SO$_4$, filtered, and volatiles were removed in vacuo. The product was purified by silica gel chromatography (EtOAc/heptane) to give the title compound. LCMS: Rt=0.77 min, m/z 171.1 (M+H) (LCMS method 1).

Step 3: Synthesis of (4-amino-2-fluoropyridin-3-yl)methanol

To a solution of methyl 4-amino-2-fluoronicotinate (2.02 g, 11.87 mmol) in THF (70 mL) stirring in an ice bath was added LAH (2M in THF, 7.1 mL, 14.2 mmol) dropwise. The reaction was stirred at 0° C. for 30 min and the reaction was quenched by slowly adding sodium sulfate decahydrate (3.5 g). The mixture was stirred for 15 min, before anhydrous Na$_2$SO$_4$ was added. The mixture was filtered over Celite and the volatiles were removed in vacuo. $^1$H NMR (400 MHz, DMSO-d6) δ 7.56 (d, J=5.7 Hz, 1H), 6.47 (dd, J=5.7, 1.2 Hz, 1H), 6.29 (s, 2H), 4.96 (t, J=5.4 Hz, 1H), 4.40 (d, J=5.4 Hz, 2H).

Step 4: Synthesis of 3-(((tert-butyldimethylsilyl)oxy)methyl)-2-fluoropyridin-4-amine A mixture of (4-amino-2-fluoropyridin-3-yl)methanol (1.57 g, 11.05 mmol), TBDMSCl (2.00 g, 13.26 mmol) and imidazole (1.88 g, 27.6 mmol) was stirred in DMF (30 mL) at RT. After 90 min, the reaction was quenched with sat. aq. NaHCO$_3$, then diluted with EtOAc. The aqueous layer was extracted with EtOAc. The organic fractions were combined, washed with brine, then dried with sodium sulfate, filtered and concentrated in vacuo. The crude mixture was purified by flash chromatography (EtOAc/heptane). LCMS: Rt=1.47 min, m/z 257.3 (M+H) (LCMS method 1).

Step 5: Synthesis of phenyl (3-(((tert-butyldimethylsilyl)oxy)methyl)-2-fluoropyridin-4-yl)carbamate To a solution of 3-(((tert-butyldimethylsilyl)oxy)methyl)-2-fluoropyridin-4-amine (2.36 g, 9.20 mmol) and pyridine (0.89 mL, 11.0 mmol) in dioxane (40 mL) was added phenyl chloroformate (1.21 mL, 9.7 mmol) at RT. After 2.5 h the reaction was quenched with saturated aqueous NaHCO$_3$, then diluted with EtOAc. The aqueous layer was extracted with EtOAc. The organic fractions were combined, washed with brine, then dried with sodium sulfate, filtered and concentrated in vacuo.

The crude mixture was purified by flash chromatography (EtOAc/heptane) to give the title compound. LCMS: Rt=1.91 min, m/z 377.4 (M+H) (LCMS method 1). 1H NMR (400 MHz, DMSO-d6) δ 9.92 (s, 1H), 8.11 (d, J=5.7 Hz, 1H), 7.78 (d, J=5.7 Hz, 1H), 7.52-7.42 (m, 2H), 7.36-7.26 (m, 1H), 7.26-7.19 (m, 2H), 4.90 (s, 2H), 0.87 (s, 9H), 0.08 (s, 6H).

Pharmaceutical Compositions and Combinations

The compounds of the present disclosure are typically used as a pharmaceutical composition (e.g., a compound of the present disclosure and at least one pharmaceutically acceptable carrier). A "pharmaceutically acceptable carrier (diluent or excipient)" refers to media generally accepted in the art for the delivery of biologically active agents to animals, in particular, mammals, including, generally recognized as safe (GRAS) solvents, dispersion media, coatings, surfactants, antioxidants, preservatives (e.g., antibacterial agents, antifungal agents), isotonic agents, absorption delaying agents, salts, preservatives, drug stabilizers, binders, buffering agents (e.g., maleic acid, tartaric acid, lactic acid, citric acid, acetic acid, sodium bicarbonate, sodium phosphate, and the like), disintegration agents, lubricants, sweetening agents, flavoring agents, dyes, and the like and combinations thereof, as would be known to those skilled in the art (see, for example, Allen, L. V., Jr. et al., *Remington: The Science and Practice of Pharmacy* (2 Volumes), 22nd Edition, Pharmaceutical Press (2012).

In one aspect, the present disclosure provides a pharmaceutical composition comprising a compound of the present disclosure, or a pharmaceutically acceptable salt thereof, and a pharmaceutically acceptable carrier. In a further embodiment, the composition comprises at least two pharmaceutically acceptable carriers, such as those described herein. For purposes of the present disclosure, unless designated otherwise, solvates and hydrates are generally considered compositions. Preferably, pharmaceutically acceptable carriers are sterile. The pharmaceutical composition can be formulated for particular routes of administration such as oral administration, parenteral administration, and rectal administration, etc. In addition, the pharmaceutical compositions of the present disclosure can be made up in a solid form (including without limitation capsules, tablets, pills, granules, powders or suppositories), or in a liquid form (including without limitation solutions, suspensions or emulsions).

The pharmaceutical compositions can be subjected to conventional pharmaceutical operations such as sterilization and/or can contain conventional inert diluents, lubricating agents, or buffering agents, as well as adjuvants, such as preservatives, stabilizers, wetting agents, emulsifiers and buffers, etc. Typically, the pharmaceutical compositions are tablets or gelatin capsules comprising the active ingredient together with one or more of:

a) diluents, e.g., lactose, dextrose, sucrose, mannitol, sorbitol, cellulose and/or glycine;
b) lubricants, e.g., silica, talcum, stearic acid, its magnesium or calcium salt and/or polyethyleneglycol; for tablets also
c) binders, e.g., magnesium aluminum silicate, starch paste, gelatin, tragacanth, methylcellulose, sodium carboxymethylcellulose and/or polyvinylpyrrolidone; if desired
d) disintegrants, e.g., starches, agar, alginic acid or its sodium salt, or effervescent mixtures; and
e) absorbents, colorants, flavors and sweeteners.

Tablets may be either film coated or enteric coated according to methods known in the art.

Suitable compositions for oral administration include an effective amount of a compound of the disclosure in the form of tablets, lozenges, aqueous or oily suspensions, dispersible powders or granules, emulsion, hard or soft capsules, or syrups or elixirs. Compositions intended for oral use are prepared according to any method known in the art for the manufacture of pharmaceutical compositions and such compositions can contain one or more agents selected from the group consisting of sweetening agents, flavoring agents, coloring agents and preserving agents in order to provide pharmaceutically elegant and palatable preparations. Tablets may contain the active ingredient in admixture with nontoxic pharmaceutically acceptable excipients which are suitable for the manufacture of tablets. These excipients are, for example, inert diluents, such as calcium carbonate, sodium carbonate, lactose, calcium phosphate or sodium phosphate; granulating and disintegrating agents, for example, corn starch, or alginic acid; binding agents, for example, starch, gelatin or acacia; and lubricating agents, for example magnesium stearate, stearic acid or talc. The tablets are uncoated or coated by known techniques to delay disintegration and absorption in the gastrointestinal tract and thereby provide a sustained action over a longer period. For example, a time delay material such as glyceryl monostearate or glyceryl distearate can be employed. Formulations for oral use can be presented as hard gelatin capsules wherein the active ingredient is mixed with an inert solid diluent, for example, calcium carbonate, calcium phosphate or kaolin, or as soft gelatin capsules wherein the active ingredient is mixed with water or an oil medium, for example, peanut oil, liquid paraffin or olive oil.

Certain injectable compositions are aqueous isotonic solutions or suspensions, and suppositories are advantageously prepared from fatty emulsions or suspensions. Said compositions may be sterilized and/or contain adjuvants, such as preserving, stabilizing, wetting or emulsifying agents, solution promoters, salts for regulating the osmotic pressure and/or buffers. In addition, they may also contain other therapeutically valuable substances. Said compositions are prepared according to conventional mixing, granulating or coating methods, respectively, and contain about 0.1-75%, or contain about 1-50%, of the active ingredient.

Suitable compositions for transdermal application include an effective amount of a compound of the disclosure with a suitable carrier. Carriers suitable for transdermal delivery include absorbable pharmacologically acceptable solvents to assist passage through the skin of the host. For example, transdermal devices are in the form of a bandage comprising a backing member, a reservoir containing the compound optionally with carriers, optionally a rate controlling barrier to deliver the compound of the skin of the host at a controlled and predetermined rate over a prolonged period of time, and means to secure the device to the skin.

Suitable compositions for topical application, e.g., to the skin and eyes, include aqueous solutions, suspensions, ointments, creams, gels or sprayable formulations, e.g., for delivery by aerosol or the like. Such topical delivery systems will in particular be appropriate for dermal application, e.g., for the treatment of skin cancer, e.g., for prophylactic use in sun creams, lotions, sprays and the like. They are thus particularly suited for use in topical, including cosmetic, formulations well-known in the art. Such may contain solubilizers, stabilizers, tonicity enhancing agents, buffers and preservatives.

As used herein a topical application may also pertain to an inhalation or to an intranasal application. They may be conveniently delivered in the form of a dry powder (either alone, as a mixture, for example a dry blend with lactose, or a mixed component particle, for example with phospholipids) from a dry powder inhaler or an aerosol spray presentation from a pressurised container, pump, spray, atomizer or nebuliser, with or without the use of a suitable propellant.

The present disclosure further provides anhydrous pharmaceutical compositions and dosage forms comprising the compounds of the present disclosure as active ingredients, since water may facilitate the degradation of certain compounds.

Anhydrous pharmaceutical compositions and dosage forms of the disclosure can be prepared using anhydrous or low moisture containing ingredients and low moisture or low humidity conditions. An anhydrous pharmaceutical composition may be prepared and stored such that its anhydrous nature is maintained. Accordingly, anhydrous compositions are packaged using materials known to prevent exposure to water such that they can be included in suitable formulary kits. Examples of suitable packaging include, but are not limited to, hermetically sealed foils, plastics, unit dose containers (e. g., vials), blister packs, and strip packs.

The present disclosure further provides pharmaceutical compositions and dosage forms that comprise one or more agents that reduce the rate by which the compound of the present invention as an active ingredient will decompose. Such agents, which are referred to herein as "stabilizers," include, but are not limited to, antioxidants such as ascorbic acid, pH buffers, or salt buffers, etc.

The compound of the present disclosure is typically formulated into pharmaceutical dosage forms to provide an easily controllable dosage of the drug and to give the patient an elegant and easily handleable product. The dosage regimen for the compounds of the present disclosure will, of course, vary depending upon known factors, such as the pharmacodynamic characteristics of the particular agent and its mode and route of administration; the species, age, sex, health, medical condition, and weight of the recipient; the nature and extent of the symptoms; the kind of concurrent treatment; the frequency of treatment; the route of administration, the renal and hepatic function of the patient, and the effect desired. Compounds of this disclosure may be administered in a single daily dose, or the total daily dosage may be administered in divided doses of two, three, or four times daily.

In certain instances, it may be advantageous to administer the compound of the present disclosure in combination with one or more therapeutically active agents independently selected from anti-cancer agents, anti-allergic agents, anti-emetics, pain relievers, immunomodulators and cytoprotective agents.

The term "combination therapy" refers to the administration of two or more therapeutic agents to treat a therapeutic disease, disorder or condition described in the present disclosure. Such administration encompasses co-administration of these therapeutic agents in a substantially simultaneous manner, such as in a single capsule having a fixed ratio of active ingredients. Alternatively, such administration encompasses co-administration in multiple, or in separate containers (e.g., capsules, powders, and liquids) for each active ingredient. The compound of the present disclosure and additional therapeutic agents can be administered via the same administration route or via different administration routes. Powders and/or liquids may be reconstituted or diluted to a desired dose prior to administration. In addition, such administration also encompasses use of each type of therapeutic agent in a sequential manner, either at approximately the same time or at different times. In either case, the treatment regimen will provide beneficial effects of the drug combination in treating the diseases, conditions or disorders described herein.

General Chemotherapeutic agents considered for use in combination therapies include capecitabine (Xeloda®), N4-pentoxycarbonyl-5-deoxy-5-fluorocytidine, carboplatin (Paraplatin®), cisplatin (Platinol®), cladribine (Leustatin®), cyclophosphamide (Cytoxan® or Neosar®), cytarabine, cytosine arabinoside (Cytosar-U®), cytarabine liposome injection (DepoCyt®), dacarbazine (DTIC-Dome®), doxorubicin hydrochloride (Adriamycin®, Rubex®), fludarabine phosphate (Fludara®), 5-fluorouracil (Adrucil®, Efudex®), Gemcitabine (difluorodeoxycitidine), irinotecan (Camptosar®), L-asparaginase (ELSPAR®), 6-mercaptopurine (Purinethol®), methotrexate (Folex®), pentostatin, 6-thioguanine, thiotepa, and topotecan hydrochloride for injection (Hycamptin).

Anti-cancer agents of particular interest for combinations with the compounds of the present disclosure include:

Phosphoinositide 3-kinase (PI3K) inhibitors: 4-[2-(1H-Indazol-4-yl)-6-[[4-(methylsulfonyl)piperazin-1-yl]methyl] thieno[3,2-d]pyrimidin-4-yl]morpholine (also known as GDC 0941 and described in PCT Publication Nos. WO 09/036082 and WO 09/055730); 4-(trifluoromethyl)-5-(2,6-dimorpholinopyrimidin-4-yl)pyridin-2-amine (also known as BKM120 or NVP-BKM120, and described in PCT Publication No. WO2007/084786); Alpelisib (BYL719): (5Z)-5-[[4-(4-Pyridinyl)-6-quinolinyl]methylene]-2,4-thiazolidinedione (GSK1059615, CAS 958852-01-2); 5-[8-methyl-9-(1-methylethyl)-2-(4-morpholinyl)-9H-purin-6-yl]-2-pyrimidinamine (VS-5584, CAS 1246560-33-7) and everolimus (AFINITOR®).

Mitogen-activated protein kinase (MEK) inhibitors: XL-518 (also known as GDC-0973, Cas No. 1029872-29-4, available from ACC Corp.); Selumetinib (5-[(4-bromo-2-chlorophenyl)amino]-4-fluoro-N-(2-hydroxyethoxy)-1-methyl-1H-benzimidazole-6-carboxamide, also known as AZD6244 or ARRY 142886, described in PCT Publication No. WO2003077914); 2-[(2-Chloro-4-iodophenyl)amino]-N-(cyclopropylmethoxy)-3,4-difluoro-benzamide (also known as CI-1040 or PD184352 and described in PCT Publication No. WO2000035436); N-[(2R)-2,3-Dihydroxypropoxy]-3,4-difluoro-2-[(2-fluoro-4-iodophenyl)amino]-benzamide (also known as PD0325901 and described in PCT Publication No. WO2002006213); 2,3-Bis[amino[(2-aminophenyl)thio]methylene]-butanedinitrile (also known as U0126 and described in U.S. Pat. No. 2,779,780); N-[3,4-Difluoro-2-[(2-fluoro-4-iodophenyl)amino]-6-methoxyphenyl]-1-[(2R)-2,3-dihydroxypropyl]-cyclopropanesulfonamide (also known as RDEA119 or BAY869766 and described in PCT Publication No. WO2007014011); (3S,4R,5Z,8S,9S,11E)-14-(Ethylamino)-8,9,16-trihydroxy-3,4-dimethyl-3,4,9,19-tetrahydro-1H-2-benzoxacyclotetradecine-1,7(8H)-dione] (also known as E6201 and described in PCT Publication No. WO2003076424); 2'-Amino-3'-methoxyflavone (also known as PD98059 available from Biaffin GmbH & Co., KG, Germany); (R)-3-(2,3-Dihydroxypropyl)-6-fluoro-5-(2-fluoro-4-iodophenylamino)-8-methylpyrido[2,3-d]pyrimidine-4,7(3H,8H)-dione (TAK-733, CAS 1035555-63-5); Pimasertib (AS-703026, CAS 1204531-26-9); Trametinib dimethyl sulfoxide (GSK-1120212, CAS 1204531-25-80); 2-(2-Fluoro-4-iodophenylamino)-N-(2-hydroxyethoxy)-1,5-dimethyl-6-oxo-1,6-dihydropyridine-3-carboxamide (AZD 8330); 3,4-Difluoro-2-[(2-fluoro-4-iodophenyl)amino]-N-(2-hydroxyethoxy)-5-[(3-oxo-[1,2]oxazinan-2-yl)methyl]benzamide (CH 4987655 or Ro 4987655); ( ); and 5-[(4-Bromo-2-fluorophenyl)amino]-4-fluoro-N-(2-hydroxyethoxy)-1-methyl-1H-Benzimidazole-6-carboxamide (MEK162).

Epidermal growth factor receptor (EGFR) inhibitors: Erlotinib hydrochloride (Tarceva®), Gefitnib (Iressa®); Dacomitinib (PF299804); N-[4-[(3-Chloro-4-fluorophenyl)amino]-7-[[(3"S")-tetrahydro-3-furanyl]oxy]-6-quinazolinyl]-4(dimethylamino)-2-butenamide, Tovok®); Vandetanib (Caprelsa®); Lapatinib (Tykerb®); (3R,4R)-4-Amino-1-((4-((3-methoxyphenyl)amino)pyrrolo[2,1-f][1,2,4]triazin-5-yl)methyl)piperidin-3-ol (BMS690514); Canertinib dihydrochloride (CI-1033); 6-[4-[(4-Ethyl-1-piperazinyl)methyl]phenyl]-N-[(1R)-1-phenylethyl]-7H-Pyrrolo[2,3-d]pyrimidin-4-amine (AEE788, CAS 497839-62-0); Mubritinib (TAK165); Pelitinib (EKB569); Afatinib (BIBW2992); Neratinib (HKI-272); N-[4-[[1-[(3-Fluorophenyl)methyl]-1H-indazol-5-yl]amino]-5-methylpyrrolo[2,1-f][1,2,4]triazin-6-yl]-carbamic acid, (3S)-3-morpholinylmethyl ester (BMS599626); N-(3,4-Dichloro-2-fluorophenyl)-6-methoxy-7-[[(3aα,5β,6aα)-octahydro-2-methylcyclopenta[c]pyrrol-5-yl]methoxy]-4-quinazolinamine (XL647, CAS 781613-23-8); and 4-[4-[[(1R)-1-Phenylethyl]amino]-7H-pyrrolo[2,3-d]pyrimidin-6-yl]-phenol (PK1166, CAS 187724-61-4).

EGFR antibodies: Cetuximab (Erbitux®); Panitumumab (Vectibix®); Matuzumab (EMD-72000); Trastuzumab (Herceptin®); Nimotuzumab (hR3); Zalutumumab; TheraCIM h-R3; MDX0447 (CAS 339151-96-1); and ch806 (mAb-806, CAS 946414-09-1).

MAPK inhibitors: Vemurafinib (Zelboraf®), Sorafinib (Nexavar®), Dabrefinib (Tafinlar®), Trametinib (Mekinist®) and Selumetinib (AZD6244, ARRY-142886) EED/EZH2 inhibitors: tazemetostat (EPZ-6438), GSK2816126 (CAS 1346574-57-9), CPI-1205 (CAS 1621862-70-1) and DS-3201 (also known as DS-3201b, Daiichi Sankyo, Inc).

Immune checkpoint modulators: Pembrolizumab (Keytruda®), Nivolumab (Opdivo®), Atezolizumab (Tecentriq®) and Ipilumumab (Yervoy®).

Some patients may experience allergic reactions to the compounds of the present disclosure and/or other anti-cancer agent(s) during or after administration; therefore, anti-allergic agents are often administered to minimize the risk of an allergic reaction. Suitable anti-allergic agents include corticosteroids (Knutson, S., et al., PLoS One, DOI:10.1371/journal.pone.01 11840 (2014)), such as dexamethasone (e.g., Decadron®), beclomethasone (e.g., Beclovent®), hydrocortisone (also known as cortisone, hydrocortisone sodium succinate, hydrocortisone sodium phosphate, and sold under the tradenames Ala-Cort®, hydrocortisone phosphate, Solu-Cortef®, Hydrocort Acetate® and Lanacort®), prednisolone (sold under the tradenames Delta-Cortel®, Orapred®, Pediapred® and Prelone®), prednisone (sold under the tradenames Deltasone®, Liquid Red®, Meticorten® and Orasone®), methylprednisolone (also known as 6-methylprednisolone, methylprednisolone acetate, methylprednisolone sodium succinate, sold under the tradenames Duralone®, Medralone®, Medrol®, M-Prednisol® and Solu-Medrol®); antihistamines, such as diphenhydramine (e.g., Benadryl®), hydroxyzine, and cyproheptadine; and bronchodilators, such as the beta-adrenergic receptor agonists, albuterol (e.g., Proventil®), and terbutaline (Brethine®).

Some patients may experience nausea during and after administration of the compound of the present disclosure and/or other anti-cancer agent(s); therefore, anti-emetics are used in preventing nausea (upper stomach) and vomiting. Suitable anti-emetics include aprepitant (Emend®), ondansetron (Zofran®), granisetron HCl (Kytril®), lorazepam (Ativan®), dexamethasone (Decadron®), prochlorperazine (Compazine®), casopitant (Rezonic® and Zunrisa®), and combinations thereof.

Medication to alleviate the pain experienced during the treatment period is often prescribed to make the patient more comfortable. Common over-the-counter analgesics, such Tylenol®, are often used. However, opioid analgesic drugs such as hydrocodone/paracetamol or hydrocodone/acetaminophen (e.g., Vicodin®), morphine (e.g., Astramorph® or Avinza®), oxycodone (e.g., OxyContin® or Percocet®), oxymorphone hydrochloride (Opana®), and fentanyl (e.g., Duragesic®) are also useful for moderate or severe pain.

Immunomodulators of particular interest for combinations with the compounds of the present disclosure include: Afutuzumab (available from Roche®); Pegfilgrastim (Neulasta®); Lenalidomide (CC-5013, Revlimid®); Thalidomide (Thalomid®), Actimid (CC4047); and IRX-2 (mixture of human cytokines including interleukin 1, interleukin 2, and interferon γ, CAS 951209-71-5, available from IRX Therapeutics).

In an effort to protect normal cells from treatment toxicity and to limit organ toxicities, cytoprotective agents (such as neuroprotectants, free-radical scavengers, cardioprotectors, anthracycline extravasation neutralizers, nutrients and the like) may be used as an adjunct therapy. Suitable cytoprotective agents include Amifostine (Ethyol®), glutamine, dimesna (Tavocept®), mesna (Mesnex®), dexrazoxane (Zinecard® or Totect®), xaliproden (Xaprila®), and leucovorin (also known as calcium leucovorin, citrovorum factor and folinic acid).

The structure of the active compounds identified by code numbers, generic or trade names may be taken from the actual edition of the standard compendium "The Merck Index" or from databases, e.g. Patents International (e.g. IMS World Publications).

In one embodiment, the present disclosure provides pharmaceutical compositions comprising at least one compound of the present disclosure or a pharmaceutically acceptable salt thereof together with a pharmaceutically acceptable carrier suitable for administration to a human or animal subject, either alone or together with other anti-cancer agents.

In another embodiment, the present disclosure provides methods of treating human or animal subjects suffering from a cellular proliferative disease, such as malignancy. The present disclosure provides methods of treating a human or animal subject in need of such treatment, comprising administering to the subject a therapeutically effective amount of a compound of the present disclosure or a pharmaceutically acceptable salt thereof, either alone or in combination with other anti-cancer agents.

In particular, compositions will either be formulated together as a combination therapeutic or administered separately.

In one embodiment, the present disclosure provides a pharmaceutical combination comprising a compound of the present disclosure or a pharmaceutically acceptable salt thereof, and one or more therapeutically active agents selected from the group consisting of Abitrexate (Methotrexate), Abraxane (Paclitaxel Albumin-stabilized Nanoparticle Formulation), Afatinib Dimaleate, Afinitor (Everolimus), Alecensa (Alectinib), Alectinib, Alimta (Pemetrexed Disodium), Avastin (Bevacizumab), Bevacizumab, Carboplatin, Ceritinib, Crizotinib, Cyramza (Ramucirumab), Docetaxel, Erlotinib Hydrochloride, Everolimus, Folex (Methotrexate), Folex PFS (Methotrexate), Gefitinib, Gilotrif (Afatinib Dimaleate), Gemcitabine Hydrochloride, Gemzar (Gemcitabine Hydrochloride), Iressa (Gefitinib), Keytruda (Pembrolizumab), Mechlorethamine Hydrochloride, Methotrexate, Methotrexate LPF (Methotrexate), Mexate (Methotrexate), Mexate-AQ (Methotrexate), Mustargen (Mechlorethamine Hydrochloride), Navelbine (Vinorelbine Tartrate), Necitumumab, Nivolumab, Opdivo (Nivolumab), Osimertinib, Paclitaxel, Paclitaxel Albumin-stabilized Nanoparticle Formulation, Paraplat (Carboplatin), Paraplatin (Carboplatin), Pembrolizumab, Pemetrexed Disodium, Portrazza (Necitumumab), Ramucirumab, Tagrisso (Osimertinib), Tarceva (Erlotinib Hydrochloride), Taxol (Paclitaxel), Taxotere (Docetaxel), Vinorelbine Tartrate, Xalkori (Crizotinib), Zykadia (Ceritinib), CARBOPLATIN-TAXOL and GEMCITABINE-CISPLATIN, for the treatment of lung carcinoma (including, but not limited to, non-small cell lung carcinoma, lung adenocarcinoma, lung carcinoma, large cell lung carcinomas, non-small cell lung carcinoma, lung squamous cell carcinoma, small cell lung cancer).

In another embodiment, the present disclosure provides a pharmaceutical combination comprising a compound of the present disclosure or a pharmaceutically acceptable salt thereof, and one or more therapeutically active agents selected from the group consisting of Aldesleukin, Cobimetinib, Cotellic (Cobimetinib), Dabrafenib, Dacarbazine, DTIC-Dome (Dacarbazine), IL-2 (Aldesleukin), ImLygic (Talimogene Laherparepvec), Interleukin-2 (Aldesleukin), Intron A (Recombinant Interferon Alfa-2b), Ipilimumab, Keytruda (Pembrolizumab), Mekinist (Trametinib), Nivolumab, Opdivo (Nivolumab), Peginterferon Alfa-2b, PEG-Intron (Peginterferon Alfa-2b), Pembrolizumab, Proleukin (Aldesleukin), Recombinant Interferon Alfa-2b, Sylatron (Peginterferon Alfa-2b), Tafinlar (Dabrafenib), Talimogene Laherparepvec, Trametinib, Vemurafenib, Yervoy (Ipilimumab) and Zelboraf (Vemurafenib), for the treatment of melanoma (including, but not limited to, skin cutaneous melanoma, desmoplastic melanoma and uveal melanoma).

In combination therapy for treatment of a malignancy, the compound of the present disclosure and other anti-cancer agent(s) may be administered simultaneously, concurrently or sequentially with no specific time limits, wherein such administration provides therapeutically effective levels of the two compounds in the body of the subject.

In a preferred embodiment, the compound of the present disclosure and the other anti-cancer agent(s) is generally administered sequentially in any order by infusion or orally. The dosing regimen may vary depending upon the stage of the disease, physical fitness of the patient, safety profiles of the individual drugs, and tolerance of the individual drugs, as well as other criteria well-known to the attending physician and medical practitioner(s) administering the combination. The compound of the present disclosure and other anti-cancer agent(s) may be administered within minutes of each other, hours, days, or even weeks apart depending upon the particular cycle being used for treatment. In addition, the cycle could include administration of one drug more often than the other during the treatment cycle and at different doses per administration of the drug.

In another aspect of the present disclosure, a kit comprising two or more separate pharmaceutical compositions, at least one of which contains a compound of the present disclosure is provided. In one embodiment, the kit comprises means for separately retaining said compositions, such as a container, divided bottle, or divided foil packet. An example of such a kit is a blister pack, as typically used for the packaging of tablets, capsules and the like.

The kit of the present disclosure may be used for administering different dosage forms, for example, oral and parenteral, for administering the separate compositions at different dosage intervals, or for titrating the separate compositions against one another. To assist compliance, the kit of the present disclosure typically comprises directions for administration. A compound of the present disclosure may also be used to advantage in combination with known therapeutic processes, for example, the administration of hormones or especially radiation. A compound of the present disclosure may in particular be used as a radiosensitizer, especially for the treatment of tumors which exhibit poor sensitivity to radiotherapy.

In the combination therapies of the present disclosure, the compound of the present disclosure and the other therapeutic agent may be manufactured and/or formulated by the same or different manufacturers. Moreover, the compound of the present disclosure and the other therapeutic (or pharmaceutical agent) may be brought together into a combination therapy: (i) prior to release of the combination product to physicians (e.g. in the case of a kit comprising the compound of the present disclosure and the other therapeutic agent); (ii) by the physician themselves (or under the guidance of the physician) shortly before administration; (iii) in the patient themselves, e.g. during sequential administration of the compound of the present disclosure and the other therapeutic agent.

The pharmaceutical composition (or formulation) for application may be packaged in a variety of ways depending upon the method used for administering the drug. Generally, an article for distribution includes a container having deposited therein the pharmaceutical formulation in an appropriate form. Suitable containers are well-known to those skilled in the art and include materials such as bottles (plastic and glass), sachets, ampoules, plastic bags, metal cylinders, and the like. The container may also include a tamper-proof assemblage to prevent indiscreet access to the contents of the package. In addition, the container has deposited thereon a label that describes the contents of the container. The label may also include appropriate warnings.

The pharmaceutical composition or combination of the present disclosure can be in unit dosage of about 1-1000 mg of active ingredient(s) for a subject of about 50-70 kg, or about 1-500 mg or about 1-250 mg or about 1-150 mg or about 0.5-100 mg, or about 1-50 mg of active ingredients. The therapeutically effective dosage of a compound, the pharmaceutical composition, or the combinations thereof, is dependent on the species of the subject, the body weight, age and individual condition, the disorder or disease or the severity thereof being treated. A physician, clinician or veterinarian of ordinary skill can readily determine the effective amount of each of the active ingredients necessary to prevent, treat or inhibit the progress of the disorder or disease.

The above-cited dosage properties may be demonstrable in vitro and in vivo tests using advantageously mammals, e.g., mice, rats, dogs, monkeys or isolated organs, tissues and preparations thereof. The compounds of the present disclosure can be applied in vitro in the form of solutions, e.g., aqueous solutions, and in vivo either enterally, parenterally, advantageously intravenously, e.g., as a suspension or in aqueous solution. The dosage in vitro may range between about 10-3 molar and 10-9 molar concentrations. A therapeutically effective amount in vivo may range depending on the route of administration, between about 0.1-500 mg/kg, or between about 1-100 mg/kg.

Pharmacology and Utility

Mutations in SWI/SNF chromatin remodeling complexes are highly prevalent in cancers, occurring at a frequency of approximately 20% (Kadoch, C., Hargreaves, D. C., et al. 2013 Nat Genet. 45: 592-601) (Shain, A. H., and Pollack, J. R. 2013 PLoS ONE 8(1): e55119). SWI/SNF complexes consist of multiple subunits, and function in ATP-dependent remodeling of chromatin to control key cellular events such as regulation of gene expression. The catalytic ATPase subunits within the SWI/SNF complex consist of either BRM/SMARCA2 or BRG1/SMARCA4, and are thus mutually exclusive (Hodges, C., Kirkland, J. G., et al. 2016 Cold Spring Harb Persp Med 6(8)). Functional genomics screening via shRNAs, has revealed a compelling synthetic lethal relationship between these two SWI/SNF ATPases, BRM and BRG1 (Hoffman, G. R; Rahal, R et al. 2014 PNAS 111(8): 3128-33; Wilson, B. G., Helming, K. C., et al. 2014 Molecular and Cellular Biology 34(6): 1136-44). In particular, cancer cells lacking functional BRG1, such as through loss of function mutations or deletions, are exquisitely sensitive to depletion of BRM via shRNA mediated knockdown, resulting in growth inhibition (Hoffman, G. R., Rahal, R et al., 2014 PNAS 111(8): 3128-33; Oike, T., Ogiwara, H., et al. 2013 Cancer Research 73(17): 5508-5518); and Vangamudi, B., Paul, T. A., et al. 2015 Cancer Research 75(18): 3865-3878). Therefore, these studies reveal that in the absence of one of the SWI/SNF ATPases, cancer cells can become highly dependent on the remaining ATPase for survival, uncovering a vulnerability that can be exploited for targeted therapy. Genetic lesions in BRG1 have indeed been identified in various cancers, predominantly in non-small cell lung cancers at approximately 10%, but also in other cancer types such as liver, pancreatic, melanomas etc. (Imielinski, M., A. H. Berger, et al. (2012) Cell 150(6): 1107-1120); The Cancer Genome Atlas (TCGA) Data Portal, and the cBioPortal for Cancer Genomics). As such, these constitute highly significant patient populations with clear unmet medical need, and would be predicted to benefit from therapeutic inhibition of BRM. Just as certain cancer cells are dependent on BRM due to loss of BRG1 function, interestingly, other cancer types have been reported to be BRG1-dependent potentially occurring through various mechanisms including mutations in other subunits of the SWI/SNF complex (Shi, J; Whyte, W. A., et al. 2013 Genes and Development 27(24): 2648-2662; Xi, W., Sansam, C. G., et al. 2009 Cancer Research 69(20): 8094-8101; and Zuber, J., Shi, J., et al. 2011 Nature 478(7370), 524-528). In addition, SWI/SNF activity has also been reported to be altered in other disease settings, making it an attractive therapeutic target in other diseases besides cancer (Han, P., Li, W., et al. 2014 Nature 514(7520): 102-06). Therefore, the potential to inhibit either ATPase or both can have multiple applications in treating different types of cancers and diseases.

BRG1 mutations, deletions or loss of expression that can lead to loss of function can occur in various types of cancers (The Cancer Genome Atlas (TCGA) Data Portal; the cBioPortal for Cancer Genomics; Becker, T. M., S. Haferkamp, et al. (2009) Mol Cancer 8: 4; Matsubara, D., Kishaba, Y., et al. 2013 Cancer Science 104(2): 266-273; and Yoshimoto, T., Matsubara, D., et al. 2015 Pathology International 65(11): 595-602). Examples of specific types of cancers with BRG1 mutation, deletions, or loss of expression include, but are not limited to non-small cell lung carcinoma, lung adenocarcinoma, lung carcinoma, large cell lung carcinomas, non-small cell lung carcinoma, lung squamous cell carcinoma, small cell lung cancer, skin cutaneous melanoma, desmoplastic melanoma, uveal melanoma, small cell carcinoma of the ovary, cutaneous squamous cell carcinoma, glioma, uterine carcinosarcoma, uterine corpus endometrial carcinoma, ovarian serous cystadenocarcinoma, bladder urothelial carcinoma, primary central nervous system lymphoma, esophageal carcinoma, bladder cancer, bladder cancer plasmacytoid variant, stomach adenocarcinoma, adenoid cystic carcinoma, lymphoid neoplasm diffuse large B-cell lymphoma, pancreatic cancer, colorectal adenocarcinoma, cholangiocarcinoma, sarcoma, head and neck cancers, cervical and endocervical cancers, medulloblastoma, cutaneous T cell lymphoma, liver hepatocellular carcinoma, kidney renal papillary cell carcinoma, breast cancer, mantle cell lymphoma, gallbladder carcinoma, testicular germ cell cancers, kidney renal cell clear cell carcinoma, prostate cancer, pediatric ewing sarcoma, thymoma, kidney chromophobe, renal non-clear cell carcinoma, pheochromocytoma and paraganglioma, thyroid cancers.

SMARCB1/SNF5-mutant cancers including malignant rhabdoid tumors in which BRG1-dependency has been demonstrated (Xi, W., Sansam, C. G., et al. 2009 Cancer Research 69(20): 8094-8101), but also SMARCB1/SNF-mutant epithelioid sarcomas, familial schwannomatosis, renal medullary carcinomas and Ewing sarcomas (Jahromi, M. S; Putnam, A. R, et al. 2012 Cancer Genetics 205(7-8): 391-404; Prensner, J. R., Iyer, M. K., et al. 2013 Nature Genetics 45(11): 1392-8; and Roberts, C. W. M., and Biegel, J. A., 2009 Cancer Biology and Therapy 8(5): 412-416) and cancers in which SNF5 is deficient in the SWI/SNF complex not arising through mutations, such as in synovial sarcomas (Kadoch, C., and Crabtree, G. R., 2013 Cell 153(1): 71-85) as well as BRG1-dependent hematopoietic malignancies such as acute myeloid leukemias (AML) (Shi, J., Whyte, W. A., et al. 2013 Genes and Development 27(24): 2648-2662; and Zuber, J., Shi, J., et al. 2011 Nature 478(7370), 524-528). BRM-mutant (including deleted) or SNF5/SMARCB1 mutant (including deleted) cancers (The Cancer Genome Atlas (TCGA) Data Portal, and the cBioPortal for Cancer Genomics) include but not limited to malignant peripheral nerve sheath tumor, neuroendocrine prostate cancer, breast cancer, bladder urothelial carcinoma, adenoid cystic carcinoma, stomach adenocarcinoma, ovarian serous cystadenocarcinoma, uterine carcinosarcoma, esophageal carcinoma, head and neck squamous cell carcinoma, non-small cell lung carcinomas, lung adenocarcinoma, lung squamous cell carcinoma, small cell lung cancer, pancreatic cancer, adrenocortical carcinoma, skin cutaneous melanoma, sarcoma, colorectal adenocarcinoma, cervical and endocervical cancers, liver hepatocellular carcinoma, cutaneous squamous cell carcinoma, testicular germ cell cancer, glioblastoma, glioblastoma multiforme, cholangiocarcinoma, Ewing's sarcoma, clear cell renal cell carcinoma, neuroblastoma, thymoma, diffuse large B cell lymphoma, acute myeloid leukemia, chronic lymphocytic leukemia, medulloblastoma, pheochromocytoma and paraganglioma and multiple myeloma.

Dual inhibitors in which there is a benefit of either BRM, BRG1, or BRM and BRG1 inhibition may also be applicable in cancers containing mutations or deficiencies in SWI/SNF subunits other than BRG1/SMARCA4, BRM/SMARCA2, or SNF5/SMARCB1 as detailed above, such as ARID1A, ARID1B, ARID2, PBRM1, SMARCE1, SMARCC1, SMARCC2, PHF10, DPF1, DPF3, DPF2, ACTL6A, ACTL6B, SMARCD2, SMARCD3, SMARCD1, BCL11A, BCL11B, BCL7A, BCL7B, BCL7C, BRD9 and ACTB. In other cases, dependency on BRM/BRG1 ATPases may arise from mechanisms other than SWI/SNF mutations.

Compounds of the present disclosure have favorable therapeutic benefits for BRM-mediated and/or BRG1-mediated disorders or diseases. The compounds of present disclosure in free form or in pharmaceutically acceptable salt form, exhibit valuable pharmacological properties, which can be demonstrated at least by using any one of the following test procedures. Compounds of the present disclosure were assessed for their ability to inhibit BRM and BRG1 activity in biochemical assays.

BRM ATPase Inhibition Assay

I. Isolation of the Recombinant BRM ATPase Domain

A. Cloning of $His_{10}$-ZZ-HCV3C-BRM(636-1331) into pFastBac1

Sequences encoding a $His_{10}$ tag (SEQ ID NO: 1), the immunoglobulin G (IgG) binding ZZ domain of protein A (*Staphylococcus aureus*) and a human rhinovirus 3C protease site were fused upstream of BRM residues 636-1331 using standard DNA synthesis methods. The synthesized construct was cloned into the MCS of pFastBac1 (Life Technologies) by PCR amplification using the following 5' and 3' primers: 5'-GACCGAACTAGTATGGCTTCTCAC-CACCAT-3' (SEQ ID NO: 2) and 5'-AGCGTTAAGCTTT-TAATCCTCGATGGCGCG-3' (SEQ ID NO: 3) to include a stop codon and ligated into SpeI and HindIII sites using standard molecular biology techniques. The final recombinant vector, pFB1-$His_{10}$-ZZ-HCV3C-BRM (636-1331), results in the expression of a HCV3C protease-cleavable $His_{10}$-ZZ tag (underlined) upstream of native BRM sequences encoding the ATPase and SnAC domains.

(SEQ ID NO: 4)
MASHHHHHHHHHHAQHDEAVDNKFNKEQQNAFYEILHLPNLNEEQRNAF

IQSLKDDPSQSANLLAEAKKLNDAQAPKVDNKFNKEQQNAFYEILHLPN

LNEEQRNAFIQSLKDDPSQSANLLAEAKKLNDAQAPKVDANGGGSGGG

GSLEVLFQGPEESDSDYEEEDEEEESSRQETEEKILLDPNSEEVSEKDA

KQIIETAKQDVDDEYSMQYSARGSQSYYTVAHAISERVEKQSALLINGT

LKHYQLQGLEWMVSLYNNNLNGILADEMGLGKTIQTIALITYLMEHKRL

NGPYLIIVPLSTLSNWTYEFDKWAPSVVKISYKGTPAMRRSLVPQLRSG

KFNVLLTTYEYIIKDKHILAKIRWKYMIVDEGHRMKNHHCKLTQVLNTH

YVAPRRILLTGTPLQNKLPELWALLNFLLPTIFKSCSTFEQWFNAPFAM

TGERVDLNEEETILIIRRLHKVLRPFLLRRLKKEVESQLPEKVEYVIKC

DMSALQKILYRHMQAKGILLTDGSEKDKKGKGGAKTLMNTIMQLRKICN

HPYMFQHIEESFAEHLGYSNGVINGAELYRASGKFELLDRILPKLRATN

HRVLLFCQMTSLMTIMEDYFAFRNFLYLRLDGTTKSEDRAALLKKFNEP

GSQYFIFLLSTRAGGLGLNLQAADTVVIFDSDWNPHQDLQAQDRAHRIG

QQNEVRVLRLCTVNSVEEKILAAAKYKLNVDQKVIQAGMFDQKSSSHER

RAFLQAILEHEEENEEEDEVPDDETLNQMIARREEEFDLFMRMDMDRRR

EDARNPKRKPRLMEEDELPWIIKDDAEVERLTCEEEEEKIFGRGSRQRR

DVDYSDALTEKQWLRAIED

B. Expression of BRM (636-1331)

The recombinant vector generated above was used to make recombinant bacmid by transforming to DH10Bac cells using standard protocols as detailed by the manufacturer (Life Technologies). High titer P3 virus was generated by transfecting the bacmid to *Spodoptera frugiperda* 9 (Sf9) cells and amplifying the virus using standard methods as detailed by Life Technologies. $His_{10}$-ZZ-HCV3C-BRM (636-1331) was expressed from 25 L of Sf9 cells in log phase growth ($1.5 \times 10^6$ cells/mL) in a WAVE bioreactor (GE Healthcare Life Sciences) at a 1:100 v/v of virus. The infection was allowed to proceed on the rocking incubator at 27° C. and harvested three days post infection after cell viability had dropped to 80% with an increase in the overall cell diameter consistent with infection. Cells were harvested @4,000×g for 20 min, flash frozen and stored at −80° C. until use.

C. Purification of BRM (636-1331)

Sf9 cells expressing recombinant $His_{10}$-ZZ-HCV3C-BRM(636-1331) were lysed in 50 mM Tris (8.0), 300 mM NaCl, 10% glycerol and 2 mM TCEP supplemented with a protease inhibitor cocktail (Roche cOmplete), using 7.5 mL lysis buffer per gram of cell paste. Cells were lysed upon thawing, homogenized and subsequently clarified in a JA25.50 rotor @50,000×g for 30 min to remove insoluble material. The clarified lysate was applied to a 5 mL His-Trap HP column (GE Healthcare Life Sciences), washed rigorously in lysis buffer without protease inhibitors supplemented with 25 mM imidazole. Bound protein was eluted over a fifteen column volume gradient against lysis buffer supplemented with 500 mM imidazole. Fractions containing $His_{10}$-ZZ-HCV3C-BRM (636-1331) were pooled and dialyzed overnight against 50 mM Tris (8.0), 300 mM NaCl, 10% glycerol and 2 mM TCEP supplemented with HCV3C protease to effect removal of the $His_{10}$-ZZ tag. Cleavage was monitored by coomassie-stained SDS/PAGE and LC/MS. The intact mass was consistent with BRM residues 636-1331 proceeded by two non-native amino acids, Gly-Pro, a residual of the HCV3C cleavage site. The expected mass was 160 Da greater than predicted, consistent with two phosphorylation sites.

The cleaved product was diluted in dialysis buffer not supplemented with salt to a final NaCl concentration of 100 mM, passed thru a 0.2 μm syringe filter and immediately loaded to a 1 mL HiTrap Q HP column (GE Health Biosciences) previously equilibrated in 50 mM Tris (8.0), 100 mM NaCl, 10% glycerol & 1 mM TCEP. Following capture, the bound protein was competed against the same buffer supplemented with 1 M NaCl. Fractions containing BRM (636-1331) were pooled and loaded to a S200 16/60 size exclusion column equilibrated in 50 mM Tris (8.0), 200 mM NaCl, 10% glycerol & 2 mM TCEP. The purified construct was concentrated to 2.5 mg/mL, flash frozen and stored @-80° C. until used in downstream assays.

II. Brm ATPase Inhibition Activity

Compound inhibition of ATPase activity of Brm ATPase-SnAC (636-1331) was measured by using the ADP-Glo assay kit from Promega (V6930). 120 nL of compound in 100% DMSO were transferred to a white 384 well microtiter assay plate using an ATS Acoustic Transfer System from EDC Biosystems. All subsequent reagent additions were performed using a MultiFlo FX Multi-Mode Dispenser. Assay buffer was 20 mM HEPES pH 7.5, 1 mM $MgCl_2$, 20 mM KCl, 1 mM DTT, 0.01% BSA, 0.005% Tween 20. 4 µL of 7.5 nM Brm ATPase-SnAC in assay buffer was added to the assay plate and incubated at RT for 5 min with compound. 2 µL of 255 µM ATP and 6 nM pCMV-dR8.91 plasmid in assay buffer was added to assay plate to initiate the reaction. The final concentrations of reagents were 5 nM BRM ATPase-SnAC, 85 µM ATP, and 2 nM pCMV-dR8.91 plasmid. The ATPase reaction was incubated at RT for 60 min. 3 µL of ADP-Glo reagent was added to stop the reaction and was incubated for 30 min at RT. 3 µL of Kinase detection reagent was added to the assay plate which was incubated for 90 min at RT. Plates were read with a 2103 Multilabel Envision reader using ultrasensitive luminescence detection. $IC_{50}$ values were determined from the average of duplicate data points by non-linear regression analysis of percent inhibition values plotted versus compound concentration.

BRG1 ATPase Inhibition Assay

1. Isolation of the Recombinant BRG1 ATPase Domain

A. Cloning of BRG1(658-1361)-$His_6$ into pDEST8

The construct BRG1(658-1361)-$His_6$ for expression in insect cells was sub-cloned from a full length BRG1 plasmid, pDONR221-BRG1-$His_6$ (OPS7173) by PCR as follows. An ATTB flanked PCR fragment encoding BRG1(658-1361)-$His_6$ was generated using the following primers: Forward, ATTB1 BRG1(658-x) 5'-GGGGACAAGTTTGTA-CAAAAAAGCAGGCTTCGAAGGAGATAGAAC-CATGGA AGAAAGTGGCTCAGAAGAAGAGGAAG (SEQ ID NO: 5); Reverse, BRG1(x-1361)HISstpATTB2rev, 5'-GGGGACCACTTTGTA-CAAGAAAGCTGGGTCTCAGTGATGATGATGAT-GATGCTCCTCGATG GCCTTGAGCCACTGC (SEQ ID NO: 6). This PCR fragment was recombined into the vector pDEST8 using the Gateway® method following the manufacturer's protocol (Life Technologies). The insertion was confirmed by sequencing and entered into the OPS database (OPS8023) before proceeding to bacmid generation.

```
                                     (SEQ ID NO: 7)
MEESGSEEEE EEEEEEQPQA AQPPTLPVEE KKKIPDPDSD

DVSEVDARHI IENAKQDVDD EYGVSQALAR GLQSYYAVAH

AVTERVDKQS ALMVNGVLKQ YQIKGLEWLV SLYNNNLNGI

LADEMGLGKT IQTIALITYL MEHKRINGPF LIIVPLSTLS

NWAYEFDKWA PSVVKVSYKG SPAARRAFVP QLRSGKFNVL

LTTYEYIIKD KHILAKIRWK YMIVDEGHRM KNHHCKLTQV

LNTHYVAPRR LLLTGTPLQN KLPELWALLN FLLPTIFKSC

STFEQWFNAP FAMTGEKVDL NEEETILIIR RLHKVLRPFL
```

-continued

```
LRRLKKEVEA QLPEKVEYVI KCDMSALQRV LYRHMQAKGV

LLTDGSEKDK KGKGGTKTLM NTIMQLRKIC NHPYMFQHIE

ESFSEHLGFT GGIVQGLDLY RASGKFELLD RILPKLRATN

HKVLLFCQMT SLMTIMEDYF AYRGFKYLRL DGTTKAEDRG

MLLKTFNEPG SEYFIFLLST RAGGLGLNLQ SADTVIIFDS

DWNPHQDLQA QDRAHRIGQQ NEVRVLRLCT VNSVEEKILA

AAKYKLNVDQ KVIQAGMFDQ KSSSHERRAF LQAILEHEEQ

DEEEDEVPDD ETVNQMIARH EEEFDLFMRM DLDRRREEAR

NPKRKPRLME EDELPSWIIK DDAEVERLTC EEEEEKMFGR

GSRHRKEVDY SDSLTEKQWL KAIEEHHHHH H
```

B. Expression of BRG1(658-1361)-$His_6$

The recombinant vector generated above was used to make recombinant bacmid by transforming to DH10Bac cells using standard protocols as detailed by the manufacturer (Life Technologies). High titer P3 virus was generated by transfecting the bacmid to Spodoptera frugiperda 9 (Sf9) cells and amplifying the virus using standard methods as detailed by Life Technologies. BRG1 (658-1361)-$His_6$ was expressed from Sf9 cells in log phase growth (1.5-3.9×$10^6$ cells/mL) at a 15 virus/cell. The infection was allowed to proceed on the rocking incubator at 27° C. and harvested three days post infection after cell viability had dropped to 80% with an increase in the overall cell diameter consistent with infection. Cells were harvested @4,000×g for 20 min, flash frozen and stored at -80° C. until use.

C. Purification of BRG1(658-1361)-$His_6$

Sf9 cells expressing recombinant BRG1(658-1361)-$His_6$ were lysed in 50 mM Tris (8.0), 300 mM NaCl, 5% glycerol and 1 mM TCEP supplemented with a protease inhibitor cocktail (Roche cOmplete), using 7.5 mL lysis buffer per gram of cell paste. Cells were lysed upon thawing, homogenized and subsequently clarified in a JA25.50 rotor @50,000×g for 30 min to remove insoluble material. The clarified lysate was applied to a 5 mL His-Trap HP column (GE Healthcare Life Sciences), washed rigorously in lysis buffer without protease inhibitors supplemented with 20 mM imidazole. Bound protein was eluted over a ten column volume gradient against lysis buffer supplemented with 250 mM imidazole. Fractions containing BRG1(658-1361)-$His_6$ were pooled and diluted till conductivity reached about 6 mS/cm (~60 mM NaCl) using 50 mM Tris pH 8.0, 5% glycerol, and 1 mM TCEP, passed thru a 0.2p filter and immediately loaded to a 5 mL HiTrap Q HP column (GE Health Biosciences) previously equilibrated in 50 mM Tris (pH8.0), 100 mM NaCl, 5% glycerol, and 1 mM TCEP. Following capture, the bound protein was competed against the same buffer supplemented with 1 M NaCl. Fractions containing BRG1(658-1361)-$His_6$ were pooled and loaded to a S200 16/60 size exclusion column equilibrated in 50 mM Tris (8.0), 200 mM NaCl, 5% glycerol, and 1 mM TCEP. The purified construct was concentrated to 1 to 2.5 mg/mL, flash frozen and stored @-80° C. until used in downstream assays.

BRG1 ATPase Inhibition Activity

Compound inhibition of ATPase activity of Brg1 ATPase-SnAC (658-1361) was measured by using the ADP-Glo assay kit from Promega (V6930). 120 nL of compound in 100% DMSO were transferred to a white 384 well microtiter assay plate using an ATS Acoustic Transfer System from EDC Biosystems. All subsequent reagent additions were performed using a MultiFlo FX Multi-Mode Dispenser. Assay buffer was 20 mM HEPES pH 7.5, 1 mM MgCl$_2$, 20 mM KCl, 1 mM DTT, 0.01% BSA, 0.005% Tween 20. 4 µL of 7.5 nM Brg1 ATPase-SnAC in assay buffer was added to the assay plate and incubated at RT for 5 min with compound. 2 µL of 195 µM ATP and 6 nM pCMV-dR8.91 plasmid in assay buffer was added to assay plate to initiate the reaction. The final concentrations of reagents were 5 nM Brg1 ATPase-SnAC, 65 µM ATP, and 2 nM pCMV-dR8.91 plasmid. The ATPase reaction was incubated at RT for 60 min. 3 µL of ADP-Glo reagent was added to stop the reaction and was incubated for 30 min at RT. 3 µL of Kinase detection reagent was added to the assay plate which was incubated for 90 min at RT. Plates were read with a 2103 Multilabel Envision reader using ultrasensitive luminescence detection. IC$_{50}$ values were determined from the average of duplicate data points by non-linear regression analysis of percent inhibition values plotted versus compound concentration.

pCMV-dR8.91 Plasmid Used for BRM/BRG1 ATPase Inhibition Assays:

The plasmid template pCMV-dR8.91 (see sequence below) is propagated using One Shot Stbl3 Chemically Competent *E. coli* (Catalog Number C73C7303, Invitrogen/Thermo Fisher Scientific) following the transformation protocol provided with the reagent. Transformed bacterial colonies are then selected on LB agar plates containing ampicillin/carbenicllin antibiotic selection medium (Catalog Number L1010, Teknova). Bacterial colonies are grown in LB liquid broth (Catalog number 10855001, Invitrogen) containing ampicillin at 100 micrograms/mL and plasmid DNA isolated according to required scale according to the manufacturers protocol provided with the Qiagen Plasmid Isolation Kits (Maxi prep, Product Id Number 10063).

```
(SEQ ID NO: 8)
ttgattattgactagttattaatagtaatcaattacgggtcattagttc atagcccatatatggagttccgcgttacataacttacggtaaatggcccg cctggctgaccgcccaacgaccccgcccattgacgtcaataatgacgta tgttcccatagtaacgccaatagggactttccattgacgtcaatgggtgg agtatttacggtaaactgcccacttggcagtacatcaagtgtatcatatg ccaagtacgccccctattgacgtcaatgacggtaaatggcccgcctggca ttatgcccagtacatgaccttatgggactttcctacttggcagtacatct acgtattagtcatcgctattaccatggtgatgcggttttggcagtacatc aatgggcgtggatagcggtttgactcacggggatttccaagtctccaccc cattgacgtcaatgggagtttgttttggcaccaaaatcaacgggactttc caaaatgtcgtaacaactccgccccattgacgcaaatgggcggtaggcgt gtacggtgggaggtctatataagcagagctcgtttagtgaaccgtcagat cgcctggagacgccatccacgctgttttgacctccatagaagacaccggg accgatccagcctccgcggccgggaacggtgcattggaacgcggattccc cgtgccaagagtgacgtaagtaccgcctatagagtctataggcccacccc cttggcttcttatgcgacggatcgatcccgtaataagcttcgaggtccgc ggccggccgcgttgacgcgcacggcaagaggcgaggggcggcgactggtg agagatgggtgcgagagcgtcagtattaagcgggggagaattagatcgat gggaaaaaattcggttaaggccagggggaaagaaaaaatataaattaaaa catatagtatgggcaagcagggagctagaacgattcgcagttaatcctgg cctgttagaaacatcagaaggctgtagacaaatactgggacagctacaac catcccttcagacaggatcagaagaacttagatcattatataatacagta gcaaccctctattgtgtgcatcaaaggatagagataaaagacaccaagga agctttagacaagatagaggaagagcaaaacaaaagtaagaaaaaagcac agcaagcagcagctgacacaggacacagcaatcaggtcagccaaaattac cctatagtgcagaacatccaggggcaaatggtacatcaggccatatcacc tagaactttaaatgcatgggtaaaagtagtagaagagaaggctttcagcc cagaagtgatacccatgtttcagcattatcagaaggagccaccccacaa gatttaaacaccatgctaaacacagtggggggacatcaagcagccatgca aatgttaaaagagaccatcaatgaggaagctgcagaatgggatagagtgc atccagtgcatgcagggcctattgcaccaggccagatgagagaaccaagg ggaagtgacatagcaggaactactagtacccttcaggaacaaataggatg gatgacacataatccacctatcccagtaggagaaatctataaaagatgga taatcctgggattaaataaaatagtaagaatgtatagccctaccagcatt ctggacataagacaaggaccaaaggaacccttttagagactatgtagaccg attctataaaactctaagagccgagcaagcttcacaagaggtaaaaaatt ggatgacagaaaccttgttggtccaaaatgcgaacccagattgtaagact attttaaaagcattgggaccaggagcgacactagaagaaatgatgacagc atgtcagggagtgggggaaccggccataaagcaagagttttggctgaag caatgagccaagtaacaaatccagctaccataatgatacagaaaggcaat tttaggaaccaaagaaagactgttaagtgtttcaattgtggcaaagaagg gcacatagccaaaaattgcagggccctaggaaaaagggctgttggaaat gtggaaaggaaggacaccaaatgaaagattgtactgagagacaggctaat ttttttagggaagatctggccttcccacaagggaaggccagggaattttct tcagagcagaccagagccaacagccccaccagaagagagcttcaggtttg gggaagagacaacaactccctctcagaagcaggagccgatagacaaggaa ctgtatcctttagcttccctcagatcactctttggcagcgacccctcgtc acaataaagataggggggcaattaaaggaagctctattagatacaggagc agatgatacagtattagaagaaatgaatttgccaggaagatggaaaccaa aaatgatagggggaattggaggttttatcaaagtaagacagtatgatcag atactcatagaaatctgcggacataaagctataggtacagtattagtagg acctacacctgtcaacataattggaagaaatctgttgactcagattggct gcactttaaattttcccattagtcctattgagactgtaccagtaaaatta aagccaggaatggatggcccaaaagttaaacaatggccattgacagaaga aaaaataaaagcattagtagaaatttgtacagaaatggaaaaggaaggaa aaatttcaaaaattgggcctgaaaatccatacaatactccagtatttgcc ataaagaaaaagacagtactaaatggagaaaattagtagatttcagaga acttaataagagaactcaagatttctgggaagttcaattaggaataccac atcctgcagggttaaaacagaaaaaatcagtaacagtactggatgtgggc
```

-continued

```
gatgcatattttcagttcccttagataaagacttcaggaagtatactgc
atttaccatacctagtataaacaatgagacaccagggattagatatcagt
acaatgtgcttccacagggatggaaaggatcaccagcaatattccagtgt
agcatgacaaaaatcttagagccttttagaaaacaaaatccagacatagt
catctatcaatacatggatgatttgtatgtaggatctgacttagaaatag
ggcagcatagaacaaaaatagaggaactgagacaacatctgttgaggtgg
ggatttaccacaccagacaaaaaacatcagaaagaacctccattcctttg
gatgggttatgaactccatcctgataaaatggacagtacagcctatagtgc
tgccagaaaaggacagctggactgtcaatgacatacagaaattagtgggaa
aaattgaattgggcaagtcagatttatgcagggattaaagtaaggcaatt
atgtaaacttcttaggggaaccaaagcactaacagaagtagtaccactaa
cagaagaagcagagctagaactggcagaaaacagggagattctaaaagaa
ccggtacatggagtgtattatgacccatcaaaagacttaatagcagaaat
acagaagcaggggcaaggccaatggacatatcaaatttatcaagagccat
ttaaaaatctgaaaacaggaaagtatgcaagaatgaagggtgcccacact
aatgatgtgaaacaattaacagaggcagtacaaaaaatagccacagaaag
catagtaatatgggaaagactcctaaatttaaattacccatacaaaagg
aaacatgggaagcatggtggacagagtattggcaagccacctggattcct
gagtgggagtttgtcaatacccctcccttagtgaagttatggtaccagtt
agagaaagaacccataataggagcagaaactttctatgtagatggggcag
ccaatagggaaactaaattaggaaaagcaggatatgtaactgacagagga
agacaaaaagttgtccccctaacggacacaacaaatcagaagactgagtt
acaagcaattcatctagctttgcaggattcgggattagaagtaaacatag
tgacagactcacaatatgcattgggaatcattcaagcacaaccagataag
agtgaatcagagttagtcagtcaaataatagagcagttaataaaaaagga
aaaagtctacctggcatgggtaccagcacacaaaggaattggaggaaatg
aacaagtagataaattggtcagtgctggaatcaggaaagtactattttta
gatggaatagataaggcccaagaagaacatgagaaatatcacagtaattg
gagagcaatggctagtgattttaacctaccacctgtagtagcaaaagaaa
tagtagccagctgtgataaatgtcagctaaaaggggaagccatgcatgga
caagtagactgtagcccaggaatatggcagctagattgtacacatttaga
aggaaaagttatcttggtagcagttcatgtagccagtggatatatagaag
cagaagtaattccagcagagacagggcaagaaacagcatacttcctctta
aaattagcaggaagatggccagtaaaaacagtacatacagacaatggcag
caatttcaccagtactacagttaaggccgcctgttggtgggcgggatca
agcaggaatttggcattccctacaatccccaaagtcaaggagtaatagaa
tctatgaataaagaattaagaaaaattataggacaggtaagagatcaggc
tgaacatcttaagacagcagtacaaatggcagtattcatccacaatttta
aaagaaaaggggggattggggggtacagtgcaggggaaagaatagtagac
ataatagcaacagacatacaaactaaagaattacaaaaacaaattacaaa
aattcaaaattttcgggtttattacagggacagcagagatccagtttgga
```

-continued

```
aaggaccagcaaagctcctctggaaaggtgaaggggcagtagtaatacaa
gataatagtgacataaaagtagtgccaagaagaaaagcaaagatcatcag
ggattatggaaaacagatggcaggtgatgattgtgtggcaagtagacagg
atgaggattaacacatggaattctgcaacaactgctgtttatccatttca
gaattgggtgtcgacatagcagaataggcgttactcgacagaggagagca
agaaatggagccagtagatcctagactagagccctggaagcatccaggaa
gtcagcctaaaactgcttgtaccaattgctattgtaaaagtgttgcttt
cattgccaagtttgtttcatgacaaaagccttaggcatctcctatggcag
gaagaagcggagacagcgacgaagagctcatcagaacagtcagactcatc
aagcttctctatcaaagcagtaagtagtacatgtaatgcaacctataata
gtagcaatagtagcattagtagtagcaataataatagcaatagttgtgtg
gtccatagtaatcatagaatataggaaaatggccgctgatcttcagacct
ggaggaggagatatgagggacaattggagaagtgaattatataaatataa
agtagtaaaaattgaaccattaggagtagcacccaccaaggcaaagagaa
gagtggtgcagagagaaaaaagagcagtgggaataggagctttgttcctt
gggttcttgggagcagcaggaagcactatgggcgcagcgtcaatgacgct
gacggtacaggccagacaattattgtctggtatagtgcagcagcagaaca
atttgctgagggctattgaggcgcaacagcatctgttgcaactcacagtc
tggggcatcaagcagctccaggcaagaatcctggctgtggaaagatacct
aaaggatcaacagctcctggggatttggggttgctctggaaaactcattt
gcaccactgctgtgccttggaatgctagttggagtaataaatctctggaa
cagatttggaatcacacgacctggatggagtgggacagagaaattaacaa
ttacacaagcttaatacactccttaattgaagaatcgcaaaaccagcaag
aaaagaatgaacaagaattattggaattagataaatgggcaagtttgtgg
aattggttaacataacaaattggctgtggtatataaaattattcataat
gatagtaggaggcttggtaggtttaagaatagttttgctgtactttcta
tagtgaatagagttaggcagggatattcaccattatcgtttcagacccac
ctcccaaccccgaggggacccgacaggcccgaaggaatagaagaagaagg
tggagagagagacagagacagatccattcgattagtgaacggatccttgg
cacttatctgggacgatctgcggagcctgtgcctcttcagctaccaccgc
ttgagagacttactcttgattgtaacgaggattgtggaacttctgggacg
caggggtgggaagcccctcaaatattggtggaatctcctacaatattgga
gtcaggagctaaagaatagtgctgttagcttgctcaatgccacagccata
gcagtagctgaggggacagataggttatagaagtagtacaaggagcttg
tagagctattcgccacatacctagaagaataagacagggcttggaaagga
ttttgctataagctcgaggccgccccggtgaccttcagaccttggcactg
gaggtggcccggcagaagcgcggcatcgtggatcagtgctgcaccagcat
ctgctctctctaccaactggagaactactgcaactaggcccaccactacc
ctgtccacccctctgcaatgaataaaacctttgaaagagcactacaagtt
gtgtgtacatgcgtgcatgtgcatatgtggtgcgggggaacatgagtgg
```

```
ggctggctggagtggcgatgataagctgtcaaacatgagaattaattctt
gaagacgaaagggcctcgtgatacgcctattttttataggttaatgtcatg
ataataatggtttcttagtctagaattaattccgtgtattctatagtgtc
acctaaatcgtatgtgtatgatacataaggttatgtattaattgtagccg
cgttctaacgacaatatgtacaagcctaattgtgtagcatctggcttact
gaagcagaccctatcatctctctcgtaaactgccgtcagagtcggtttgg
ttggacgaaccttctgagtttctggtaacgccgtcccgcacccggaaatg
gtcagcgaaccaatcagcagggtcatcgctagccagatcctctacgccgg
acgcatcgtggccggcatcaccggcgccacaggtgcggttgctggcgcct
atatcgccgacatcaccgatggggaagatcgggctcgccacttcgggctc
atgagcgcttgtttcggcgtgggtatggtggcaggccccgtggccggggg
actgttgggcgccatctccttgcatgcaccattccttgcggcggcggtgc
tcaacggcctcaacctactactgggctgcttcctaatgcaggagtcgcat
aagggagagcgtcgaatggtgcactctcagtacaatctgctctgatgccg
catagttaagccagccccgacacccgccaacacccgctgacgcgccctga
cgggcttgtctgctcccggcatccgcttacagacaagctgtgaccgtctc
cgggagctgcatgtgtcagaggttttcaccgtcatcaccgaaacgcgcga
gacgaaagggcctcgtgatacgcctattttttataggttaatgtcatgata
ataatgtttcttagacgtcaggtggcacttttcggggaaatgtgcgcgg
aacccctatttgtttattttttctaaatacattcaaatatgtatccgctca
tgagacaataaccctgataaatgcttcaataatattgaaaaggaagagt
atgagtattcaacatttccgtgtcgcccttattccctttttttgcggcatt
ttgccttcctgtttttgctcacccagaaacgctggtgaaagtaaaagatg
ctgaagatcagttgggtgcacgagtgggttacatcgaactggatctcaac
agcggtaagatccttgagagttttcgccccgaagaacgttttccaatgat
gagcacttttaaagttctgctatgtggcgcggtattatcccgtattgacg
ccgggcaagagcaactcggtcgccgcatacactattctcagaatgacttg
gttgagtactcaccagtcacagaaaagcatcttacggatggcatgacagt
aagagaattatgcagtgctgccataaccatgagtgataacactgcggcca
acttacttctgacaacgatcggaggaccgaaggagctaaccgcttttttg
cacaacatgggggatcatgtaactcgccttgatcgttgggaaccggagct
gaatgaagccataccaaacgacgagcgtgacaccacgatgcctgtagcaa
tggcaacaacgttgcgcaaactattaactggcgaactacttactctagct
tcccggcaacaattaatagactggatggaggcggataaagttgcaggacc
acttctgcgctcggcccttccggctggctggtttattgctgataaatctg
gagccggtgagcgtgggtctcgcggtatcattgcagcactggggccagat
ggtaagccctcccgtatcgtagttatctacacgacggggagtcaggcaac
tatggatgaacgaaatagacagatcgctgagataggtgcctcactgatta
agcattggtaactgtcagaccaagtttactcatatatactttagattgat
ttaaaacttcatttttaatttaaaaggatctaggtgaagatcctttttga
taatctcatgaccaaaatcccttaacgtgagttttcgttccactgagcgt
cagaccccgtagaaaagatcaaaggatcttcttgagatcctttttttctg
cgcgtaatctgctgcttgcaaacaaaaaaaccaccgctaccagcggtggt
ttgtttgccggatcaagagctaccaactcttttttccgaaggtaactggct
tcagcagagcgcagataccaaatactgttcttctagtgtagccgtagtta
ggccaccacttcaagaactctgtagcaccgcctacatacctcgctctgct
aatcctgttaccagtggctgctgccagtggcgataagtcgtgtcttaccg
ggttggactcaagacgatagttaccggataaggcgcagcggtcgggctga
acggggggttcgtgcacacagcccagcttggagcgaacgacctacaccga
actgagatacctacagcgtgagctatgagaaagcgccacgcttcccgaag
ggagaaaggcggacaggtatccggtaagcggcagggtcggaacaggagag
cgcacgagggagcttccaggggaaacgcctggtatctttatagtcctgt
cgggttcgccacctctgacttgagcgtcgatttttgtgatgctcgtcag
gggggcggagcctatggaaaaacgccagcaacgcggcctttttacggttc
ctggccttttgctggccttttgctcacatgttctttcctgcgttatcccc
tgattctgtggataaccgtattaccgcctttgagtgagctgataccgctc
gccgcagccgaacgaccgagcgcagcgagtcagtgagcgaggaagcggaa
gagcgcccaatacgcaaaccgcctctccccgcgcgttggccgattcatta
atgcagctgtggaatgtgtgtcagttagggtgtggaaagtccccaggctc
cccagcaggcagaagtatgcaaagcatgcatctcaattagtcagcaacca
ggtgtggaaagtccccaggctccccagcaggcagaagtatgcaaagcatg
catctcaattagtcagcaaccatagtcccgcccctaactccgcccatccc
gcccctaactccgccagttccgcccattctccgccccatggctgactaa
ttttttttatttatgcagaggccgaggccgcctcggcctctgagctattc
cagaagtagtgaggaggcttttttggaggcctaggcttttgcaaaaagct
tggacacaagacaggcttgcgagatatgtttgagaataccactttatccc
gcgtcagggagaggcagtgcgtaaaaagacgcggactcatgtgaaatact
ggttttagtgcgccagatctctataatctcgcgcaacctattttcccct
cgaacactttttaagccgtagataaacaggctgggacacttcacatgagc
gaaaaatacatcgtcacctgggacatgttgcagatccatgcacgtaaact
cgcaagccgactgatgccttctgaacaatggaaaggcattattgccgtaa
gccgtggcggtctgtaccgggtgcgttactggcgcgtgaactgggtattc
gtcatgtcgataccgtttgtatttccagctacgatcacgacaaccagcgc
gagcttaaagtgctgaaacgcgcagaaggcgatggcgaaggcttcatcgt
tattgatgacctggtggataccggtggtactgcggttgcgattcgtgaaa
tgtatccaaaagcgcacttttgtcaccatcttcgcaaaaccggctggtcgt
ccgctggttgatgactatgttgttgatatcccgcaagatacctggattga
acagcgtgggatatgggcgtcgtattcgtcccgccaatctccggtcgct
aatcttttcaacgcctggcactgccgggcgttgttcttttttaacttcagg
cgggttacaatagtttccagtaagtattctggaggctgcatccatgacac
aggcaaacctgagcgaaacctgttcaaaccccgctttaaacatcctgaa
```

-continued acctcgacgctagtccgccgctttaatcacggcgcacaaccgcctgtgca gtcggcccttgatggtaaaaccatccctcactggtatcgcatgattaacc gtctgatgtggatctggcgcggcattgacccacgcgaaatcctcgacgtc caggcacgtattgtgatgagcgatgccgaacgtaccgacgatgatttata cgatacggtgattggctaccgtggcggcaactggatttatgagtgggccc cggatctttgtgaaggaaccttacttctgtggtgtgacataattggacaa actacctacagagatttaaagctctaaggtaaatataaaatttttaaccc ggatctttgtgaaggaaccttacttctgtggtgtgacataattggacaaa ctacctacagagatttaaagctctaaggtaaatataaaatttttaagtgt ataatgtgttaaactactgattctaattgtttgtgtattttagattccaa cctatggaactgatgaatgggagcagtggtggaatgcctttaatgaggaa aacctgttttgctcagaagaaatgccatctagtgatgatgaggctactgc tgactctcaacattctactcctccaaaaagaagagaaaggtagaagacc ccaaggactttccttcagaattgctaagttttttgagtcatgctgtgttt agtaatagaactcttgcttgctttgctatttacaccacaaaggaaaaagc tgcactgctatacaagaaaattatggaaaaatattctgtaacctttataa gtaggcataacagttataatcataacatactgttttttcttactccacac aggcatagagtgtctgctattaataactatgctcaaaaattgtgtaccctt tagcttttaatttgtaaaggggttaataaggaatatttgatgtatagtg ccttgactagagatcataatcagccataccacatttgtagaggttttact tgctttaaaaaacctcccacacctcccctgaacctgaaacataaaatga atgcaattgttgttgttgggctgcaggaattaattcgagctcgcccgaca The inhibitory activity data of representative compounds of the present disclosure from the two assays described above (e.g., the BRM ATPase Inhibition Assay; and the BRG1 ATPase Inhibition Assay) are provided in the following Table 1.

TABLE 1

| Example No | BRM IC$_{50}$ (μM) | BRG1 IC$_{50}$ (μM) |
| --- | --- | --- |
| 1 | 0.005 | 0.006 |
| 2 | 0.033 | 0.03 |
| 3 | 0.010 | 0.010 |
| 4 | <0.005 | <0.005 |
| 5 | <0.005 | <0.005 |
| 6 | <0.005 | <0.005 |
| 7 | <0.005 | <0.005 |
| 8 | 0.09 | 0.019 |

What is claimed is:

1. A method of preparing a compound of formula I:

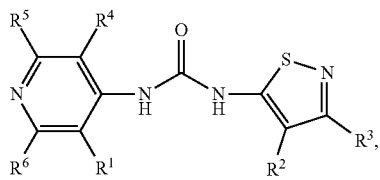

or a pharmaceutically acceptable salt thereof;

wherein said method comprises the step of reacting compound of Formula (I-1):

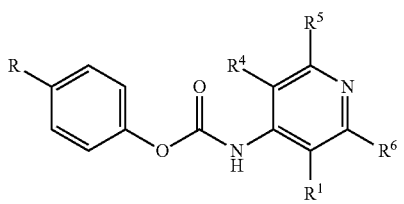

with a compound of Formula (I-2):

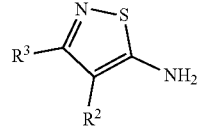

in the presence of a base;
wherein
R is a H or a nitro group;
$R^1$ and $R^6$ are as defined below or groups which may undergo further transformation to provide a compound of Formula (I-1) wherein
$R^1$ is selected from hydrogen, amino and hydroxy-substituted $C_{1-2}$alkyl;
$R^2$ is hydrogen;
$R^3$ is selected from $C_{1-2}$alkyl and halo-substituted-$C_{1-2}$alkyl;
$R^4$ is hydrogen;
$R^5$ is selected from hydrogen and halo; and
$R^6$ is selected from hydrogen and halo.

2. The method of claim 1 wherein the step of reacting compound of Formula (I-1) with a compound of Formula (I-2) is carried out in a solvent selected from tetrahydrofuran (THF) and dioxane.

3. The method of claim 1 wherein the base is diisopropylethylamine (DIPEA).

4. The method of claim 1 wherein the step of reacting compound of Formula (I-1) with a compound of Formula (I-2) is carried out at room temperature or at a temperature of 60° C.

5. The method of claim 1 wherein the compound of Formula (I-2) is first deprotonated in the presence of a base which is lithium hexamethyldisilazide (LHMDS), followed by the reaction with the compound of Formula (I-1).

6. The method according to claim 1 further comprising the step of preparing the compound of Formula (I-1), wherein said step comprises reacting compound of Formula (I-1a):

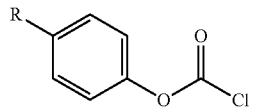

with a compound of Formula (I-1b):

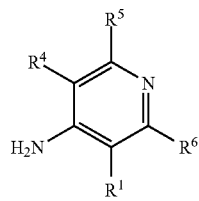

in the presence of a base.

7. The method of claim 6 wherein the step of reacting compound of Formula (I-1a) and the compound of Formula (I-1b) is carried out in a solvent selected from dichloromethane and dioxane.

8. The method of claim 6 wherein the base is pyridine.

9. The method of claim 6 wherein the step of reacting compound of Formula (I-1a) and the compound of Formula (I-1b) is carried out at room temperature.

10. The method of claim 1 wherein in the compound of Formula (I),
    $R^1$ is selected from hydrogen, amino and hydroxy-methyl;
    $R^2$ is hydrogen;
    $R^3$ is selected from methyl, difluoromethyl and trifluoromethyl;
    $R^4$ is hydrogen;
    $R^5$ is selected from hydrogen, chloro and fluoro; and
    $R^6$ is selected from hydrogen and fluoro.

11. The method of claim 1 wherein the compound of Formula (I) is selected from:

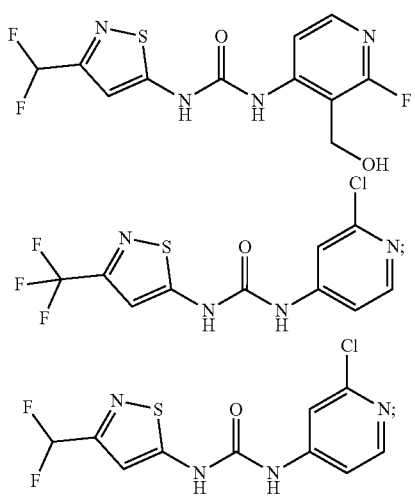

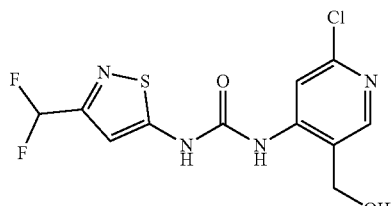

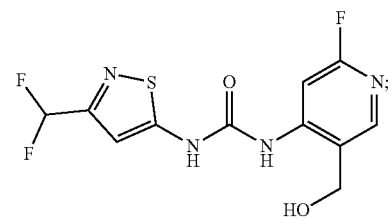

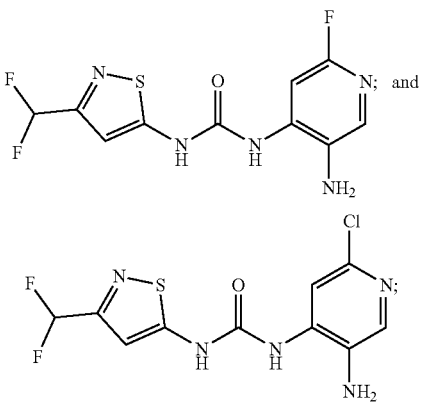

or a pharmaceutically acceptable salt thereof.

12. The method of claim 1 comprising the step of reacting a compound of Formula (I-1) which is:

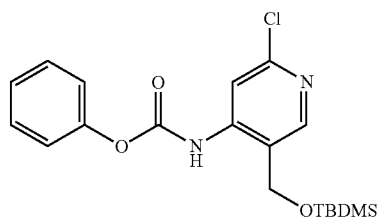 [SMILES: CC(C)(C)[Si](C)(C)OCc1cnc(Cl)cc1NC(=O)Oc1ccccc1]

wherein TBDMS is t-butyldimethylsilyl,
with a compound of Formula (I-2) which is:

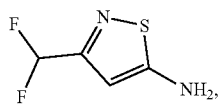

in the presence of the base LHMDS in the solvent N,N-dimethylformamide (DMF) at room temperature to prepare compound having the following Formula:

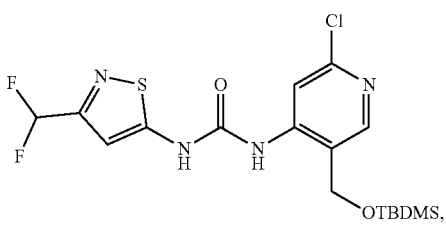 [SMILES: CC(C)(C)[Si](C)(C)OCc1cnc(Cl)cc1NC(=O)Nc1cc(C(F)F)ns1]
which undergo further transformation by reaction with TBAF in THF at room temperature to generate compound of Formula (I):
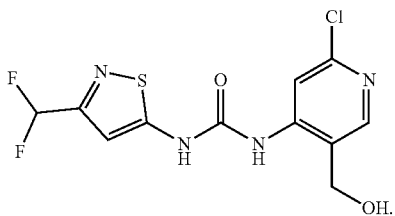 [SMILES: O=C(Nc1cc(C(F)F)ns1)Nc1cc(Cl)ncc1CO]
13. The method of claim 12 further comprising the step of reacting:
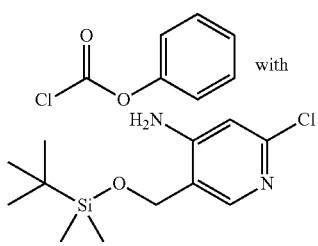
in the presence of the base pyridine and in the solvent dichloromethane at room temperature to generate:
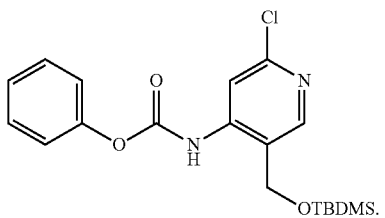 [SMILES: CC(C)(C)[Si](C)(C)OCc1cnc(Cl)cc1NC(=O)Oc1ccccc1]
* * * * *